US011013758B2

(12) United States Patent
Murray et al.

(10) Patent No.: US 11,013,758 B2
(45) Date of Patent: *May 25, 2021

(54) ALLELE SPECIFIC MODULATORS OF P23H RHODOPSIN

(71) Applicant: Ionis Pharmaceuticals, Inc., Carlsbad, CA (US)

(72) Inventors: Susan F. Murray, Poway, CA (US); Punit P. Seth, Carlsbad, CA (US); Michael L. McCaleb, La Jolla, CA (US); Susan M. Freier, San Diego, CA (US); Priyam Singh, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/553,799

(22) Filed: Aug. 28, 2019

(65) Prior Publication Data
US 2020/0069722 A1 Mar. 5, 2020

Related U.S. Application Data

(63) Continuation of application No. 15/553,876, filed as application No. PCT/US2016/019725 on Feb. 26, 2016, now Pat. No. 10,426,789.

(60) Provisional application No. 62/121,286, filed on Feb. 26, 2015.

(51) Int. Cl.
| | | |
|---|---|---|
| C12N 15/11 | (2006.01) | |
| A61K 48/00 | (2006.01) | |
| C07H 21/02 | (2006.01) | |
| C07H 21/04 | (2006.01) | |
| A61K 31/713 | (2006.01) | |
| A61P 27/02 | (2006.01) | |
| A61K 31/475 | (2006.01) | |
| A61K 31/704 | (2006.01) | |
| C07K 14/705 | (2006.01) | |

(52) U.S. Cl.
CPC .......... *A61K 31/713* (2013.01); *A61K 31/475* (2013.01); *A61K 31/704* (2013.01); *A61P 27/02* (2018.01); *C07K 14/70571* (2013.01); *C12N 2310/11* (2013.01); *C12N 2310/315* (2013.01); *C12N 2310/322* (2013.01); *C12N 2310/3231* (2013.01); *C12N 2310/3341* (2013.01); *C12N 2310/34* (2013.01); *C12N 2310/341* (2013.01); *C12N 2310/345* (2013.01); *C12N 2310/346* (2013.01); *C12N 2320/34* (2013.01); *C12Q 2600/178* (2013.01)

(58) Field of Classification Search
CPC .. A61K 31/475; A61K 31/713; A61K 31/704; C12N 15/113; C12N 15/1137; C12N 15/1138; C12N 2310/11; C12N 2310/315; C12N 2310/346; C12N 2310/341; C12N 2310/3341
See application file for complete search history.

(56) References Cited

U.S. PATENT DOCUMENTS

| | | | |
|---|---|---|---|
| 5,225,546 | A | 7/1993 | Dryja et al. |
| 5,262,529 | A | 11/1993 | Dryja et al. |
| 5,498,521 | A | 3/1996 | Dryja et al. |
| 5,801,154 | A | 9/1998 | Baracchini et al. |
| 6,225,291 | B1 | 5/2001 | Lewin et al. |
| 6,582,908 | B2 | 6/2003 | Fodor et al. |
| 7,138,378 | B1 | 11/2006 | Farrar et al. |
| 7,687,616 | B1 | 3/2010 | Bentwich et al. |
| 7,745,391 | B2 | 6/2010 | Mintz et al. |
| 8,450,473 | B2 | 5/2013 | Sullivan |
| 8,551,970 | B2 | 10/2013 | Farrar et al. |
| 8,673,560 | B2 | 3/2014 | Leamon et al. |
| 8,921,331 | B2 | 12/2014 | Bennett et al. |

(Continued)

FOREIGN PATENT DOCUMENTS

| | | |
|---|---|---|
| WO | WO2002088320 A2 | 11/2002 |
| WO | WO2010127209 A2 | 11/2010 |

(Continued)

OTHER PUBLICATIONS

ARVO Annual Meeting Abstract, Jun. 2013 referenced in Investigative Ophthalmology and Visual Science, Jun. 2013 vol. 54, 653.

(Continued)

*Primary Examiner* — Terra C Gibbs

(74) *Attorney, Agent, or Firm* — Knobbe, Martens, Olson & Bear, LLP

(57) ABSTRACT

The present embodiments provide methods, compounds, and compositions for treating, preventing, ameliorating, or slowing progression of retinitis pigmentosa (RP), such as autosomal dominant retinitis pigmentosa (AdRP) by administering a P23H rhodopsin specific inhibitor to a subject. The present embodiments provided herein are directed to compounds and compositions useful for treating, preventing, ameliorating, or slowing progression of retinitis pigmentosa (RP), such as autosomal dominant retinitis pigmentosa (AdRP). In certain embodiments, P23H rhodopsin inhibitors provided herein are allele-specific antisense compounds targeted to a P23H mutant allele that are capable of selectively inhibiting expression of P23H rhodopsin mutant protein to a greater extent than wild-type protein. In certain embodiments, administration of the allele specific antisense compounds in a subject having AdRP results in selective inhibition of P23H rhodopsin and allows the normal protein produced from the wild-type allele to maintain rod survival and function in the subject.

10 Claims, No Drawings

Specification includes a Sequence Listing.

(56) References Cited

U.S. PATENT DOCUMENTS

| | | | |
|---|---|---|---|
| 10,426,789 B2* | 10/2019 | Murray | C07K 14/70571 |
| 2001/0053519 A1 | 12/2001 | Fodor et al. | |
| 2003/0228597 A1 | 12/2003 | Cowsert et al. | |
| 2005/0096282 A1 | 5/2005 | Lewin et al. | |
| 2007/0031844 A1 | 2/2007 | Khvorova et al. | |
| 2009/0233368 A1 | 9/2009 | Farrar et al. | |
| 2010/0298417 A1 | 11/2010 | Freier et al. | |
| 2012/0204282 A1 | 8/2012 | Zhang et al. | |
| 2013/0028889 A1 | 1/2013 | Hnik et al. | |
| 2014/0107180 A1 | 4/2014 | Macleod et al. | |
| 2014/0323707 A1 | 10/2014 | Seth | |

FOREIGN PATENT DOCUMENTS

| | | |
|---|---|---|
| WO | WO2013120003 A1 | 8/2013 |
| WO | WO2013173637 A1 | 11/2013 |

OTHER PUBLICATIONS

Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Extended Search Report for 16756422.8 dated Oct. 9, 2018.
Froebel et al. (Invest Opthamol Vis Sci. 2017 vol. 58:3576-3591).
GenBank Accession No. NM_000539.2. *Homo sapiens* rhodopsin (opsin 2, rod pigment) (retinitis pigmentosa 4, autosomal dominant) (RHO), mRNA. Downloaded from https://www.ncbi.nlm.nih.gov/nuccore/NM_000539.2 on Oct. 24, 2018.
Gorbatyuk et al., "Suppression of mouse rhodopsin expression in vivo by AAV mediated siRNA delivery" Vision Res (2007) 47(9): 1202-1208.
Hernan et al., "Cellular Expression and siRNA-Mediated Interference of Rhodopsin cis-Acting Splicing Mutants Associated with Autosomal Dominant Retinitis Pigmentosa" Invest Ophthalmol Vis Sci (2011) 52(6): 3723-3729.
International Search Report for PCT/US2016/019725 dated Jul. 28, 2016.
MES Vision, Knowledge Center. Retinitis Pigmentosa? Downloaded from https://www.mesvision.com/knowledgeCenter/retinitusPigmentosa.htm on Apr. 15, 2018.
Murrat et al., IOVS, vol. 56, No. 11, pp. 6362-6375, Oct. 2015.
Murray et al. (Invest Opthalmol Vis Sci 2015 vol. 56:6362-6375).
Murray et al., "Prevention of photoreceptor cell degeneration in P23H rats after allele-specific knockdown of mutant Rhodopsin RNA expression using antisense oligonucleotide (ASO) treatment" Invest Ophthalmol Vis Sci (2014) ARVO Annual Meeting Abstract, vol. 55.
Murray et al., "The Use of Antisense Oligoucleotides to Reduce Rhodopsin mRNA and Protein Levels in Photoreceptor Cells in the Mouse Retina", Abstract, Isis Pharmaceuticals, 2013 Oligonucleotide Therapeutics Society (OTS) Annual Meeting held on Oct. 6-8, 2013.
Murray, Sue, "Antisense Applications for Ophthalmic Diseases Rhodopsin: a Photoreceptor Cell Specific Target for Retinitis Pigmentosa", Isis Pharmaceuticals, Inc., Abstract #082, 2013 Oligonucleotide Therapeutics Society (OTS) Annual Meeting held on Oct. 6-8, 2013.
Murray, Sue, "Prevention of Photoreceptor Degeneration in P23H Rats after Allele-Specific Knockdown of Mutant Rhodopsin RNA Expression using Antisense Oligonucleotide (ASO) Treatment", Isis Pharmaceuticals, Inc., Abstract #1258, 2014 Association for Research in Vision and Ophthalmology (ARVO) Annual Meeting held on May 4-8, 2014.
New England Biolabs 1998/99 Catalog (cover page and pp. 121 and 284).
Orhan, et al., "Genotypic and Phenotypic Characterization of P23H Line 1 Rat Model", Plos One, May 26, 2015.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Tessitore et al., "Preferential silencing of a common dominant rhodopsin mutation does not inhibit retinal degeneration in a transgenic model" Mol Ther (2006) 14(5): 692-699.

* cited by examiner

ALLELE SPECIFIC MODULATORS OF P23H RHODOPSIN

CROSS-REFERENCE TO RELATED APPLICATIONS

This application is a continuation of U.S. patent application Ser. No. 15/553,876, filed Aug. 25, 2017, now U.S. Pat. No. 10,426,789, which is a U.S. National Phase under 35 U.S.C. § 371 of International Application No. PCT/US2016/019725, filed Feb. 26, 2016, which claims priority to U.S. Provisional Patent Application No. 62/121,286, filed Feb. 26, 2015, each of which is hereby incorporated by reference in its entirety into this application.

SEQUENCE LISTING

The present application is being filed along with a Sequence Listing in electronic format. The Sequence Listing is provided as a file entitled BIOL0267WOSEQ_ST25.txt created Feb. 26, 2016, which is 60 kb in size. The information in the electronic format of the sequence listing is incorporated herein by reference in its entirety.

FIELD

The present embodiments provide methods, compounds, and compositions for treating, preventing, ameliorating, or slowing progression of retinitis pigmentosa (RP), such as autosomal dominant retinitis pigmentosa (AdRP) by administering a P23H rhodopsin specific inhibitor to a subject.

BACKGROUND

Retinitis pigmentosa (RP) is a broad description for pigment changes and/or damage in the retina. A hereditary fonn of retinitis pigmentosa called autosomal dominant retinitis pigmentosa (AdRP) is a degenerative disease that typically causes blindness by middle age. Bird A C, *American journal of ophthalmology* 1995; 119:543-562; Boughman J A et al. *Am J Hum Genet* 1980; 32:223-235; Schuster A et al. *Br J Ophthalmol* 2005; 89:1258-1264. AdRP is caused by abnormalities of the photoreceptors (rods and cones) or the retinal pigment epithelium (RPE) of the retina leading to progressive sight loss. AdRP patients may experience defective light to dark, dark to light adaptation or night blindness as the result of the degeneration of the peripheral visual field. AdRP results in loss of photoreceptor (rods) cells from peripheral retina and then cones from central retina.

Over 100 rhodopsin mutations have been identified in patients with AdRP. Sullivan L S et al. *Invest Ophthalmol Vis Sci* 2006; 47:3052-3064; Wang D Y et al. *Clinica chimica acta; international journal of clinical chemistry* 2005; 351: 5-16. The P23H mutation is the most prevalent mutation and is present in ~25% of AdRP and 5-15% of RP cases. Dryja T P et al. *Proc Natl Acad Sci USA* 1991; 88:9370-9374. Mutant rhodopsin protein such as P23H has a toxic gain-of-function that induces misfolding and disruption of normal rhodopsin protein, which leads to photoreceptor cell apoptosis. Typically, rods degenerate first, affecting low light vision. Then, cones degenerate, affecting bright light and color vision. The age of onset is variable with gradual progressive reduction in night and peripheral vision, often leading to "gun-barrel" visual field or tunnel vision. Median age of night-blindness onset is 12-14 years old. Blindness is frequent in middle ages and most rod cells are lost by age 40.

SUMMARY

The present embodiments provided herein are directed to potent, tolerable, and/or selective compounds and compositions useful for treating, preventing, ameliorating, or slowing progression of retinitis pigmentosa (RP), such as autosomal dominant retinitis pigmentosa (AdRP). In certain embodiments, P23H rhodopsin inhibitors provided herein are allele-specific antisense compounds targeted to a P23H mutant allele that are capable of selectively inhibiting expression of P23H rhodopsin mutant protein to a greater extent than wild-type protein. In certain embodiments, administration of the allele-specific antisense compounds in a subject having AdRP results in selective inhibition of P23H rhodopsin and allows the normal protein produced from the wild-type allele to maintain rod survival and function in the subject.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by ISIS number (ISIS #) indicate a combination of nucleobase sequence, chemical modification, and motif.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification at the 2' position of a sugar ring, e.g. a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5 position. A 5-methylcytosine is a modified nucleobase.

"About" means within +10% of a value. For example, if it is stated, "the compounds affected at least about 70% inhibition of P23H rhodopsin, it is implied that P23H rhodopsin levels are inhibited within a range of 60% and 80%.

"Administration" or "administering" refers to routes of introducing an antisense compound provided herein to a subject to perform its intended function. An example of a route of administration that can be used includes, but is not limited to intravitreal administration.

"Allele specific" with respect to an inhibitor refers to an inhibitor, such as an antisense compound, designed to hybridize to and/or inhibit expression of a transcript from one allele of a gene to a greater extent than the other allele of the gene.

"Amelioration" refers to a lessening of at least one indicator, sign, or symptom of an associated disease, disorder, or condition. In certain embodiments, amelioration includes a delay or slowing in the progression of one or more indicators of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding region or segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

"Cap structure" or "terminal cap moiety" means chemical modifications, which have been incorporated at either terminus of an antisense compound.

"cEt" or "constrained ethyl" means a bicyclic sugar moiety comprising a bridge connecting the 4'-carbon and the 2'-carbon, wherein the bridge has the formula: 4'-CH($CH_3$)—O-2'.

"Constrained ethyl nucleoside" (also cEt nucleoside) means a nucleoside comprising a bicyclic sugar moiety comprising a 4'-CH($CH_3$)—O-2' bridge.

"P23H rhodopsin" means any nucleic acid or protein of P23H rhodopsin. "P23H rhodopsin nucleic acid" means any nucleic acid encoding P23H rhodopsin. For example, in certain embodiments, a P23H rhodopsin nucleic acid includes a DNA sequence encoding P23H rhodopsin, an RNA sequence transcribed from DNA encoding P23H rhodopsin (including genomic DNA comprising introns and exons), and an mRNA sequence encoding P23H rhodopsin. "P23H rhodopsin mRNA" means an mRNA encoding a P23H rhodopsin protein.

"P23H rhodopsin specific inhibitor" refers to any agent capable of specifically inhibiting P23H rhodopsin RNA and/or P23H rhodopsin protein expression or activity at the molecular level. For example, P23H rhodopsin specific inhibitors include nucleic acids (including antisense compounds), peptides, antibodies, small molecules, and other agents capable of inhibiting the expression of P23H rhodopsin RNA and/or P23H rhodopsin protein.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Complementarity" means the capacity for pairing between nucleobases of a first nucleic acid and a second nucleic acid.

"Comprise," "comprises" and "comprising" will be understood to imply the inclusion of a stated step or element or group of steps or elements but not the exclusion of any other step or element or group of steps or elements.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Identifying an animal having, or at risk for having, a disease, disorder and/or condition" means identifying an animal having been diagnosed with the disease, disorder and/or condition or identifying an animal predisposed to develop the disease, disorder and/or condition. Such identification may be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Inhibiting the expression or activity" refers to a reduction, blockade of the expression or activity and does not necessarily indicate a total elimination of expression or activity.

"Internucleoside linkage" refers to the chemical bond between nucleosides.

"Lengthened" antisense oligonucleotides are those that have one or more additional nucleosides relative to an antisense oligonucleotide disclosed herein.

"Linked deoxynucleoside" means a nucleic acid base (A, G, C, T, U) substituted by deoxyribose linked by a phosphate ester to form a nucleotide.

"Linked nucleosides" means adjacent nucleosides linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase.

"Modified oligonucleotide" means an oligonucleotide comprising at least one modified internucleoside linkage, a modified sugar, and/or a modified nucleobase.

"Modified sugar" means substitution and/or any change from a natural sugar moiety.

"Modulating" refers to changing or adjusting a feature in a cell, tissue, organ or organism. For example, modulating P23H rhodopsin mRNA can mean to increase or decrease the level of P23H rhodopsin mRNA and/or P23H rhodopsin protein in a cell, tissue, organ or organism. A "modulator" effects the change in the cell, tissue, organ or organism. For example, a P23H rhodopsin antisense compound can be a modulator that decreases the amount of P23H rhodopsin mRNA and/or P23H rhodopsin protein in a cell, tissue, organ or organism.

"Monomer" refers to a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound "Prevent" refers to delaying or forestalling the onset, development or progression of a disease, disorder, or condition for a period of time from minutes to indefinitely. Prevent also means reducing the risk of developing a disease, disorder, or condition.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Segments" are defined as smaller or sub-portions of regions within a target nucleic acid.

"Selective" with respect to an effect refers to a greater effect on one thing over another by any quantitative extent or fold-difference. For example, an antisense compound that is "selective" for P23H rhodopsin or "selectively" targets or inhibits P23H rhodopsin, reduces expression of the P23H rhodopsin allele to a greater extent than the wild-type allele.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Sites," as used herein, are defined as unique nucleobase positions within a target nucleic acid.

"Slows progression" means decrease in the development of the said disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments. "Stringent hybridization conditions" or "stringent conditions" refer to conditions under which an oligomeric compound will hybridize to its target sequence, but to a minimal number of other sequences.

"Specifically inhibit" a target nucleic acid means to reduce or block expression of the target nucleic acid while exhibiting fewer, minimal, or no effects on non-target nucleic acids and does not necessarily indicate a total elimination of the target nucleic acid's expression.

"Subject" means a human or non-human animal selected for treatment or therapy.

"Target" refers to a protein, the modulation of which is desired.

"Target gene" refers to a gene encoding a target.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to an animal in order to effect an alteration or improvement of a disease, disorder, or condition in the animal. In certain embodiments, one or more pharmaceutical compositions can be administered to the animal.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. P3-D-ribonucleosides) or a DNA nucleotide (i.e. P3-D-deoxyribonucleoside).

Certain Embodiments

Certain embodiments provide methods, compounds and compositions for inhibiting or selectively inhibiting P23H rhodopsin expression.

Certain embodiments provide antisense compounds targeted to a P23H rhodopsin nucleic acid. In certain embodiments, the human mutant P23H rhodopsin nucleic acid has a C to A substitution at nucleotide 163 of GENBANK Accession No. NM_000539.3 and is incorporated herein as SEQ ID NO: 2. In certain embodiments, the human mutant P23H rhodopsin nucleic acid has a C to A substitution in codon 23 (exon 1) of a human rhodopsin gene having the sequence of GENBANK Accession No. NM_000539.3. In certain embodiments, the antisense compound is a single-stranded oligonucleotide.

Certain embodiments provide an antisense compound comprising a modified oligonucleotide consisting of 10 to 30 linked nucleosides and having a nucleobase sequence comprising at least 8 contiguous nucleobases of any of the nucleobase sequences of SEQ ID NOs: 11-64. In certain embodiments, the antisense compound is a single-stranded oligonucleotide.

Certain embodiments provide an antisense compound comprising a modified oligonucleotide consisting of 10 to 30 linked nucleosides and having a nucleobase sequence comprising at least 9 contiguous nucleobases of any of the nucleobase sequences of SEQ ID NOs: 11-64. In certain embodiments, the antisense compound is a single-stranded oligonucleotide.

Certain embodiments provide an antisense compound comprising a modified oligonucleotide consisting of 10 to 30 linked nucleosides and having a nucleobase sequence comprising at least 10 contiguous nucleobases of any of the nucleobase sequences of SEQ ID NOs: 11-64. In certain embodiments, the antisense compound is a single-stranded oligonucleotide.

Certain embodiments provide an antisense compound comprising a modified oligonucleotide consisting of 10 to 30 linked nucleosides and having a nucleobase sequence comprising at least 11 contiguous nucleobases of any of the nucleobase sequences of SEQ ID NOs: 11-64. In certain embodiments, the antisense compound is a single-stranded oligonucleotide.

Certain embodiments provide an antisense compound comprising a modified oligonucleotide consisting of 10 to 30 linked nucleosides and having a nucleobase sequence comprising at least 12 contiguous nucleobases of any of the nucleobase sequences of SEQ ID NOs: 11-64. In certain embodiments, the antisense compound is a single-stranded oligonucleotide.

Certain embodiments provide an antisense compound comprising a modified oligonucleotide consisting of 10 to 30 linked nucleosides and having a nucleobase sequence comprising the nucleobase sequence of any one of SEQ ID NOs: 11-64. In certain embodiments, the antisense compound is a single-stranded oligonucleotide.

Certain embodiments provide an antisense compound comprising a modified oligonucleotide consisting of the nucleobase sequence of any one of SEQ ID NOs: 11-64. In certain embodiments, the antisense compound is a single-stranded oligonucleotide.

In certain embodiments, a compound comprises or consists of a modified oligonucleotide consisting of 8 to 80 linked nucleosides having at least an 8, 9, 10, 11, 12, 13, 14, 15, or 16 contiguous nucleobase portion complementary to an equal length portion within nucleotides 157-174, 157-174, 157-171, 157-172, or 159-174 of SEQ ID NO: 2.

In certain embodiments, a compound comprises a modified oligonucleotide consisting of 8 to 80 linked nucleosides complementary within nucleotides 157-174, 157-171, 157-172, or 159-174 of SEQ ID NO: 2.

In certain embodiments, a compound comprises or consists of a modified oligonucleotide consisting of 10 to 30 linked nucleosides complementary within nucleotides 157-174, 157-174, 157-174, 157-171, 157-172, or 159-174 of SEQ ID NO: 2.

In certain embodiments, a compound comprises or consists of a modified oligonucleotide consisting of 8 to 80 linked nucleosides having a nucleobase sequence comprising at least an 8, 9, 10, 11, 12, 13, 14, 15, or 16 contiguous nucleobase portion any one of SEQ ID NOs: 15, 21, 29, or 64.

In certain embodiments, a compound comprises a modified oligonucleotide consisting of 10 to 30 linked nucleosides having a nucleobase sequence comprising at least 8 contiguous nucleobases of any one of SEQ ID NOs: 15, 21, 29, or 64.

In certain embodiments, a compound comprises a modified oligonucleotide consisting of 10 to 30 linked nucleosides having a nucleobase sequence comprising at least 9 contiguous nucleobases of any one of SEQ ID NOs: 15, 21, 29, or 64.

In certain embodiments, a compound comprises a modified oligonucleotide consisting of 10 to 30 linked nucleosides having a nucleobase sequence comprising at least 10 contiguous nucleobases of any one of SEQ ID NOs: 15, 21, 29, or 64.

In certain embodiments, a compound comprises a modified oligonucleotide consisting of 10 to 30 linked nucleosides having a nucleobase sequence comprising at least 11 contiguous nucleobases of any one of SEQ ID NOs: 15, 21, 29, or 64.

In certain embodiments, a compound comprises a modified oligonucleotide consisting of 10 to 30 linked nucleosides having a nucleobase sequence comprising at least 12 contiguous nucleobases of any one of SEQ ID NOs: 15, 21, 29, or 64.

In certain embodiments, a compound comprises or consists of a modified oligonucleotide consisting of 10 to 30 linked nucleosides having a nucleobase sequence comprising any one of SEQ ID NOs: 15, 21, 29, or 64.

In certain embodiments, a compound comprises or consists of a modified oligonucleotide having a nucleobase sequence consisting of any one of SEQ ID NOs: 15, 21, 29, or 64.

In certain embodiments, a modified oligonucleotide targeted to P23H rhodopsin is ISIS 564426, ISIS 664844, ISIS 664867, or ISIS 664884. Out of over 400 antisense oligonucleotides that were screened as described in the Examples section below, ISIS 564426, ISIS 664844, ISIS 664867, and ISIS 664884 emerged as the top lead compounds. In particular, ISIS 664844 exhibited the best combination of properties in terms of potency, tolerability, and selectivity for P23H rhodopsin out of over 400 antisense oligonucleotides.

In certain embodiments, any of the foregoing compounds or oligonucleotides comprises at least one modified internucleoside linkage, at least one modified sugar, and/or at least one modified nucleobase.

In certain embodiments, any of the foregoing compounds or oligonucleotides comprises at least one modified sugar. In certain embodiments, at least one modified sugar comprises a 2'-O-methoxyethyl group.

In certain embodiments, at least one modified sugar is a bicyclic sugar, such as a 4'-CH(CH$_3$)—O-2' group, a 4'-CH$_2$—O-2' group, or a 4'-(CH$_2$)$_2$—O-2' group.

In certain embodiments, the modified oligonucleotide comprises at least one modified internucleoside linkage, such as a phosphorothioate internucleoside linkage.

In certain embodiments, any of the foregoing compounds or oligonucleotides comprises at least one modified nucleobase, such as 5-methylcytosine.

In certain embodiments, any of the foregoing compounds or oligonucleotides comprises:
  a gap segment consisting of linked deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar. In certain embodiments, the oligonucleotide consists of 10 to 30 linked nucleosides having a nucleobase sequence comprising the sequence recited in SEQ ID NO: 15, 44, or 52.

In certain embodiments, a compound comprises or consists of a modified oligonucleotide consisting of 10 to 30 linked nucleosides having a nucleobase sequence comprising any one of SEQ ID NOs: 11-64, wherein the modified oligonucleotide comprises:
  a gap segment consisting of linked deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar.

In certain embodiments, a compound comprises or consists of a modified oligonucleotide consisting of 10 to 30 linked nucleosides having a nucleobase sequence comprising any one of SEQ ID NOs: 15, 21, 29, or 64, wherein the modified oligonucleotide comprises:
  a gap segment consisting of linked deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar.

In certain embodiments, a compound comprises or consists of a modified oligonucleotide consisting of 16 to 30 linked nucleosides having a nucleobase sequence comprising the sequence recited in SEQ ID NO: 15, wherein the modified oligonucleotide comprises:
  a gap segment consisting often linked deoxynucleosides;
  a 5' wing segment consisting of three linked nucleosides; and
  a 3' wing segment consisting of three linked nucleosides;
  wherein the gap segment is positioned between the 5' wing segment and the 3' wing segment; wherein each nucleoside of each wing segment comprises a cEt sugar; wherein each internucleoside linkage is a phosphorothioate linkage; and wherein each cytosine is a 5-methylcytosine.

In certain embodiments, a compound comprises or consists of a modified oligonucleotide consisting of 16 linked nucleosides having a nucleobase sequence consisting of the sequence recited in SEQ ID NO: 15, wherein the modified oligonucleotide comprises:
  a gap segment consisting often linked deoxynucleosides;
  a 5' wing segment consisting of three linked nucleosides; and
  a 3' wing segment consisting of three linked nucleosides;
  wherein the gap segment is positioned between the 5' wing segment and the 3' wing segment; wherein each nucleoside of each wing segment comprises a cEt sugar; wherein each internucleoside linkage is a phosphorothioate linkage; and wherein each cytosine is a 5-methylcytosine.

In certain embodiments, a compound comprises or consists of a modified oligonucleotide consisting of 16 to 30 linked nucleosides having a nucleobase sequence comprising the sequence recited in SEQ ID NO: 64, wherein the modified oligonucleotide comprises:
  a gap segment consisting of nine linked deoxynucleosides;
  a 5' wing segment consisting of four linked nucleosides; and
  a 3' wing segment consisting of three linked nucleosides;
  wherein the gap segment is positioned between the 5' wing segment and the 3' wing segment; wherein the 5' wing segment comprises a cEt sugar, a cEt sugar, a cEt sugar, and a 2'-flouro sugar in the 5' to 3' direction; wherein each nucleoside of the 3' wing segment comprises a cEt sugar; wherein each internucleoside linkage is a phosphorothioate linkage; and wherein each cytosine is a 5-methylcytosine.

In certain embodiments, a compound comprises or consists of a modified oligonucleotide consisting of 16 linked nucleosides having a nucleobase sequence consisting of the sequence recited in SEQ ID NO: 64, wherein the modified oligonucleotide comprises:
  a gap segment consisting of nine linked deoxynucleosides;
  a 5' wing segment consisting of four linked nucleosides; and
  a 3' wing segment consisting of three linked nucleosides;
  wherein the gap segment is positioned between the 5' wing segment and the 3' wing segment; wherein the 5' wing segment comprises a cEt sugar, a cEt sugar, a cEt sugar, and a 2'-flouro sugar in the 5' to 3' direction; wherein each nucleoside of the 3' wing segment comprises a cEt sugar; wherein each internucleoside linkage is a phosphorothioate linkage; and wherein each cytosine is a 5-methylcytosine.

In certain embodiments, a compound comprises or consists of a modified oligonucleotide consisting of 16 to 30 linked nucleosides having a nucleobase sequence comprising the sequence recited in SEQ ID NO: 21, wherein the modified oligonucleotide comprises:
  a gap segment consisting often linked deoxynucleosides;
  a 5' wing segment consisting of two linked nucleosides; and
  a 3' wing segment consisting of four linked nucleosides;
  wherein the gap segment is positioned between the 5' wing segment and the 3' wing segment; wherein each nucleoside of the 5' wing segment comprises a cEt sugar; wherein the 3' wing segment comprises a cEt sugar, a 2'-O-methoxyethyl sugar, a cEt sugar, and a 2'-O-methoxyethyl sugar in the 5' to 3' direction; wherein each internucleoside linkage is a phosphorothioate linkage; and wherein each cytosine is a 5-methylcytosine.

In certain embodiments, a compound comprises or consists of a modified oligonucleotide consisting of 16 linked nucleosides having a nucleobase sequence consisting of the sequence recited in SEQ ID NO: 21, wherein the modified oligonucleotide comprises:

a gap segment consisting of ten linked deoxynucleosides;
a 5' wing segment consisting of two linked nucleosides; and
a 3' wing segment consisting of four linked nucleosides;
wherein the gap segment is positioned between the 5' wing segment and the 3' wing segment; wherein each nucleoside of the 5' wing segment comprises a cEt sugar; wherein the 3' wing segment comprises a cEt sugar, a 2'-O-methoxyethyl sugar, a cEt sugar, and a 2'-O-methoxyethyl sugar in the 5' to 3' direction; wherein each internucleoside linkage is a phosphorothioate linkage; and wherein each cytosine is a 5-methylcytosine.

In certain embodiments, a compound comprises or consists of a modified oligonucleotide consisting of 15 to 30 linked nucleosides having a nucleobase sequence comprising the sequence recited in SEQ ID NO: 29, wherein the modified oligonucleotide comprises:

a gap segment consisting of ten linked deoxynucleosides;
a 5' wing segment consisting of two linked nucleosides; and
a 3' wing segment consisting of three linked nucleosides;
wherein the gap segment is positioned between the 5' wing segment and the 3' wing segment; wherein each nucleoside of the 5' wing segment comprises a cEt sugar; wherein the 3' wing segment comprises a cEt sugar, a 2'-O-methoxyethyl sugar, and a cEt sugar in the 5' to 3' direction; wherein each internucleoside linkage is a phosphorothioate linkage; and wherein each cytosine is a 5-methylcytosine.

In certain embodiments, a compound comprises or consists of a modified oligonucleotide consisting of 15 linked nucleosides having a nucleobase sequence consisting of the sequence recited in SEQ ID NO: 29, wherein the modified oligonucleotide comprises:

a gap segment consisting of ten linked deoxynucleosides;
a 5' wing segment consisting of two linked nucleosides; and
a 3' wing segment consisting of three linked nucleosides;
wherein the gap segment is positioned between the 5' wing segment and the 3' wing segment; wherein each nucleoside of the 5' wing segment comprises a cEt sugar; wherein the 3' wing segment comprises a cEt sugar, a 2'-O-methoxyethyl sugar, and a cEt sugar in the 5' to 3' direction; wherein each internucleoside linkage is a phosphorothioate linkage; and wherein each cytosine is a 5-methylcytosine.

In any of the foregoing embodiments, the compound or oligonucleotide can be at least 85%, at least 90%, at least 95%, at least 98%, at least 99%, or 100% complementary to a nucleic acid encoding P23H rhodopsin.

In any of the foregoing embodiments, the antisense compound can be a single-stranded oligonucleotide. In certain embodiments, the compound comprises deoxyribonucleotides.

In any of the foregoing embodiments, the antisense compound can be double-stranded. In certain embodiments, a compound comprises ribonucleotides.

In certain embodiments, compounds are capable of selectively targeting or inhibiting expression of the Rhodopsin P23H mutant allele. In certain embodiments, compounds have at least about a 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold selectivity for inhibiting expression of the Rhodopsin P23H mutant allele over the wild-type allele.

In certain embodiments, compounds or compositions provided herein comprise a salt of the modified oligonucleotide. In certain embodiments, the salt is a sodium salt. In certain embodiments, the salt is a potassium salt.

Certain embodiments provide a composition comprising the compound of any of the aforementioned embodiments or salt thereof and at least one of a pharmaceutically acceptable carrier or diluent. In certain embodiments, the composition has a viscosity less than about 40 centipoise (cP), less than about 30 centipose (cP), less than about 20 centipose (cP), less than about 15 centipose (cP), or less than about 10 centipose (cP). In certain embodiments, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain embodiments, the composition having any of the aforementioned viscosities and/or compound concentrations has a temperature of room temperature or about 20° C., about 21° C., about 22° C., about 23° C., about 24° C., about 25° C., about 26° C., about 27° C., about 28° C., about 29° C., or about 30° C.

Certain Indications

Certain embodiments provided herein relate to methods of treating, preventing, ameliorating, or slowing progression of a disease associated with P23H rhodopsin in a subject by administration of a P23H rhodopsin specific inhibitor, such as an antisense compound targeted to P23H rhodopsin. In certain embodiments, the inhibitor is allele-specific for P23H Rhodospin and selectively inhibits expression of P23H rhodopsin over wild-type rhodopsin. Examples of diseases associated with P23H rhodopsin treatable, preventable, and/or ameliorable with the methods provided herein include retinitis pigmentosa (RP), such as autosomal dominant retinitis pigmentosa (AdRP).

In certain embodiments, a method of treating, preventing, ameliorating, or slowing progression of retinitis pigmentosa (RP) or autosomal dominant retinitis pigmentosa (AdRP) in a subject comprises administering to the subject a P23H rhodopsin specific inhibitor, thereby treating, preventing, ameliorating, or slowing progression of retinitis pigmentosa (RP) or autosomal dominant retinitis pigmentosa (AdRP) in the subject. In certain embodiments, the P23H rhodopsin specific inhibitor is an antisense compound targeted to P23H rhodopsin, such as an antisense oligonucleotide targeted to P23H rhodopsin. In certain embodiments, the antisense compound is allele-specific for P23H Rhodospin and selectively inhibits expression of P23H rhodopsin over wild-type rhodopsin. In certain embodiments, the P23H rhodopsin specific inhibitor is a compound comprising or consisting of a modified oligonucleotide consisting of 8 to 80 linked nucleosides complementary within nucleotides 157-174, 157-171, 157-172, or 159-174 of SEQ ID NO: 2. In certain embodiments, the P23H rhodopsin specific inhibitor is a compound comprising or consisting of a modified oligonucleotide consisting of 10 to 30 linked nucleosides and having a nucleobase sequence comprising at least 8 contiguous nucleobases of any of the nucleobase sequences of SEQ ID NOs: 11-64. In certain embodiments, the P23H rhodopsin specific inhibitor is an antisense compound comprising or consisting of a modified oligonucleotide consisting of 10 to 30 nucleosides and having a nucleobase sequence comprising the nucleobase sequence of any one of SEQ ID NOs: 11-64. In certain embodiments, the P23H rhodopsin specific inhibitor is an antisense compound comprising or consisting of a modified oligonucleotide consisting of the nucleobase sequence of any one of SEQ ID NOs: 11-64. In certain embodiments, the P23H rhodopsin specific inhibitor is an antisense compound comprising or consisting of a modified oligonucleotide consisting of 10 to 30 linked nucleosides having a nucleobase sequence comprising at least 8, 9, 10, 11, or 12 contiguous nucleobases of any one of SEQ ID NOs: 15, 21, 29, or 64. In certain embodiments, the P23H rhodopsin specific inhibitor is an antisense compound comprising or consisting of a modified oligonucleotide consisting of 10 to 30 linked nucleosides having a nucleobase sequence comprising any one of SEQ ID NOs: 15, 21, 29, or 64. In certain embodiments, the P23H rhodopsin specific inhibitor is an antisense compound comprising or consisting of a modified oligonucleotide having a nucleobase sequence consisting of any one of SEQ ID NOs: 15, 21, 29, or 64. In certain embodiments, the P23H rhodopsin specific inhibitor is ISIS 564426, ISIS 664844, ISIS 664867, or ISIS 664884. In any of the foregoing embodiments, the antisense compound can be a single-stranded oligonucleotide. In certain embodiments, the antisense compound is administered to the subject by intravitreally such as by intravitreal injection. In certain embodiments, administering the antisense compound improves, preserves, or prevents worsening of visual function; visual field; photoreceptor cell function; electroretinogram (ERG) response such as full field ERG measuring retina wide function, dark adapted ERG measuring scotopic rod function, or light adapted ERG measuring photopic cone function; visual acuity; and/or vision-related quality of life. In certain embodiments, administering the antisense compound inhibits, prevents, or delays progression of photoreceptor cell loss and/or deterioration of the retina outer nuclear layer (ONL). In certain embodiments, the subject is identified as having the P23H rhodopsin mutant allele.

In certain embodiments, a method of inhibiting expression of P23H rhodopsin in a subject having a P23H rhodopsin mutant allele comprises administering a P23H rhodopsin specific inhibitor to the subject, thereby inhibiting expression of P23H rhodopsin in the subject. In certain embodiments, administering the inhibitor inhibits expression of P23H rhodopsin in the eye, retina, peripheral retina, rod photoreceptors, and/or cones. In certain embodiments, the subject has, or is at risk of having retinitis pigmentosa (RP), such as autosomal dominant retinitis pigmentosa (AdRP). In certain embodiments, the P23H rhodopsin specific inhibitor is an antisense compound allele-specific for P23H Rhodospin that selectively inhibits expression of P23H rhodopsin over wild-type rhodopsin. In certain embodiments, the P23H rhodopsin specific inhibitor is a compound comprising or consisting of a modified oligonucleotide consisting of 8 to 80 linked nucleosides complementary within nucleotides 157-174, 157-171, 157-172, or 159-174 of SEQ ID NO: 2. In certain embodiments, the P23H rhodopsin specific inhibitor is a compound comprising or consisting of a modified oligonucleotide consisting of 10 to 30 linked nucleosides and having a nucleobase sequence comprising at least 8 contiguous nucleobases of any of the nucleobase sequences of SEQ ID NOs: 11-64. In certain embodiments, the P23H rhodopsin specific inhibitor is an antisense compound comprising or consisting of a modified oligonucleotide consisting of 10 to 30 linked nucleosides and having a nucleobase sequence comprising the nucleobase sequence of any one of SEQ ID NOs: 11-64. In certain embodiments, the P23H rhodopsin specific inhibitor is an antisense compound comprising or consisting of a modified oligonucleotide consisting of the nucleobase sequence of any one of SEQ ID NOs: 11-64. In certain embodiments, the P23H rhodopsin specific inhibitor is an antisense compound comprising or consisting of a modified oligonucleotide consisting of 10 to 30 linked nucleosides having a nucleobase sequence comprising at least 8, 9, 10, 11, or 12 contiguous nucleobases of any one of SEQ ID NOs: 15, 21, 29, or 64. In certain embodiments, the P23H rhodopsin specific inhibitor is an antisense compound comprising or consisting of a modified oligonucleotide consisting of 10 to 30 linked nucleosides having a nucleobase sequence comprising any one of SEQ ID NOs: 15, 21, 29, or 64. In certain embodiments, the P23H rhodopsin specific inhibitor is an antisense compound comprising or consisting of a modified oligonucleotide having a nucleobase sequence consisting of any one of SEQ ID NOs: 15, 21, 29, or 64. In certain embodiments, the P23H rhodopsin specific inhibitor is ISIS 564426, ISIS 664844, ISIS 664867, or ISIS 664884. In any of the foregoing embodiments, the antisense compound can be a single-stranded oligonucleotide. In certain embodiments, the antisense compound is administered to the subject by intravitreally such as by intravitreal injection.

In certain embodiments, a method of improving or preserving visual function, visual field, photoreceptor cell function, ERG response, or visual acuity in a subject having a P23H rhodopsin mutant allele or having retinitis pigmentosa (RP), such as autosomal dominant retinitis pigmentosa (AdRP), comprises administering a P23H rhodopsin specific inhibitor to the subject. In certain embodiments, a method of inhibiting, preventing, or delaying progression of photoreceptor cell loss and/or deterioration of the retina outer nuclear layer (ONL) in a subject having a P23H rhodopsin mutant allele or having retinitis pigmentosa (RP), such as autosomal dominant retinitis pigmentosa (AdRP), comprises administering a P23H rhodopsin specific inhibitor to the subject. In certain embodiments, the inhibitor is an antisense compound targeted to P23H rhodopsin. In certain embodiments, the antisense compound is allele-specific for P23H Rhodospin and selectively inhibits expression of P23H rhodopsin over wild-type rhodopsin. In certain embodiments, the P23H rhodopsin specific inhibitor is a compound comprising or consisting of a modified oligonucleotide consisting of 8 to 80 linked nucleosides complementary within nucleotides 157-174, 157-171, 157-172, or 159-174 of SEQ ID NO: 2. In certain embodiments, the P23H rhodopsin specific inhibitor is a compound comprising or consisting of a modified oligonucleotide consisting of 10 to 30 linked nucleosides and having a nucleobase sequence comprising at least 8 contiguous nucleobases of any of the nucleobase sequences of SEQ ID NOs: 11-64. In certain embodiments, the P23H rhodopsin specific inhibitor is an antisense compound comprising or consisting of a modified oligonucleotide consisting of 10 to 30 linked nucleosides and having a nucleobase sequence comprising the nucleobase sequence of any one of SEQ ID NOs: 11-64. In certain embodiments, the P23H rhodopsin specific inhibitor is an antisense compound comprising or consisting of a modified oligonucleotide consisting of the nucleobase sequence of any one of SEQ ID NOs: 11-64. In certain embodiments, the P23H rhodopsin specific inhibitor is an antisense compound comprising or consisting of a modified oligonucleotide consisting of 10 to 30 linked nucleosides having a nucleobase sequence comprising at least 8, 9, 10, 11, or 12 contiguous nucleobases of any one of SEQ ID NOs: 15, 21, 29, or 64. In certain embodiments, the P23H rhodopsin specific inhibitor is an antisense compound comprising or consisting of a modified oligonucleotide consisting of 10 to 30 linked nucleosides having a nucleobase sequence comprising any one of SEQ ID NOs: 15, 21, 29, or 64. In certain embodiments, the P23H rhodopsin specific inhibitor is an antisense compound comprising or consisting of a modified oligonucleotide having a nucleobase sequence consisting of any one of SEQ ID NOs: 15, 21, 29, or 64. In certain embodiments, the P23H rhodopsin specific inhibitor is ISIS 564426, ISIS 664844, ISIS 664867, or ISIS 664884. In any of the foregoing embodiments, the antisense compound can be a single-stranded oligonucleotide. In certain embodiments, the antisense compound is administered to the subject by intravitreally such as by intravitreal injection.

In certain embodiments, a method of inhibiting expression of P23H rhodopsin in a cell comprises contacting the cell with a P23H rhodopsin specific inhibitor to the subject. In certain embodiments, the cell is a rod photoreceptor cell or cone cell. In certain embodiments, the cell is in the eye of a subject. In certain embodiments, the cell is in the retina of the eye. In certain embodiments, the inhibitor is an antisense compound targeted to P23H rhodopsin. In certain embodiments, the antisense compound is allele-specific for P23H Rhodospin and selectively inhibits expression of P23H rhodopsin over wild-type rhodopsin. In certain embodiments, the P23H rhodopsin specific inhibitor is a compound comprising or consisting of a modified oligonucleotide consisting of 8 to 80 linked nucleosides complementary within nucleotides 157-174, 157-171, 157-172, or 159-174 of SEQ ID NO: 2. In certain embodiments, the P23H rhodopsin specific inhibitor is a compound comprising or consisting of a modified oligonucleotide consisting of 10 to 30 linked nucleosides and having a nucleobase sequence comprising at least 8 contiguous nucleobases of any of the nucleobase sequences of SEQ ID NOs: 11-64. In certain embodiments, the P23H rhodopsin specific inhibitor is an antisense compound comprising or consisting of a modified oligonucleotide consisting of 10 to 30 linked nucleosides and having a nucleobase sequence comprising the nucleobase sequence of any one of SEQ ID NOs: 11-64. In certain embodiments, the P23H rhodopsin specific inhibitor is an antisense compound comprising or consisting of a modified oligonucleotide consisting of the nucleobase sequence of any one of SEQ ID NOs: 11-64. In certain embodiments, the P23H rhodopsin specific inhibitor is an antisense compound comprising or consisting of a modified oligonucleotide consisting of 10 to 30 linked nucleosides having a nucleobase sequence comprising at least 8, 9, 10, 11, or 12 contiguous nucleobases of any one of SEQ ID NOs: 15, 21, 29, or 64. In certain embodiments, the P23H rhodopsin specific inhibitor is an antisense compound comprising or consisting of a modified oligonucleotide consisting of 10 to 30 linked nucleosides having a nucleobase sequence comprising any one of SEQ ID NOs: 15, 21, 29, or 64. In certain embodiments, the P23H rhodopsin specific inhibitor is an antisense compound comprising or consisting of a modified oligonucleotide having a nucleobase sequence consisting of any one of SEQ ID NOs: 15, 21, 29, or 64. In certain embodiments, the P23H rhodopsin specific inhibitor is ISIS 564426, ISIS 664844, ISIS 664867, or ISIS 664884. In any of the foregoing embodiments, the antisense compound can be a single-stranded oligonucleotide.

Certain embodiments are drawn to a P23H rhodopsin specific inhibitor for use in treating retinitis pigmentosa (RP), such as autosomal dominant retinitis pigmentosa (AdRP) associated with P23H rhodopsin. In certain embodiments, the inhibitor is an antisense compound targeted to P23H rhodopsin. In certain embodiments, the antisense compound is allele-specific for P23H Rhodospin and selectively inhibits expression of P23H rhodopsin over wild-type rhodopsin. In certain embodiments, the P23H rhodopsin specific inhibitor is a compound comprising or consisting of a modified oligonucleotide consisting of 8 to 80 linked nucleosides complementary within nucleotides 157-174, 157-171, 157-172, or 159-174 of SEQ ID NO: 2. In certain embodiments, the P23H rhodopsin specific inhibitor is a compound comprising or consisting of a modified oligonucleotide consisting of 10 to 30 linked nucleosides and having a nucleobase sequence comprising at least 8 contiguous nucleobases of any of the nucleobase sequences of SEQ ID NOs: 11-64. In certain embodiments, the P23H rhodopsin specific inhibitor is an antisense compound comprising or consisting of a modified oligonucleotide consisting of 10 to 30 linked nucleosides and having a nucleobase sequence comprising the nucleobase sequence of any one of SEQ ID NOs: 11-64. In certain embodiments, the P23H rhodopsin specific inhibitor is an antisense compound comprising or consisting of a modified oligonucleotide consisting of the nucleobase sequence of any one of SEQ ID NOs: 11-64. In certain embodiments, the P23H rhodopsin specific inhibitor is an antisense compound comprising or consisting of a modified oligonucleotide consisting of 10 to 30 linked nucleosides having a nucleobase sequence comprising any one of SEQ ID NOs: 15, 21, 29, or 64. In certain embodiments, the P23H rhodopsin specific inhibitor is an antisense compound comprising or consisting of a modified oligonucleotide having a nucleobase sequence consisting of any one of SEQ ID NOs: 15, 21, 29, or 64. In certain embodiments, the P23H rhodopsin specific inhibitor is ISIS 564426, ISIS 664844, ISIS 664867, or ISIS 664884. In any of the foregoing embodiments, the antisense compound can be a single-stranded oligonucleotide.

Certain embodiments are drawn to a P23H rhodopsin specific inhibitor for use in improving or preserving visual function, visual field, photoreceptor cell function, ERG response, visual acuity, and/or vision-related quality of life of a subject having retinitis pigmentosa (RP), such as autosomal dominant retinitis pigmentosa (AdRP) associated with P23H rhodopsin. Certain embodiments are drawn to a P23H rhodopsin specific inhibitor for use in inhibiting, preventing, or delaying progression of photoreceptor cell loss and/or deterioration of the retina outer nuclear layer (ONL) in a subject having retinitis pigmentosa (RP), such as autosomal dominant retinitis pigmentosa (AdRP) associated with P23H rhodopsin. In certain embodiments, the P23H rhodopsin specific inhibitor is a compound comprising or consisting of a modified oligonucleotide consisting of 8 to 80 linked nucleosides complementary within nucleotides 157-174, 157-171, 157-172, or 159-174 of SEQ ID NO: 2. In certain embodiments, the P23H rhodopsin specific inhibitor is a compound comprising or consisting of a modified oligonucleotide consisting of 10 to 30 linked nucleosides and having a nucleobase sequence comprising at least 8 contiguous nucleobases of any of the nucleobase sequences of SEQ ID NOs: 11-64. In certain embodiments, the P23H rhodopsin specific inhibitor is an antisense compound comprising or consisting of a modified oligonucleotide consisting of 10 to 30 linked nucleosides and having a nucleobase sequence comprising the nucleobase sequence of any one of SEQ ID NOs: 11-64. In certain embodiments, the P23H rhodopsin specific inhibitor is an antisense compound comprising or consisting of a modified oligonucleotide consisting of the nucleobase sequence of any one of SEQ ID NOs: 11-64. In certain embodiments, the P23H rhodopsin specific inhibitor is an antisense compound comprising or consisting of a modified oligonucleotide consisting of 10 to 30 linked nucleosides having a nucleobase sequence comprising at least 8, 9, 10, 11, or 12 contiguous nucleobases of any one of SEQ ID NOs: 15, 21, 29, or 64. In certain embodiments, the P23H rhodopsin specific inhibitor is an antisense compound comprising or consisting of a modified oligonucleotide consisting of 10 to 30 linked nucleosides having a nucleobase sequence comprising any one of SEQ ID NOs: 15, 21, 29, or 64. In certain embodiments, the P23H rhodopsin specific inhibitor is an antisense compound comprising or consisting of a modified oligonucleotide having a nucleobase sequence consisting of any one of SEQ ID NOs: 15, 21, 29, or 64. In certain embodiments, the P23H rhodopsin specific inhibitor is ISIS 564426, ISIS 664844, ISIS 664867, or ISIS 664884. In any of the foregoing embodiments, the antisense compound can be a single-stranded oligonucleotide.

Certain embodiments are drawn to use of a P23H rhodopsin specific inhibitor for the manufacture of a medicament for treating retinitis pigmentosa (RP), such as autosomal dominant retinitis pigmentosa (AdRP) associated with P23H rhodopsin. In certain embodiments, the inhibitor is an antisense compound targeted to P23H rhodopsin. In certain embodiments, the antisense compound is allele-specific for P23H Rhodospin and selectively inhibits expression of P23H rhodopsin over wild-type rhodopsin. In certain embodiments, the P23H rhodopsin specific inhibitor is a compound comprising or consisting of a modified oligonucleotide consisting of 8 to 80 linked nucleosides complementary within nucleotides 157-174, 157-171, 157-172, or 159-174 of SEQ ID NO: 2. In certain embodiments, the P23H rhodopsin specific inhibitor is a compound comprising or consisting of a modified oligonucleotide consisting of 10 to 30 linked nucleosides and having a nucleobase sequence comprising at least 8 contiguous nucleobases of any of the nucleobase sequences of SEQ ID NOs: 11-64. In certain embodiments, the P23H rhodopsin specific inhibitor is an antisense compound comprising or consisting of a modified oligonucleotide consisting of 10 to 30 linked nucleosides and having a nucleobase sequence comprising the nucleobase sequence of any one of SEQ ID NOs: 11-64. In certain embodiments, the P23H rhodopsin specific inhibitor is an antisense compound comprising or consisting of a modified oligonucleotide consisting of the nucleobase sequence of any one of SEQ ID NOs: 11-64. In certain embodiments, the P23H rhodopsin specific inhibitor is an antisense compound comprising or consisting of a modified oligonucleotide consisting of 10 to 30 linked nucleosides having a nucleobase sequence comprising at least 8, 9, 10, 11, or 12 contiguous nucleobases of any one of SEQ ID NOs: 15, 21, 29, or 64. In certain embodiments, the P23H rhodopsin specific inhibitor is an antisense compound comprising or consisting of a modified oligonucleotide consisting of 10 to 30 linked nucleosides having a nucleobase sequence comprising any one of SEQ ID NOs: 15, 21, 29, or 64. In certain embodiments, the P23H rhodopsin specific inhibitor is an antisense compound comprising or consisting of a modified oligonucleotide having a nucleobase sequence consisting of any one of SEQ ID NOs: 15, 21, 29, or 64. In certain embodiments, the P23H rhodopsin specific inhibitor is ISIS 564426, ISIS 664844, ISIS 664867, or ISIS 664884. In any of the foregoing embodiments, the antisense compound can be a single-stranded oligonucleotide.

In any of the foregoing embodiments, the antisense compound can be a single-stranded oligonucleotide.

Certain embodiments are drawn to use of a P23H rhodopsin specific inhibitor for the manufacture of a medicament for improving or preserving visual function, visual field, photoreceptor cell function, ERG response, visual acuity, and/or vision-related quality of life of a subject having retinitis pigmentosa (RP), such as autosomal dominant retinitis pigmentosa (AdRP) associated with P23H rhodopsin. Certain embodiments are drawn to use of a P23H rhodopsin specific inhibitor for the manufacture of a medicament for inhibiting, preventing, or delaying progression of photoreceptor cell loss and/or deterioration of the retina outer nuclear layer (ONL) in a subject having retinitis pigmentosa (RP), such as autosomal dominant retinitis pigmentosa (AdRP) associated with P23H rhodopsin. In certain embodiments, the inhibitor is an antisense compound targeted to P23H rhodopsin. In certain embodiments, the antisense compound is allele-specific for P23H Rhodospin and selectively inhibits expression of P23H rhodopsin over wild-type rhodopsin. In certain embodiments, the P23H rhodopsin specific inhibitor is a compound comprising or consisting of a modified oligonucleotide consisting of 8 to 80 linked nucleosides complementary within nucleotides 157-174, 157-171, 157-172, or 159-174 of SEQ ID NO: 2. In certain embodiments, the P23H rhodopsin specific inhibitor is a compound comprising or consisting of a modified oligonucleotide consisting of 10 to 30 linked nucleosides and having a nucleobase sequence comprising at least 8 contiguous nucleobases of any of the nucleobase sequences of SEQ ID NOs: 11-64. In certain embodiments, the P23H rhodopsin specific inhibitor is an antisense compound comprising or consisting of a modified oligonucleotide consisting of 10 to 30 linked nucleosides and having a nucleobase sequence comprising the nucleobase sequence of any one of SEQ ID NOs: 11-64. In certain embodiments, the P23H rhodopsin specific inhibitor is an antisense compound comprising or consisting of a modified oligonucleotide consisting of the nucleobase sequence of any one of SEQ ID NOs: 11-64. In certain embodiments, the P23H rhodopsin specific inhibitor is an antisense compound comprising or consisting of a modified oligonucleotide consisting of 10 to 30 linked nucleosides having a nucleobase sequence comprising at least 8, 9, 10, 11, or 12 contiguous nucleobases of any one of SEQ ID NOs: 15, 21, 29, or 64. In certain embodiments, the P23H rhodopsin specific inhibitor is an antisense compound comprising or consisting of a modified oligonucleotide consisting of 10 to 30 linked nucleosides having a nucleobase sequence comprising any one of SEQ ID NOs: 15, 21, 29, or 64. In certain embodiments, the P23H rhodopsin specific inhibitor is an antisense compound comprising or consisting of a modified oligonucleotide having a nucleobase sequence consisting of any one of SEQ ID NOs: 15, 21, 29, or 64. In certain embodiments, the P23H rhodopsin specific inhibitor is ISIS 564426, ISIS 664844, ISIS 664867, or ISIS 664884. In any of the foregoing embodiments, the antisense compound can be a single-stranded oligonucleotide.

In any of the foregoing methods or uses, the P23H rhodopsin specific inhibitor can be an antisense compound targeted to P23H rhodopsin. In certain embodiments, the antisense compound is an antisense oligonucleotide, for example an antisense oligonucleotide consisting of 8 to 80 linked nucleosides, 12 to 30 linked nucleosides, or 20 linked nucleosides. In certain embodiments, the antisense oligonucleotide is at least 80%, 85%, 90%, 95% or 100% complementary to any of the nucleobase sequences recited in SEQ ID NOs: 1-4. In certain embodiments, the antisense oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar. In certain embodiments, the antisense oligonucleotide is allele-specific for P23H Rhodospin and selectively inhibits expression of P23H rhodopsin over wild-type rhodopsin.

In any of the foregoing methods or uses, the P23H rhodopsin specific inhibitor can be a compound comprising or consisting of a modified oligonucleotide consisting of 10 to 30 linked nucleosides having a nucleobase sequence comprising any one of SEQ ID NOs: 11-64, wherein the modified oligonucleotide comprises:
  a gap segment consisting of linked deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar.

In any of the foregoing methods or uses, the P23H rhodopsin specific inhibitor can be a compound comprising or consisting of a modified oligonucleotide consisting of 10 to 30 linked nucleosides having a nucleobase sequence comprising any one of SEQ ID NOs: 15, 21, 29, or 64, wherein the modified oligonucleotide comprises:
  a gap segment consisting of linked deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar.

In any of the foregoing methods or uses, the P23H rhodopsin specific inhibitor can be a compound comprising or consisting of a modified oligonucleotide consisting of 16 to 30 linked nucleosides having a nucleobase sequence comprising the sequence recited in SEQ ID NO: 15, wherein the modified oligonucleotide comprises:
  a gap segment consisting of ten linked deoxynucleosides;
  a 5' wing segment consisting of three linked nucleosides; and
  a 3' wing segment consisting of three linked nucleosides;
  wherein the gap segment is positioned between the 5' wing segment and the 3' wing segment; wherein each nucleoside of each wing segment comprises a cEt sugar; wherein each internucleoside linkage is a phosphorothioate linkage; and wherein each cytosine is a 5-methylcytosine.

In any of the foregoing methods or uses, the P23H rhodopsin specific inhibitor can be a compound comprising or consisting of a modified oligonucleotide consisting of 16 linked nucleosides having a nucleobase sequence consisting of the sequence recited in SEQ ID NO: 15, wherein the modified oligonucleotide comprises:
  a gap segment consisting often linked deoxynucleosides;
  a 5' wing segment consisting of three linked nucleosides; and
  a 3' wing segment consisting of three linked nucleosides;
  wherein the gap segment is positioned between the 5' wing segment and the 3' wing segment; wherein each nucleoside of each wing segment comprises a cEt sugar; wherein each internucleoside linkage is a phosphorothioate linkage; and wherein each cytosine is a 5-methylcytosine.

In any of the foregoing methods or uses, the P23H rhodopsin specific inhibitor can be a compound comprising or consisting of a modified oligonucleotide consisting of 16 to 30 linked nucleosides having a nucleobase sequence comprising the sequence recited in SEQ ID NO: 64, wherein the modified oligonucleotide comprises:
  a gap segment consisting of nine linked deoxynucleosides;
  a 5' wing segment consisting of four linked nucleosides; and
  a 3' wing segment consisting of three linked nucleosides;
  wherein the gap segment is positioned between the 5' wing segment and the 3' wing segment; wherein the 5' wing segment comprises a cEt sugar, a cEt sugar, a cEt sugar, and a 2'-flouro sugar in the 5' to 3' direction; wherein each nucleoside of the 3' wing segment comprises a cEt sugar; wherein each internucleoside linkage is a phosphorothioate linkage; and wherein each cytosine is a 5-methylcytosine.

In any of the foregoing methods or uses, the P23H rhodopsin specific inhibitor can be a compound comprising or consisting of a modified oligonucleotide consisting of 16 linked nucleosides having a nucleobase sequence consisting of the sequence recited in SEQ ID NO: 64, wherein the modified oligonucleotide comprises:
  a gap segment consisting of nine linked deoxynucleosides;
  a 5' wing segment consisting of four linked nucleosides; and
  a 3' wing segment consisting of three linked nucleosides;
  wherein the gap segment is positioned between the 5' wing segment and the 3' wing segment; wherein the 5' wing segment comprises a cEt sugar, a cEt sugar, a cEt sugar, and a 2'-flouro sugar in the 5' to 3' direction; wherein each nucleoside of the 3' wing segment comprises a cEt sugar; wherein each internucleoside linkage is a phosphorothioate linkage; and wherein each cytosine is a 5-methylcytosine.

In any of the foregoing methods or uses, the P23H rhodopsin specific inhibitor can be a compound comprising or consisting of a modified oligonucleotide consisting of 16 to 30 linked nucleosides having a nucleobase sequence comprising the sequence recited in SEQ ID NO: 21, wherein the modified oligonucleotide comprises:
  a gap segment consisting often linked deoxynucleosides;
  a 5' wing segment consisting of two linked nucleosides; and
  a 3' wing segment consisting of four linked nucleosides;
  wherein the gap segment is positioned between the 5' wing segment and the 3' wing segment; wherein each nucleoside of the 5' wing segment comprises a cEt sugar; wherein the 3' wing segment comprises a cEt sugar, a 2'-O-methoxyethyl sugar, a cEt sugar, and a 2'-O-methoxyethyl sugar in the 5' to 3' direction; wherein each internucleoside linkage is a phosphorothioate linkage; and wherein each cytosine is a 5-methylcytosine.

In any of the foregoing methods or uses, the P23H rhodopsin specific inhibitor can be a compound comprising or consisting of a modified oligonucleotide consisting of 16 linked nucleosides having a nucleobase sequence consisting of the sequence recited in SEQ ID NO: 21, wherein the modified oligonucleotide comprises:

a gap segment consisting often linked deoxynucleosides;

a 5' wing segment consisting of two linked nucleosides; and a 3' wing segment consisting of four linked nucleosides;

wherein the gap segment is positioned between the 5' wing segment and the 3' wing segment; wherein each nucleoside of the 5' wing segment comprises a cEt sugar; wherein the 3' wing segment comprises a cEt sugar, a 2'-O-methoxyethyl sugar, a cEt sugar, and a 2'-O-methoxyethyl sugar in the 5' to 3' direction; wherein each internucleoside linkage is a phosphorothioate linkage; and wherein each cytosine is a 5-methylcytosine.

In any of the foregoing methods or uses, the P23H rhodopsin specific inhibitor can be a compound comprising or consisting of a modified oligonucleotide consisting of 15 to 30 linked nucleosides having a nucleobase sequence comprising the sequence recited in SEQ ID NO: 29, wherein the modified oligonucleotide comprises:

a gap segment consisting often linked deoxynucleosides;

a 5' wing segment consisting of two linked nucleosides; and a 3' wing segment consisting of three linked nucleosides;

wherein the gap segment is positioned between the 5' wing segment and the 3' wing segment; wherein each nucleoside of the 5' wing segment comprises a cEt sugar; wherein the 3' wing segment comprises a cEt sugar, a 2'-O-methoxyethyl sugar, and a cEt sugar in the 5' to 3' direction; wherein each internucleoside linkage is a phosphorothioate linkage; and wherein each cytosine is a 5-methylcytosine.

In any of the foregoing methods or uses, the P23H rhodopsin specific inhibitor can be a compound comprising or consisting of a modified oligonucleotide consisting of 15 linked nucleosides having a nucleobase sequence consisting of the sequence recited in SEQ ID NO: 29, wherein the modified oligonucleotide comprises:

a gap segment consisting often linked deoxynucleosides;

a 5' wing segment consisting of two linked nucleosides; and a 3' wing segment consisting of three linked nucleosides;

wherein the gap segment is positioned between the 5' wing segment and the 3' wing segment; wherein each nucleoside of the 5' wing segment comprises a cEt sugar; wherein the 3' wing segment comprises a cEt sugar, a 2'-O-methoxyethyl sugar, and a cEt sugar in the 5' to 3' direction; wherein each internucleoside linkage is a phosphorothioate linkage; and wherein each cytosine is a 5-methylcytosine.

In any of the foregoing methods or uses, the P23H rhodopsin specific inhibitor is administered intravitreally, such as by intravitreal injection.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted.

In certain embodiments, an antisense compound is 10 to 30 subunits in length. In certain embodiments, an antisense compound is 12 to 30 subunits in length. In certain embodiments, an antisense compound is 12 to 22 subunits in length. In certain embodiments, an antisense compound is 14 to 30 subunits in length. In certain embodiments, an antisense compound is 14 to 20 subunits in length. In certain embodiments, an antisense compound is 15 to 30 subunits in length. In certain embodiments, an antisense compound is 15 to 20 subunits in length. In certain embodiments, an antisense compound is 16 to 30 subunits in length. In certain embodiments, an antisense compound is 16 to 20 subunits in length. In certain embodiments, an antisense compound is 17 to 30 subunits in length. In certain embodiments, an antisense compound is 17 to 20 subunits in length. In certain embodiments, an antisense compound is 18 to 30 subunits in length. In certain embodiments, an antisense compound is 18 to 21 subunits in length. In certain embodiments, an antisense compound is 18 to 20 subunits in length. In certain embodiments, an antisense compound is 20 to 30 subunits in length. In other words, such antisense compounds are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, an antisense compound is 14 subunits in length. In certain embodiments, an antisense compound is 16 subunits in length. In certain embodiments, an antisense compound is 17 subunits in length. In certain embodiments, an antisense compound is 18 subunits in length. In certain embodiments, an antisense compound is 19 subunits in length. In certain embodiments, an antisense compound is 20 subunits in length. In other embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments antisense oligonucleotides may be shortened or truncated. For example, a single subunit may be deleted from the 5' end (5' truncation), or alternatively from the 3' end (3' truncation). A shortened or truncated antisense compound targeted to an P23H rhodopsin nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al. (*J Natl. Cancer Inst.* 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (*Nuc. Acid. Res.* 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include 3-D-ribonucleosides, P3-D-deoxyribonucleosides, 2'-modified nucleosides (such 2'-modified nucleosides may include 2'-MOE and 2'-O—$CH_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to a P23H rhodopsin nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: $(J)_m(B)_n(J)_p\text{-}(B)_r\text{-}(A)_t\text{-}(D)_g\text{-}(A)_v\text{-}(B)_w\text{-}(J)_x\text{-}(B)_y\text{-}(J)_z$
wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14; provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

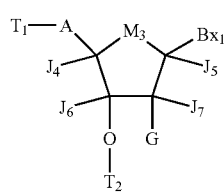

wherein:
$T_1$ is an optionally protected phosphorus moiety;
$T_2$ is an internucleoside linking group linking the compound of Formula IIc to the oligomeric compound;
A has one of the formulas:

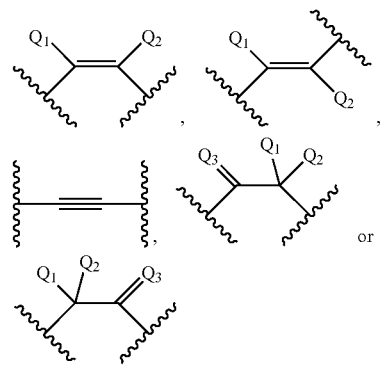

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;
$Q_3$ is O, S, $N(R_5)$ or $C(R_6)(R_7)$;
each $R_3$, $R_4$, $R_5$, $R_6$ and $R_7$ is, independently, H, $C_1$-$C_6$ alkyl, substituted $C_1$-$C_6$ alkyl or $C_1$-$C_6$ alkoxy;
$M_3$ is O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$ or $OC(R_{15})(Bx_2)$;
$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$Bx_1$ is a heterocyclic base moiety;
or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
G is H, OH, halogen or $O-[C(R_8)(R_9)]_n-[(C=O)_m-X_1]_j-Z$;
each $R_8$ and $R_9$ is, independently, H, halogen, $C_1$-$C_6$ alkyl or substituted $C_1$-$C_6$ alkyl;
$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

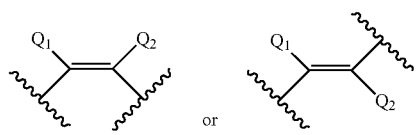

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

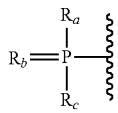

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$, are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_1)$, $O(CH_2)_2$—$O(CH_2)_2$—$N(R_{10})(R_1)$, $OCH_2C(=O)$—$N(R_{10})(R_1)$, $OCHC(=O)$—$N(R_{12})$—$(CH_2)_2$—$N(R_{10})(R_{11})$ or $O(CH_2)_2$—$N(R_{12})$—$C(=NR_3)[N(R_0)(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C$ $(=O)$—$N(H)$—$(CH_2)_2$—$N(CH_3)_2$ or $OCH_2$—$N(H)$—$C(=NH)NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

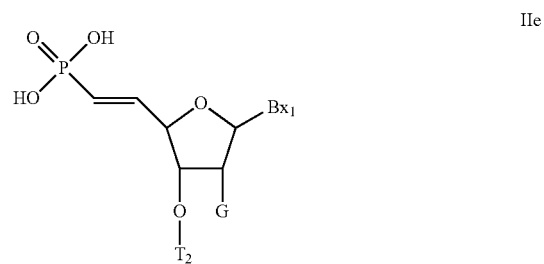

IIe

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;
ABBABB;
AABAAB;
ABBABAABB;
ABABAA;

AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

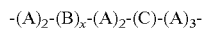
-(A)$_2$-(B)$_x$-(A)$_2$-(C)-(A)$_3$- wherein: A is a first type of modified nucleoside;
B and C, are nucleosides that are differently modified than A, however, B and C may have the same or different modifications as one another;
x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif: 5'-(Q)-(AB)$_x$A$_y$-(D)$_z$
wherein:
Q is a nucleoside comprising a stabilized phosphate moiety. In certain embodiments, Q is a nucleoside having Formula IIc or IIe;
A is a first type of modified nucleoside;
B is a second type of modified nucleoside;
D is a modified nucleoside comprising a modification different from the nucleoside adjacent to it. Thus, if y is 0, then D must be differently modified than B and if y is 1, then D must be differently modified than A. In certain embodiments, D differs from both A and B.
X is 5-15;
Y is 0 or 1;
Z is 0-4.

In certain embodiments, oligonucleosides have the following sugar motif:
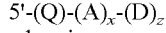
5'-(Q)-(A)$_x$-(D)$_z$
wherein:
Q is a nucleoside comprising a stabilized phosphate moiety. In certain embodiments, Q is a nucleoside having Formula IIc or IIe;
A is a first type of modified nucleoside;
D is a modified nucleoside comprising a modification different from A.
X is 11-30;
Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region    | 3'-region |
|-----------------|-------------------|-----------|
| PS              | Alternating PO/PS | 6 PS      |
| PS              | Alternating PO/PS | 7 PS      |
| PS              | Alternating PO/PS | 8 PS      | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In certain embodiments, the degradation of the targeted P23H rhodopsin is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfill a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676;

Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target P23H rhodopsin by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode wild-type rhodopsin, without limitation, genomic sequence having the sequence set forth in GENBANK Accession No. NT_005612.16 truncated from nucleotides 35737800 to 35755500 (incorporated herein as SEQ ID NO: 1) and coding sequence having the sequence set forth in GENBANK Accession No NM_000539.3 (incorporated herein as SEQ ID NO: 3). Nucleotide sequences that encode mutant P23H rhodopsin nucleic acid have a C to A mutation at nucleotide 163 of GENBANK Accession No NM_000539.3 and is incorporated herein as SEQ ID NO: 2.

Hybridization

In some embodiments, hybridization occurs between an antisense compound disclosed herein and a P23H rhodopsin nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a P23H rhodopsin nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a P23H rhodopsin nucleic acid).

Non-complementary nucleobases between an antisense compound and a P23H rhodopsin nucleic acid may be tolerated provided that the antisense compound remains able to specifically hybridize to a target nucleic acid. Moreover, an antisense compound may hybridize over one or more segments of a P23H rhodopsin nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a P23H rhodopsin nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J Mol. Biol.,* 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.,* 1981, 2, 482 489).

In certain embodiments, the antisense compounds provided herein, or specified portions thereof, are fully complementary (i.e. 100% complementary) to a target nucleic acid, or specified portion thereof. For example, an antisense compound may be fully complementary to a P23H rhodopsin nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a P23H rhodopsin nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a P23H rhodopsin nucleic acid, or specified portion thereof.

The antisense compounds provided also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds are complementary to at least an 11 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are, or are at least, 70%, 75%, 80%, 85%, 90%, 91%, 92%, 93%, 94%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a P23H rhodopsin nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein 4'-$(CH_2)$—O-2' (LNA) is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—$C(=O)$—$N(R_m)(R_n)$, and O—$CH_2$—$C(=O)$—$N(R)$—$(CH_2)_2$—$N(R_m)(R_n)$, where each $R_j$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' (also referred to as constrained ethyl or cEt) and 4'-CH (CH₂OCH₃)—O-2' (and analogs thereof see U.S. Pat. No. 7,399,845, issued on Jul. 15, 2008); 4'-C(CH₃)(CH₃)—O-2' (and analogs thereof see published International Application WO/2009/006478, published Jan. 8, 2009); 4'-CH₂—N(OCH₃)-2' (and analogs thereof see published International Application WO/2008/150729, published Dec. 11, 2008); 4'-CH₂—O—N(CH₃)-2' (see published U.S. Patent Application US2004-0171570, published Sep. 2, 2004); 4'-CH₂—N(R)—O-2', wherein R is H, C₁-C₁₂ alkyl, or a protecting group (see U.S. Pat. No. 7,427,672, issued on Sep. 23, 2008); 4'-CH₂—C(H)(CH₃)-2' (see Chattopadhyaya et al., *J. Org. Chem.*, 2009, 74, 118-134); and 4'-CH₂—C(=CH₂)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. No. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and 3-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)₂—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C₁-C₁₂ alkyl, substituted C₁-C₁₂ alkyl, C₂-C₁₂ alkenyl, substituted C₂-C₁₂ alkenyl, C₂-C₁₂ alkynyl, substituted C₂-C₁₂ alkynyl, C₅-C₂₀ aryl, substituted C₅-C₂₀ aryl, heterocycle radical, substituted heterocycle radical, heteroaryl, substituted heteroaryl, C₅-C₇ alicyclic radical, substituted C₅-C₇ alicyclic radical, halogen, OJ₁, NJ₁J₂, SJ₁, N₃, COOJ₁, acyl (C(=O)—H), substituted acyl, CN, sulfonyl (S(=O)₂-J₁), or sulfoxyl (S(=O)-J₁); and each J₁ and J₂ is, independently, H, C₁-C₁₂ alkyl, substituted C₁-C₁₂ alkyl, C₂-C₁₂ alkenyl, substituted C₂-C₁₂ alkenyl, C₂-C₁₂ alkynyl, substituted C₂-C₁₂ alkynyl, C₅-C₂₀ aryl, substituted C₅-C₂₀ aryl, acyl (C(=O)—H), substituted acyl, a heterocycle radical, a substituted heterocycle radical, C₁-C₁₂ aminoalkyl, substituted C₁-C₁₂ aminoalkyl or a protecting group.

In certain embodiments, the bridge of a bicyclic sugar moiety is —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH₂-2', 4'-(CH₂)₂-2', 4'-(CH₂)₃-2', 4'-CH₂—O-2', 4'-(CH₂)₂—O-2', 4'-CH₂—O—N(R)-2' and 4'-CH₂—N(R)—O-2'- wherein each R is, independently, H, a protecting group or C₁-C₁₂ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH₂—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH₂—O-2') BNA, (B) 3-D-methyleneoxy (4'-CH₂—O-2') BNA, (C) ethyleneoxy (4'-(CH₂)₂—O-2') BNA, (D) aminooxy (4'-CH₂—O—N(R)-2') BNA, (E) oxyamino (4'-CH₂—N(R)—O-2') BNA, and (F) methyl(methyleneoxy) (4'-CH(CH₃)—O-2') BNA, (G) methylene-thio (4'-CH₂—S-2') BNA, (H) methylene-amino (4'-CH₂—N(R)-2') BNA, (I) methyl carbocyclic (4'-CH₂—CH(CH₃)-2') BNA, (J) propylene carbocyclic (4'-(CH₂)₃-2') BNA and (K) vinyl BNA as depicted below:

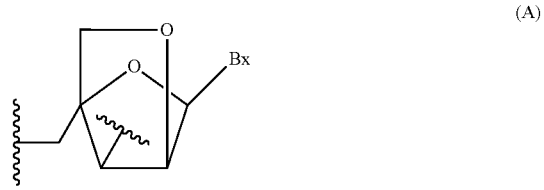

(A)

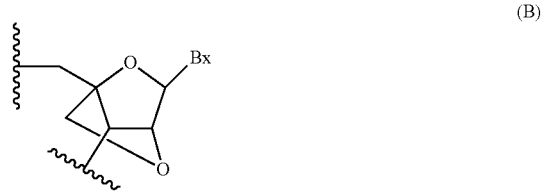

(B)

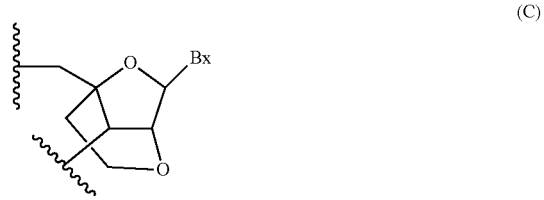

(C)

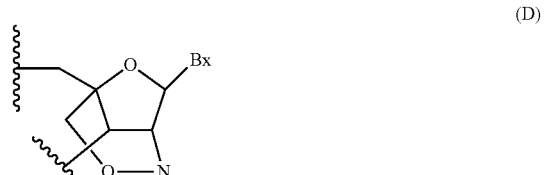

(D)

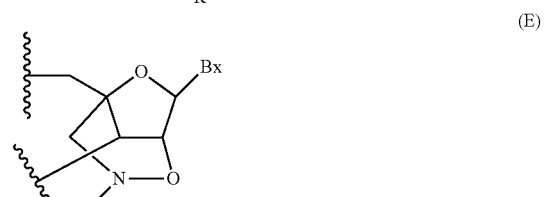

(E)

(F) 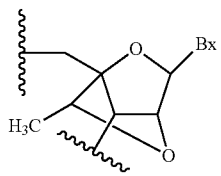

(G) 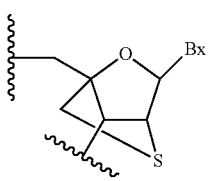

(H) 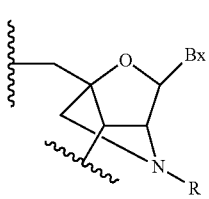

(I) 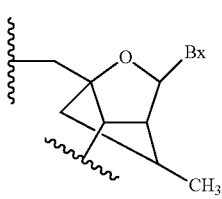

(J) 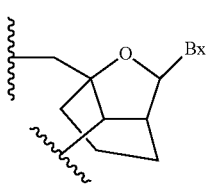

(K) 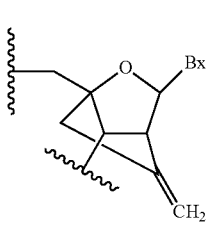

wherein Bx is the base moiety and R is independently H, a protecting group, $C_1$-$C_{12}$ alkyl or $C_1$-$C_{12}$ alkoxy.

In certain embodiments, bicyclic nucleosides are provided having Formula I:

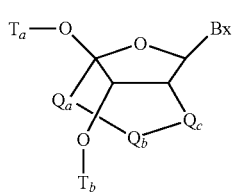

wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

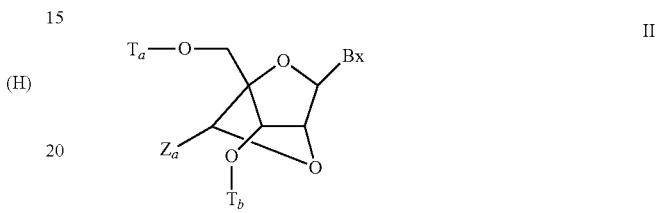

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

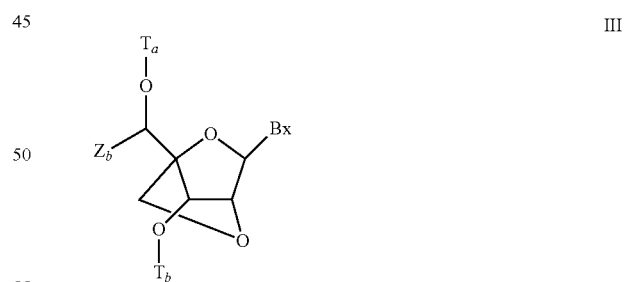

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

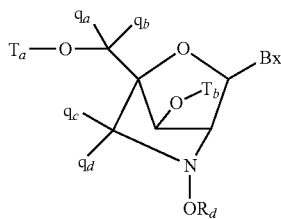

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

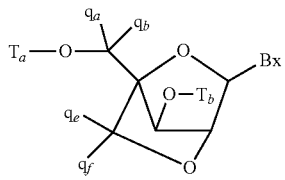

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SO_2J_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-CH$_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-CH$_2$—O-2') BNA and 2'-thio-BNAs, have also been prepared (Kumar et al., *Bioorg. Med Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

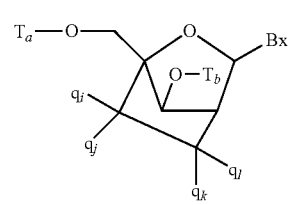

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SO_2J_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)$ NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: C$_1$-C$_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854) or fluoro HNA (F-HNA) having a tetrahydropyran ring system as illustrated below:

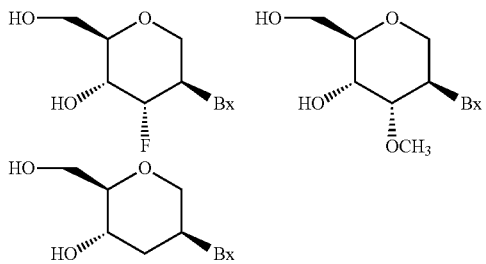

In certain embodiments, sugar surrogates are selected having Formula VII:

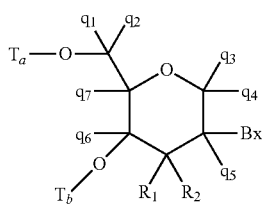

VII wherein independently for each of said at least one tetrahydropyran nucleoside analog of Formula VII:

Bx is a heterocyclic base moiety;

T$_a$ and T$_b$ are each, independently, an internucleoside linking group linking the tetrahydropyran nucleoside analog to the antisense compound or one of T$_a$ and T$_b$ is an internucleoside linking group linking the tetrahydropyran nucleoside analog to the antisense compound and the other of T$_a$ and T$_b$ is H, a hydroxyl protecting group, a linked conjugate group or a 5' or 3'-terminal group;

q$_1$, q$_2$, q$_3$, q$_4$, q$_5$, q$_6$ and q$_7$ are each independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl; and each of R$_1$ and R$_2$ is selected from hydrogen, hydroxyl, halogen, substituted or unsubstituted alkoxy, NJ$_1$J$_2$, SJ$_1$, N$_3$, OC(=X)J$_1$, OC(=X)NJ$_1$J$_2$, NJ$_3$C(=X) NJ$_1$J$_2$ and CN, wherein X is O, S or NJ$_1$ and each J$_1$, J$_2$ and J$_3$ is, independently, H or C$_1$-C$_6$ alkyl.

In certain embodiments, the modified THP nucleosides of Formula VII are provided wherein q$_1$, q$_2$, q$_3$, q$_4$, q$_5$, q$_6$ and q$_7$ are each H. In certain embodiments, at least one of q$_1$, q$_2$, q$_3$, q$_4$, q$_5$, q$_6$ and q$_7$ is other than H. In certain embodiments, at least one of q$_1$, q$_2$, q$_3$, q$_4$, q$_5$, q$_6$ and q$_7$ is methyl. In certain embodiments, THP nucleosides of Formula VII are provided wherein one of R$_1$ and R$_2$ is fluoro. In certain embodiments, R$_1$ is fluoro and R$_2$ is H; R$_1$ is methoxy and R$_2$ is H, and R$_1$ is methoxyethoxy and R$_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry,* 2002, 41, 4503-4510; and U.S. Pat. Nos. 5,698,685; 5,166, 315; 5,185,444; and 5,034,506). As used here, the term "morpholino" means a sugar surrogate having the following formula:

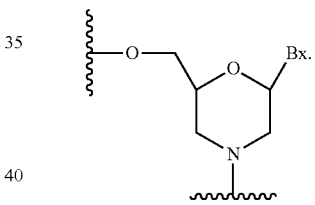

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids,* 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids,* 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

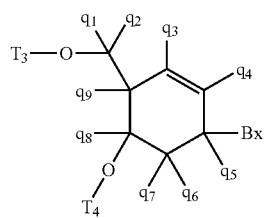

X wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds targeted to a P23H rhodopsin nucleic acid comprise one or more modified nucleobases. In certain embodiments, shortened or gap-widened antisense oligonucleotides targeted to a P23H rhodopsin nucleic acid comprise one or more modified nucleobases. In certain embodiments, the modified nucleobase is 5-methylcytosine. In certain embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), athioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., *Tetrahedron Lett.,* 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

For additional conjugates including those useful for ssRNA and their placement within antisense compounds, see e.g., US Application No. 61/583,963.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides may be mixed with LIPOFECTIN in OPTI-MEM 1 (Invitrogen, Carlsbad, Calif.) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Yet another technique used to introduce antisense oligonucleotides into cultured cells includes free uptake of the oligonucleotides by the cells.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPO- FECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Compositions and Methods for Formulating Pharmaceutical Compositions

Antisense compounds may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to P23H rhodopsin nucleic acid can be utilized in pharmaceutical compositions by combining the antisense compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising an antisense compound targeted to P23H rhodopsin nucleic acid and a pharmaceutically acceptable diluent. In certain embodiments, the pharmaceutically acceptable diluent is water. In certain embodiments, the antisense compound is an antisense oligonucleotide provided herein.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, the compounds or compositions further comprise a pharmaceutically acceptable carrier or diluent.

EXAMPLES

The Examples below describe the screening process to identify lead compounds targeted to P23H mutant rhodopsin. Out of over 400 antisense oligonucleotides that were screened, ISIS 564426, ISIS 664844, ISIS 664867, and ISIS 664884 emerged as the top lead compounds. In particular, ISIS 664844 exhibited the best combination of properties in terms of potency, tolerability, and selectivity for P23H rhodopsin out of over 400 antisense oligonucleotides.

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG".

Example 1: Design and In Vitro Screening of Human Rhodopsin

Antisense oligonucleotides were designed targeting human wild-type or P23H mutant rhodopsin nucleic acid and were tested for their effects on rhodopsin mRNA in vitro. Cell lines either expressing the entire rhodopsin genomic sequence or transfected with a mini gene were used in the assays. The cell lines are described further in the experiments in the Examples below. Two hundred and twelve MOE gapmers, with various motifs (5-10-5, 6-8-6, 7-6-7, 4-10-4, 5-8-5, 6-6-6, 3-10-3, 4-8-4, and 5-6-5) were tested in vitro for potency. Two hundred and two cEt gapmers, as well as gapmers with cEt and MOE modifications, were tested in vitro for potency. Of all these tested gapmers, 104 gapmers were tested in in vitro dose response assays.

The newly designed chimeric antisense oligonucleotides in the Table below were designed as 3-10-3 cEt gapmers. The gapmers are 16 nucleosides in length, wherein the central gap segment comprises ten 2'-deoxynucleosides and is flanked by wing segments on the 5' direction and the 3' direction comprising three nucleosides each. Each nucleoside in the 5' wing segment and each nucleoside in the 3' wing segment has a cEt modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. 'Mismatch' indicates the number of mismatches the oligonucleotide sequence may have with the genomic sequence. Mismatches of more than 1 were not considered. The gapmers are targeted to the human rhodopsin genomic sequence, designated herein as SEQ ID NO: 1 (GENBANK Accession No. NT_005612.16 truncated from nucleotides 35737800 to 35755500 or to the P23H rhodopsin mutant sequence having a cytosine to adenine substitution at position 163 of GENBANK Accession No. NM_000539.3; designated herein as SEQ ID NO:2 representing the mutant sequence), or both sequences. 'n/a' indicates that the particular oligonucleotide had more than one mismatch with the target gene sequence. The gapmers are presented in the Table below.

TABLE 1

3-10-3 gapmers targeting wild-type Rho (SEQ ID NO: 1) and P23H Rho (SEQ ID NO: 2)

| ISIS NO | SEQ ID NO: 1 Start Site | SEQ ID NO: 1 Stop Site | Mismatch with SEQ ID NO: 1 | Sequence | SEQ ID NO: 2 Start Site | SEQ ID NO: 2 Stop Site | SEQ ID NO |
|---|---|---|---|---|---|---|---|
| 564387 | 4979 | 4994 | 1 | AAGTGGCTGCGTACCA | 151 | 166 | 11 |
| 564389 | 4983 | 4998 | 1 | CTCGAAGTGGCTGCGT | 155 | 170 | 12 |
| 564424 | 4977 | 4992 | 1 | GTGGCTGCGTACCACA | 149 | 164 | 13 |
| 564425 | 4981 | 4996 | 1 | CGAAGTGGCTGCGTAC | 153 | 168 | 14 |
| 564426 | 4985 | 5000 | 1 | TACTCGAAGTGGCTGC | 157 | 172 | 15 |
| 564283 | 4898 | 4913 | 0 | CTTGTGGCTGACCCGT | 70 | 85 | 65 |
| 564284 | 4935 | 4950 | 0 | GAAGTTAGGGCCTTCT | 107 | 122 | 66 |
| 564393 | 6112 | 6127 | 0 | CAGCAGAGATATTCCT | n/a | n/a | 67 |
| 564430 | 8414 | 8429 | 0 | CAGGTAGGGAGACCCT | n/a | n/a | 68 |
| 564433 | 8963 | 8978 | 0 | CACCCGCAGTAGGCAC | n/a | n/a | 69 |
| 564431 | 9444 | 9459 | 0 | AGGAAATTGACTTGCC | n/a | n/a | 70 |
| 564338 | 9851 | 9866 | 0 | AGCAGAGGCCTCATCG | 1085 | 1100 | 71 |
| 564342 | 9909 | 9924 | 0 | GAGTCCTAGGCAGGTC | 1143 | 1158 | 72 |
| 564299 | 10092 | 10107 | 0 | GGTGGATGTCCCTTCT | 1326 | 1341 | 73 |
| 564356 | 10192 | 10207 | 0 | AAAGCAAGAATCCTCG | 1426 | 1441 | 74 |
| 564307 | 10517 | 10532 | 0 | GCTATTTACAAAGTGC | 1751 | 1766 | 75 |
| 564370 | 10539 | 10554 | 0 | ACTAGAATCTGTACAG | 1773 | 1788 | 76 |
| 564372 | 10578 | 10593 | 0 | ATTAACTAGTTACATT | 1812 | 1827 | 77 |
| 564315 | 10654 | 10669 | 0 | CCAAGGTTGGGTGAAA | 1888 | 1903 | 78 |
| 564388 | 10757 | 10772 | 0 | GGTCTGATGACTGCAT | 1991 | 2006 | 79 |
| 564325 | 10791 | 10806 | 0 | TTCACCGTCCCCTCC | 2025 | 2040 | 80 |
| 564329 | 10824 | 10839 | 0 | AGGCCCAATCTCACCC | 2058 | 2073 | 81 |
| 564399 | 10930 | 10945 | 0 | AAGAGCAGGTGGCTTC | 2164 | 2179 | 82 |
| 564349 | 11048 | 11063 | 0 | CTAAGCTCTTCGAGAT | 2282 | 2297 | 83 |
| 564363 | 11237 | 11252 | 0 | AGCAGTTACTGAGGCA | 2471 | 2486 | 84 |
| 564373 | 11359 | 11374 | 0 | CAAAACCCACCACCGT | 2593 | 2608 | 85 |
| 564381 | 11456 | 11471 | 0 | TTGGCTCTGCTCATTG | 2690 | 2705 | 86 |
| 564422 | 11465 | 11480 | 0 | CTGTGCTGCTTGGCTC | 2699 | 2714 | 87 |

Gapmers were tested at various doses in HEK-293 cells. HEK-293 cells expressing the human genomic P23H rhodopsin sequence as a stable transfectant were used for these assays. The antisense oligonucleotides were tested in a series of experiments that had similar culture conditions. The results for each experiment are presented in separate tables shown below. Cells were plated at a density of 20,000 cells per well and transfected using electroporation with antisense oligonucleotide, as specified in the Tables below. After a treatment period of approximately 16 hours, RNA was isolated from the cells and rhodopsin mRNA levels were measured by quantitative real-time PCR. Human primer probe set RTS3374 (forward sequence GGAGGT-CAACAACGAGTCTTTTG, designated herein as SEQ ID NO: 5; reverse sequence GGCCTCCTTGACGGTGAA, designated herein as SEQ ID NO: 6; probe sequence TTAT-CATCTTTTTCTGCTATGGGCAGCTCG, designated herein as SEQ ID NO: 7) was used to measure mRNA levels. Rhodopsin mRNA levels were adjusted according to total RNA content, as measured by RIBOGREEN®. Results are presented as percent inhibition of rhodopsin, relative to untreated control cells.

TABLE 2

Dose Response Inhibition of P23H RHO mRNA levels by 3-10-3 cEt gapmers targeted to SEQ ID NO: 2

| ISIS No | 1.25 µM | 2.50 µM | 5.00 µM | 10.00 µM | 20.00 µM | $IC_{50}$ (µM) |
|---|---|---|---|---|---|---|
| 564283 | 12 | 25 | 35 | 22 | 40 | >20 |
| 564284 | 0 | 0 | 3 | 0 | 44 | >20 |
| 564299 | 29 | 30 | 64 | 31 | 11 | >20 |
| 564307 | 26 | 0 | 28 | 21 | 17 | >20 |
| 564315 | 10 | 16 | 28 | 16 | 21 | >20 |
| 564325 | 44 | 52 | 66 | 81 | 86 | 2 |
| 564329 | 0 | 2 | 10 | 16 | 0 | >20 |
| 564349 | 0 | 0 | 0 | 0 | 1 | >20 |
| 564363 | 17 | 0 | 20 | 13 | 31 | >20 |
| 564373 | 19 | 17 | 10 | 29 | 38 | >20 |
| 564381 | 16 | 18 | 34 | 33 | 42 | >20 |
| 564387 | 19 | 26 | 39 | 42 | 76 | 7 |
| 564389 | 35 | 37 | 39 | 18 | 50 | >20 |
| 564393 | 17 | 7 | 20 | 38 | 40 | >20 |

TABLE 3

Dose Response Inhibition of P23H RHO mRNA levels by 3-10-3 cEt gapmers targeted to SEQ ID NO: 2

| ISIS No | 1.25 µM | 2.50 µM | 5.00 µM | 10.00 µM | 20.00 µM | $IC_{50}$ (µM) |
|---|---|---|---|---|---|---|
| 564338 | 0 | 20 | 35 | 19 | 25 | >20 |
| 564342 | 32 | 31 | 40 | 0 | 36 | >20 |
| 564356 | 21 | 18 | 31 | 13 | 0 | >20 |
| 564370 | 0 | 0 | 15 | 10 | 17 | >20 |
| 564372 | 0 | 0 | 0 | 0 | 23 | >20 |
| 564388 | 0 | 0 | 20 | 27 | 2 | >20 |
| 564399 | 9 | 0 | 24 | 30 | 35 | >20 |
| 564422 | 4 | 0 | 20 | 17 | 51 | 9 |
| 564424 | 5 | 0 | 21 | 0 | 0 | >20 |
| 564425 | 0 | 14 | 17 | 14 | 31 | >20 |
| 564426 | 1 | 14 | 17 | 21 | 33 | >20 |
| 564430 | 0 | 0 | 17 | 25 | 5 | >20 |
| 564431 | 26 | 29 | 43 | 52 | 43 | >20 |
| 564433 | 0 | 0 | 13 | 4 | 0 | >20 |

Example 2: Design of Antisense Oligonucleotides with Deoxy, 2'-Alpha-Fluoro, and cEt Chemistry Additional antisense oligonucleotides were designed with the same sequence as ISIS 564387 but with different chemistry. The new antisense oligonucleotides were designed as deoxy, 2'-alpha-fluoro and cEt oligonucleotides.

The 'Chemistry' column of the Table below presents chemical modifications in the oligonucleotide, including the position of the sugar modifications, wherein 'e' indicates a MOE modification, 'k' indicates a cEt modification, d indicates a deoxyribose sugar, and 'f' indicates a 2'-alpha-fluoro modification; 'mC' indicates 5-methycytosine; 'A', 'C', 'T', 'G', and 'U' represent the standard nucleotide notations. All the oligonucleotides are 15 or 16 nucleosides in length. The internucleoside linkages throughout each gapmer are phosphorothioate (P=S) linkages. "Start site" indicates the 5'-most nucleoside to which the gapmer is targeted in the human gene sequence. "Stop site" indicates the 3'-most nucleoside to which the gapmer is targeted human gene sequence. The antisense oligonucleotides were designed to target the mutant sequence (SEQ ID NO:2). The oligonucleotides are presented in the Table below. All the oligonucleotides target nucleotides 151-166 of SEQ ID NO: 2.

TABLE 4

Antisense oligonucleotides targeting the mutant P23H rhodopsin gene (SEQ ID NO: 2)

| IsisNo | Chemistry | SEQ ID NO |
|---|---|---|
| 564387 | Aks Aks Gks Tds Gds Gds mCds Tds Gds mCds Gds Tds Ads mCks mCks Ak | 11 |
| 598202 | Aks Aks Gks Ufs Gds Gds mCds Tds Gds mCds Gds Tds Ads mCks mCks Ak | 11 |
| 598203 | Aks Aks Gks Tds Gfs Gds mCds Tds Gds mCds Gds Tds Ads mCks mCks Ak | 11 |
| 598204 | Aks Aks Gks Tds Gds Gfs mCds Tds Gds mCds Gds Tds Ads mCks mCks Ak | 11 |
| 598205 | Aks Aks Gks Tds Gds Gds Cfs Tds Gds mCds Gds Tds Ads mCks mCks Ak | 11 |
| 598206 | Aks Aks Gks Tds Gds Gds mCds Ufs Gds mCds Gds Tds Ads mCks mCks Ak | 11 |
| 598207 | Aks Aks Gks Tds Gds Gds mCds Tds Gfs mCds Gds Tds Ads mCks mCks Ak | 11 |
| 598208 | Aks Aks Gks Tds Gds Gds mCds Tds Gds Cfs Gds Tds Ads mCks mCks Ak | 11 |
| 598209 | Aks Aks Gks Tds Gds Gds mCds Tds Gds mCds Gfs Tds Ads mCks mCks Ak | 11 |
| 598210 | Aks Aks Gks Tds Gds Gds mCds Tds Gds mCds Gds Ufs Ads mCks mCks Ak | 11 |
| 598211 | Aks Aks Gks Tds Gds Gds mCds Tds Gds mCds Gds Tds Afs mCks mCks Ak | 11 |

Example 3: Antisense Inhibition of Mutant P23H Human Rhodopsin

Additional antisense oligonucleotides were designed targeting the sequence region around the P23H mutation site of the rhodopsin gene and were tested for their effects on mutant rhodopsin mRNA in vitro. The antisense oligonucleotides were tested in a series of experiments that had similar culture conditions. The results for each experiment are presented in separate tables shown below. Cultured HEK293 transfected with a SOD1 minigene containing mutant P23H rhodopsin were used in this assay.

The SOD1 minigene contains the unspliced sequence of SOD1 exon 4, intron 4, and exon 5, with a human rhodopsin sequence with the mutation at P23H. Each sequence was cloned into pcDNA4/TO at HindIII/EcoRI site.

HEK-293 cells with the SOD1 minigene containing mutant P23H rhodopsin were transfected using electroporation with 5 μM or 20 μM antisense oligonucleotide. ISIS 564425, described in the study above, was also included in the assay. After a treatment period of approximately 24 hours, RNA was isolated from the cells and rhodopsin mRNA levels were measured by quantitative real-time PCR. Human primer probe set RTS4220 (forward sequence CACTATAGGGAGACCCAAGC, designated herein as SEQ ID NO: 8; reverse sequence CTGCTTTTTCATGGACCACCA, designated herein as SEQ ID NO: 9; probe sequence CAAAGATGGTGTGGCCG, designated herein as SEQ ID NO: 10), which is targeted to the P23H site, was used to measure mRNA levels. Rhodopsin mRNA levels were adjusted according to total RNA content, as measured by RIBOGREEN®. Results are presented as percent inhibition of rhodopsin, relative to untreated control cells.

The newly designed chimeric antisense oligonucleotides in the Table below were designed as 3-10-3 cEt gapmers, 3-9-3 cEt gapmers, deoxy, MOE and cEt oligonucleotides, or deoxy, 2'-alpha-fluoro and cEt oligonucleotides. The 'Chemistry' column of the Table below presents chemical modifications in the oligonucleotide, including the position of the sugar modifications, wherein 'e' indicates a MOE modification, 'k' indicates a cEt modification, d indicates a deoxyribose sugar, and 'f' indicates a 2'-alpha-fluoro modification; 'mC' indicates 5-methycytosine; 'A', 'C', 'T', 'G', and 'U' represent the standard nucleotide notations. All the oligonucleotides are 15 or 16 nucleosides in length. The internucleoside linkages throughout each gapmer are phosphorothioate (P=S) linkages. "Start site" indicates the 5'-most nucleoside to which the gapmer is targeted in the human gene sequence. "Stop site" indicates the 3'-most nucleoside to which the gapmer is targeted human gene sequence. The antisense oligonucleotides were designed to target the mutant P23H sequence (SEQ ID NO:2). The oligonucleotides are presented in the Table below.

TABLE 5

Inhibition of P23H rhodopsin mRNA by antisense oligonucleotides targeting the mutant rhodopsin gene (SEQ ID NO: 2)

| ISIS NO | SEQ ID NO: 2 Start Site | SEQ ID NO: 2 Stop Site | Chemistry | Sequence | % inhibition (5 μM) | % inhibition (20 μM) | SEQ ID NO |
|---|---|---|---|---|---|---|---|
| 564425 | 153 | 168 | mCkGkAkAdGdTdGdGdmCdTdGdmCdGdTkAkmCk | CGAAGTGGCTGCGTAC | 62 | 72 | 14 |
| 598206 | 151 | 166 | AkAkGkTdGdGdmCdUfGdmCdGdTdAdmCkmCkAk | AAGTGGCUGCGTACCA | 55 | 89 | 62 |
| 664823 | 149 | 164 | GkTdGdGdmCdTdGdmCdGdTdAdmCkmCeAkmCeAk | GTGGCTGCGTACCACA | 6 | 52 | 13 |
| 664824 | 150 | 165 | AkGdTdGdGdmCdTdGdmCdGdTdAkmCemCkAemCk | AGTGGCTGCGTACCAC | 50 | 77 | 16 |
| 664825 | 151 | 166 | AkAdGdTdGdGdmCdTdGdmCdGdTkAcmCkmCcAk | AAGTGGCTGCGTACCA | 39 | 62 | 11 |
| 664826 | 152 | 167 | GkAdAdGdTdGdGdmCdTdGdmCdGkTeAkmCemCk | GAAGTGGCTGCGTACC | 46 | 66 | 17 |
| 664827 | 153 | 168 | mCkGdAdAdGdTdGdGdmCdTdGdmCkGeTkAemCk | CGAAGTGGCTGCGTAC | 53 | 52 | 14 |
| 664828 | 154 | 169 | TkmCdGdAdAdGdTdGdGdmCdTdGkmCeGkTeAk | TCGAAGTGGCTGCGTA | 40 | 66 | 18 |
| 664829 | 155 | 170 | mCkTdmCdGdAdAdGdTdGdGdmCdTkGemCkGeTk | CTCGAAGTGGCTGCGT | 35 | 59 | 12 |
| 664830 | 156 | 171 | AkmCdTdmCdGdAdAdGdTdGdGdmCkTeGkmCeGk | ACTCGAAGTGGCTGCG | 38 | 67 | 19 |
| 664831 | 157 | 172 | TkAdmCdTdmCdGdAdAdGdTdGdGkmCeTkGemCk | TACTCGAAGTGGCTGC | 39 | 63 | 15 |
| 664832 | 158 | 173 | GkTdAdmCdTdmCdGdAdAdGdTdGkGemCkTeGk | GTACTCGAAGTGGCTG | 10 | 51 | 20 |

TABLE 5-continued

Inhibition of P23H rhodopsin mRNA by antisense oligonucleotides targeting the mutant rhodopsin gene (SEQ ID NO: 2)

| ISIS NO | SEQ ID NO: 2 Start Site | SEQ ID NO: 2 Stop Site | Chemistry | Sequence | % inhibition (5 µM) | % inhibition (20 µM) | SEQ ID NO |
|---|---|---|---|---|---|---|---|
| 664833 | 159 | 174 | GkGdTdAdmCdTdmCdGdAdA dGdTkGcGkmCcTk | GGTACTCGAAGTGGCT | 57 | 68 | 21 |
| 664834 | 149 | 164 | GkTkGdGdmCdTdGdmCdGdTd AdmCdmCkAemCkAe | GTGGCTGCGTACCACA | 33 | 50 | 13 |
| 664835 | 150 | 165 | AkGkTdGdGdmCdTdGdmCdG dTdAdmCkmCeAkmCe | AGTGGCTGCGTACCAC | 39 | 75 | 16 |
| 664836 | 151 | 166 | AkAkGdTdGdGdmCdTdGdmC dGdTdAkmCemCkAe | AAGTGGCTGCGTACCA | 56 | 76 | 11 |
| 664837 | 152 | 167 | GkAkAdGdTdGdGdmCdTdGd mCdGdTkAcmCkmCc | GAAGTGGCTGCGTACC | 48 | 72 | 17 |
| 664838 | 153 | 168 | mCkGkAdGdTdGdGdGdmCdT dGdmCdGkTeAkmCe | CGAAGTGGCTGCGTAC | 38 | 84 | 14 |
| 664839 | 154 | 169 | TkmCkGdAdAdGdTdGdGdmC dTdGdmCkGeTkAe | TCGAAGTGGCTGCGTA | 49 | 72 | 18 |
| 664840 | 155 | 170 | mCkTkmCdGdAdAdGdTdGdG dmCdTdGkmCeGkTe | CTCGAAGTGGCTGCGT | 55 | 61 | 12 |
| 664841 | 156 | 171 | AkmCkTdmCdGdAdAdGdTdG dGdmCdTkGcmCkGc | ACTCGAAGTGGCTGCG | 47 | 68 | 19 |
| 664842 | 157 | 172 | TkAkmCdTdmCdGdAdAdGdTd GdGdmCkTeGkmCe | TACTCGAAGTGGCTGC | 48 | 72 | 15 |
| 664843 | 158 | 173 | GkTkAdmCdTdmCdGdAdAdG dTdGdGkmCeTkGe | GTACTCGAAGTGGCTG | 64 | 73 | 20 |
| 664844 | 159 | 174 | GkGkTdAdmCdTdmCdGdAdA dGdTdGkGemCkTe | GGTACTCGAAGTGGCT | 61 | 64 | 21 |
| 664845 | 149 | 164 | GkTkGdGdmCdTdGdmCdGdTd AdmCkmCeAkmCeAk | GTGGCTGCGTACCACA | 10 | 45 | 13 |
| 664846 | 150 | 165 | AkGkTdGdGdmCdTdGdmCdG dTdAkmCemCkAemCk | AGTGGCTGCGTACCAC | 58 | 69 | 16 |
| 664847 | 151 | 166 | AkAkGdTdGdGdmCdTdGdmC dGdTkAemCkmCeAk | AAGTGGCTGCGTACCA | 41 | 56 | 11 |
| 664848 | 152 | 167 | GkAkAdGdTdGdGdmCdTdGd mCdGkTeAkmCemCk | GAAGTGGCTGCGTACC | 49 | 66 | 17 |
| 664849 | 153 | 168 | mCkGkAdAdGdTdGdGdmCdT dGdmCkGeTkAemCk | CGAAGTGGCTGCGTAC | 57 | 72 | 14 |
| 664850 | 154 | 169 | TkmCkGdAdAdGdTdGdGdmC dTdGkmCeGkTeAk | TCGAAGTGGCTGCGTA | 42 | 65 | 18 |
| 664851 | 155 | 170 | mCkTkmCdGdAdAdGdTdGdG dmCdTkGemCkGeTk | CTCGAAGTGGCTGCGT | 20 | 59 | 12 |
| 664852 | 156 | 171 | AkmCkTdmCdGdAdAdGdTdG dGdmCkTeGkmCeGk | ACTCGAAGTGGCTGCG | 42 | 57 | 19 |
| 664853 | 157 | 172 | TkAkmCdTdmCdGdAdAdGdTd GdGkmCeTkGemCk | TACTCGAAGTGGCTGC | 43 | 67 | 15 |
| 664854 | 158 | 173 | GkTkAdmCdTdmCdGdAdAdG dTdGdGkmCeTkGemCk | GTACTCGAAGTGGCTG | 34 | 55 | 20 |
| 664855 | 159 | 174 | GkGkTdAdmCdTdmCdGdAdA dGdTdGkGemCkTk | GGTACTCGAAGTGGCT | 48 | 63 | 21 |
| 664856 | 149 | 164 | GkTkGkGdmCdTdGdmCdGdTd AdmCdmCkAcmCkAc | GTGGCTGCGTACCACA | 20 | 43 | 13 |

TABLE 5-continued

Inhibition of P23H rhodopsin mRNA by antisense oligonucleotides targeting the mutant rhodopsin gene (SEQ ID NO: 2)

| ISIS NO | SEQ ID NO: 2 Start Site | SEQ ID NO: 2 Stop Site | Chemistry | Sequence | % inhibition (5 µM) | % inhibition (20 µM) | SEQ ID NO |
|---|---|---|---|---|---|---|---|
| 664857 | 150 | 165 | AkGkTkGdGdmCdTdGdmCdG dTdAdmCkmCeAkmCe | AGTGGCTGCGTACCAC | 0 | 37 | 16 |
| 664858 | 151 | 166 | AkAkGkTdGdGdmCdTdGdmC dGdTdAkmCemCkAe | AAGTGGCTGCGTACCA | 52 | 81 | 11 |
| 664859 | 152 | 167 | GkAkAkGdTdGdGdmCdTdGd mCdGdTkAemCkmCe | GAAGTGGCTGCGTACC | 52 | 74 | 17 |
| 664860 | 153 | 168 | mCkGkAkAdGdTdGdGdmCdT dGdmCdGkTeAkmCe | CGAAGTGGCTGCGTAC | 56 | 74 | 14 |
| 664861 | 154 | 169 | TkmCkGkAdAdGdTdGdGdmC dTdGdmCkGeTkAe | TCGAAGTGGCTGCGTA | 33 | 58 | 18 |
| 664862 | 155 | 170 | mCkTkmCkGdAdAdGdTdGdG dmCdTdGkmCeGkTe | CTCGAAGTGGCTGCGT | 39 | 64 | 12 |
| 664863 | 156 | 171 | AkmCkTkmCdGdAdAdGdTdG dGdmCdTkGemCkGe | ACTCGAAGTGGCTGCG | 45 | 70 | 19 |
| 664864 | 157 | 172 | TkAkmCkTdmCdGdAdAdGdTd GdGdmCkTeGkmCe | TACTCGAAGTGGCTGC | 49 | 69 | 15 |
| 664865 | 158 | 173 | GkTkAkmCdTdmCdGdAdAdG dTdGdGdkmCeTkGe | GTACTCGAAGTGGCTG | 54 | 67 | 20 |
| 664866 | 159 | 174 | GkGkTkAdmCdTdmCdGdAdA dGdTdGkGemCkTe | GGTACTCGAAGTGGCT | 54 | 64 | 21 |
| 664867 | 157 | 172 | TkAkmCkUfmCdGdAdAdGdTd GdGdmCdTkGkmCk | TACUCGAAGTGGCTGC | 66 | 76 | 64 |
| 664868 | 157 | 172 | TkAkmCkTdCfGdAdAdGdTdG dGdmCdTkGkmCk | TACTCGAAGTGGCTGC | 54 | 69 | 15 |
| 664869 | 157 | 172 | TkAkmCkTdmCdGfAdAdGdTd GdGdmCdTkGkmCk | TACTCGAAGTGGCTGC | 53 | 69 | 15 |
| 664870 | 157 | 172 | TkAkmCkTdmCdGdAfAdGdTd GdGdmCdTkGkmCk | TACTCGAAGTGGCTGC | 54 | 69 | 15 |
| 664871 | 157 | 172 | TkAkmCkTdmCdGdAdAfGdTd GdGdmCdTkGkmCk | TACTCGAAGTGGCTGC | 45 | 68 | 15 |
| 664872 | 157 | 172 | TkAkmCkTdmCdGdAdAdGfrd GdGdmCdTkGkmCk | TACTCGAAGTGGCTGC | 46 | 72 | 15 |
| 664873 | 157 | 172 | TkAkmCkTdmCdGdAdAdGdUf GdGdmCdTkGkmCk | TACTCGAAGUGGCTGC | 42 | 72 | 63 |
| 664874 | 157 | 172 | TkAkmCkTdmCdGdAdAdGdTd GfGdmCdTkGkmCk | TACTCGAAGTGGCTGC | 48 | 69 | 15 |
| 664875 | 157 | 172 | TkAkmCkTdmCdGdAdAdGdTd GdGfmCdTkGkmCk | TACTCGAAGTGGCTGC | 44 | 66 | 15 |
| 664876 | 157 | 172 | TkAkmCkTdmCdGdAdAdGdTd GdGdCfTkGkmCk | TACTCGAAGTGGCTGC | 69 | 77 | 15 |
| 664877 | 150 | 164 | GkTkGdGdmCdTdGdmCdGdTd AdmCdmCkAemCk | GTGGCTGCGTACCAC | 9 | 43 | 22 |
| 664878 | 151 | 165 | AkGkTdGdGdmCdTdGdmCdG dTdAdmCkmCeAk | AGTGGCTGCGTACCA | 45 | 82 | 23 |
| 664879 | 152 | 166 | AkAkGdTdGdGdmCdTdGdmC dGdTdAkmCemCk | AAGTGGCTGCGTACC | 41 | 72 | 24 |

TABLE 5-continued

Inhibition of P23H rhodopsin mRNA by antisense oligonucleotides targeting the mutant rhodopsin gene (SEQ ID NO: 2)

| ISIS NO | SEQ ID NO: 2 Start Site | SEQ ID NO: 2 Stop Site | Chemistry | Sequence | % inhibition (5 µM) | % inhibition (20 µM) | SEQ ID NO |
|---|---|---|---|---|---|---|---|
| 664880 | 153 | 167 | GkAkAdGdTdGdGdmCdTdGdmCdGdTkAemCk | GAAGTGGCTGCGTAC | 29 | 58 | 25 |
| 664881 | 154 | 168 | mCkGkAdAdGdTdGdGdmCdTdGdmCdGkTeAk | CGAAGTGGCTGCGTA | 35 | 63 | 26 |
| 664882 | 155 | 169 | TkmCkGdAdAdGdTdGdGdmCdTdGdmCkGeTk | TCGAAGTGGCTGCGT | 40 | 63 | 27 |
| 664883 | 156 | 170 | mCkTkmCdGdAdAdGdTdGdGdmCdTdGkmCeGk | CTCGAAGTGGCTGCG | 21 | 67 | 28 |
| 664884 | 157 | 171 | AkmCkTdmCdGdAdAdGdTdGdGdmCdTkGcmCk | ACTCGAAGTGGCTGC | 53 | 78 | 29 |
| 664885 | 158 | 172 | TkAkmCdTdmCdGdAdAdGdTdGdGdmCkTeGk | TACTCGAAGTGGCTG | 49 | 78 | 30 |
| 664886 | 159 | 173 | GkTkAdmCdTdmCdGdGdAdAdGdTdGdGkmCeTk | GTACTCGAAGTGGCT | 51 | 64 | 31 |
| 664887 | 160 | 174 | GkGkTdAdmCdTdmCdGdGdAdAdGdTdGdGkGemCk | GGTACTCGAAGTGGC | 64 | 76 | 32 |
| 664899 | 150 | 164 | GkTkGkGdmCdTdGdmCdGdTdAdmCdmCkAkmCk | GTGGCTGCGTACCAC | 0 | 13 | 22 |
| 664900 | 151 | 165 | AkGkTkGdGdmCdTdGdmCdGdTdAdmCkmCkAk | AGTGGCTGCGTACCA | 52 | 81 | 23 |
| 664901 | 152 | 166 | AkAkGkTdGdGdmCdTdGdmCdGdTdAkmCkmCk | AAGTGGCTGCGTACC | 52 | 84 | 24 |
| 664902 | 153 | 167 | GkAkAkGdTdGdGdmCdTdGdmCdGdTkAkmCk | GAAGTGGCTGCGTAC | 41 | 77 | 25 |
| 664903 | 154 | 168 | mCkGkAkAdGdTdGdGdmCdTdGdmCdGkTkAk | CGAAGTGGCTGCGTA | 64 | 80 | 26 |
| 664904 | 155 | 169 | TkmCkGkAdAdGdTdGdGdmCdTdGdmCkGkTk | TCGAAGTGGCTGCGT | 43 | 45 | 27 |
| 664905 | 156 | 170 | mCkTkmCkGdAdAdGdTdGdGdmCdTdGkmCkGk | CTCGAAGTGGCTGCG | 48 | 68 | 28 |
| 664906 | 157 | 171 | AkmCkTkmCdGdAdAdGdTdGdGdmCdTkGkmCk | ACTCGAAGTGGCTGC | 59 | 77 | 29 |
| 664907 | 158 | 172 | TkAkmCkTdmCdGdAdAdGdTdGdGdmCkTkGk | TACTCGAAGTGGCTG | 51 | 71 | 30 |
| 664908 | 159 | 173 | GkTkAkmCdTdmCdGdGdAdAdGdTdGdGkmCkTk | GTACTCGAAGTGGCT | 55 | 67 | 31 |
| 664909 | 160 | 174 | GkGkTkAdmCdTdmCdGdGdAdAdGdTdGkGkmCk | GGTACTCGAAGTGGC | 65 | 69 | 32 |

Example 4: Potency and Selectivity of Antisense Oligonucleotides Targeting the Mutant P23H Rhodopsin Gene Antisense oligonucleotides from Example 3 exhibiting potent in vitro inhibition of the mutant P23H rhodopsin mRNA were selected and tested at various doses in HEK-293 cells transfected with either the mutant P23H (E5-M) or wild-type (E5-C) rhodopsin/SOD1 minigene construct.

The antisense oligonucleotides were tested in a series of experiments that had similar culture conditions. The results for each experiment are presented in separate tables shown below. Cells were transfected using electroporation with 1.25 µM, 2.50 µM, 5.00 µM, 10.00 µM, and 20 µM concentrations of antisense oligonucleotide, as specified in the Tables below. After a treatment period of approximately 16 hours, RNA was isolated from the cells and rhodopsin mRNA levels were measured by quantitative real-time PCR. Human primer probe set RTS4220 was used to measure mRNA levels. Rhodopsin mRNA levels were adjusted according to total RNA content, as measured by RIBOGREEN®. Results are presented as percent inhibition of rhodopsin, relative to untreated control cells.

The half maximal inhibitory concentration ($IC_{50}$) of each oligonucleotide is also presented. Several antisense oligonucleotides selectively inhibited expression of the mutant P23H rhodopsin sequence compared to the WT sequence.

TABLE 6

Percent inhibition of wild-type rhodopsin mRNA in WT HEK293 cells (E5-C)

| ISIS No | 1.250 µM | 2.50 µM | 5.00 µM | 10.00 µM | 20.00 µM | $IC_{50}$ (µM) |
|---|---|---|---|---|---|---|
| 598206 | 2 | 20 | 34 | 44 | 58 | 13 |
| 664833 | 0 | 8 | 0 | 24 | 18 | >20 |
| 664836 | 0 | 13 | 7 | 29 | 39 | >20 |
| 664843 | 0 | 2 | 14 | 20 | 13 | >20 |
| 664844 | 0 | 2 | 12 | 16 | 6 | >20 |
| 664846 | 0 | 8 | 14 | 33 | 52 | 19 |
| 664849 | 0 | 0 | 4 | 0 | 5 | >20 |
| 664860 | 0 | 0 | 0 | 0 | 3 | >20 |
| 664867 | 0 | 12 | 8 | 29 | 33 | >20 |
| 664876 | 2 | 1 | 20 | 17 | 41 | >20 |
| 664887 | 0 | 0 | 14 | 14 | 0 | >20 |
| 664903 | 0 | 0 | 2 | 9 | 0 | >20 |
| 664906 | 5 | 2 | 35 | 19 | 44 | >20 |
| 664909 | 0 | 6 | 9 | 4 | 4 | >20 |

TABLE 7

Percent inhibition of P23H rhodopsin mRNA in mutant HEK293 cells (E5-M)

| ISIS No | 1.250 µM | 2.50 µM | 5.00 µM | 10.00 µM | 20.00 µM | $IC_{50}$ (µM) |
|---|---|---|---|---|---|---|
| 598206 | 24 | 45 | 56 | 74 | 83 | 4 |
| 664833 | 11 | 37 | 49 | 60 | 66 | 6 |
| 664836 | 8 | 37 | 40 | 58 | 70 | 8 |
| 664843 | 40 | 42 | 48 | 62 | 61 | 5 |
| 664844 | 36 | 50 | 51 | 65 | 59 | 3 |
| 664846 | 0 | 17 | 31 | 45 | 63 | 12 |
| 664849 | 21 | 41 | 58 | 49 | 60 | 9 |
| 664860 | 21 | 43 | 54 | 60 | 72 | 4 |
| 664867 | 40 | 47 | 52 | 61 | 69 | 3 |
| 664876 | 2 | 27 | 58 | 67 | 67 | 4 |
| 664887 | 49 | 51 | 60 | 66 | 68 | 2 |
| 664903 | 40 | 48 | 58 | 72 | 73 | 3 |
| 664906 | 32 | 46 | 47 | 61 | 67 | 5 |
| 664909 | 28 | 47 | 58 | 60 | 54 | 3 |

TABLE 8

Percent inhibition of wild-type rhodopsin mRNA in WT HEK293 cells (E5-C)

| ISIS No | 1.250 µM | 2.50 µM | 5.00 µM | 10.00 µM | 20.00 µM | $IC_{50}$ (µM) |
|---|---|---|---|---|---|---|
| 598206 | 0 | 15 | 31 | 51 | 60 | 10 |
| 664824 | 1 | 12 | 25 | 38 | 47 | >20 |
| 664835 | 0 | 2 | 13 | 24 | 52 | 19 |
| 664838 | 0 | 2 | 0 | 23 | 26 | >20 |
| 664840 | 8 | 13 | 23 | 22 | 40 | >20 |
| 664848 | 0 | 0 | 10 | 6 | 14 | >20 |
| 664858 | 9 | 22 | 21 | 48 | 51 | 17 |
| 664878 | 5 | 1 | 20 | 33 | 60 | 16 |
| 664884 | 6 | 10 | 19 | 30 | 50 | >20 |
| 664885 | 0 | 0 | 0 | 22 | 0 | >20 |
| 664900 | 16 | 28 | 31 | 45 | 55 | 15 |
| 664901 | 13 | 11 | 26 | 45 | 56 | 14 |
| 664902 | 0 | 3 | 0 | 22 | 19 | >20 |
| 664908 | 0 | 15 | 4 | 18 | 14 | >20 |

TABLE 9

Percent inhibition of P23H rhodopsin mRNA in mutant HEK293 cells (E5-M)

| ISIS No | 1.250 µM | 2.50 µM | 5.00 µM | 10.00 µM | 20.00 µM | $IC_{50}$ (µM) |
|---|---|---|---|---|---|---|
| 598206 | 30 | 44 | 58 | 72 | 84 | 3 |
| 664824 | 21 | 36 | 45 | 59 | 62 | 7 |
| 664835 | 1 | 16 | 29 | 36 | 66 | 11 |
| 664838 | 6 | 27 | 33 | 47 | 63 | 11 |
| 664840 | 3 | 45 | 29 | 35 | 62 | 14 |
| 664848 | 10 | 16 | 35 | 51 | 59 | 11 |
| 664858 | 55 | 58 | 53 | 62 | 70 | 4 |
| 664878 | 6 | 32 | 47 | 51 | 72 | 7 |
| 664884 | 28 | 37 | 51 | 57 | 68 | 6 |
| 664885 | 6 | 10 | 20 | 51 | 69 | 11 |
| 664900 | 44 | 51 | 52 | 65 | 71 | 2 |
| 664901 | 42 | 50 | 53 | 68 | 70 | 3 |
| 664902 | 0 | 27 | 38 | 57 | 64 | 8 |
| 664908 | 30 | 45 | 49 | 57 | 58 | 6 |

Example 5: Characterization of Potency and Selectivity of Human Antisense Compounds Targeting Mutant P23H Rhodopsin Several additional antisense oligonucleotides were designed to target the mutant P23H rhodopsin gene and were transfected into either mutant P23H rhodopsin (E5-M) or wild-type (E5-C) rhodopsin/SOD1 minigene HEK293 cells. The SOD1 minigene sequence contains the unspliced sequence of SOD1 exon 4, intron 4, and exon 5, with the human wild-type rhodopsin or a rhodopsin sequence with the mutation at P23H. Each sequence was cloned into pcDNA4/TO at HindIII/EcoRI site.

Study 1

The newly designed chimeric antisense oligonucleotides in the Table below were designed as deoxy, MOE and cEt oligonucleotides with a 7 or 8 base deoxy gap Antisense oligonucleotides having a 7 or 8 base deoxy gap are potent and selective for targeting the SNP mutation of the hungtingtin (HTT) gene. Ostergaard M E et al., *Nucleic Acids Res.* 2013 November; 41(21):9634-50; PCT Publication WO 2013/022990. It was expected that antisense oligonucleotides having a 7 or 8 base deoxy gap likewise would potently and selectively target P23H rhodopsin.

The 'Chemistry' column of the Table below presents chemical modifications in the oligonucleotide, including the position of the sugar modifications, wherein 'e' indicates a MOE modification, 'k' indicates a cEt modification, and the number indicates the number of deoxyribose sugars. All the oligonucleotides are 16 nucleosides in length. The internucleoside linkages throughout each gapmer are phosphorothioate (P=S) linkages. All cytosines are 5-methylcytosines. "Start site" indicates the 5'-most nucleoside to which the gapmer is targeted in the human gene sequence. "Stop site" indicates the 3'-most nucleoside to which the gapmer is targeted human gene sequence. The antisense oligonucleotides were designed to target the human mutant P23H rhodopsin sequence (SEQ ID NO:2). The oligonucleotides are presented in the Table below.

TABLE 10

Antisense oligonucleotides targeting mutant P23H rhodopsin (SEQ ID NO: 2)

| ISIS No | SEQ ID NO: 2 Start Site | SEQ ID NO: 2 Stop Site | Sequence | Chemistry | SEQ ID NO |
|---|---|---|---|---|---|
| 589177 | 148 | 163 | TGGCTGCGTACCACAC | eekk-8-kkee | 33 |
| 589193 | 148 | 163 | TGGCTGCGTACCACAC | eeekk-7-kkee | 33 |
| 589178 | 149 | 164 | GTGGCTGCGTACCACA | eekk-8-kkee | 13 |
| 589194 | 149 | 164 | GTGGCTGCGTACCACA | eeekk-7-kkee | 13 |
| 589179 | 150 | 165 | AGTGGCTGCGTACCAC | eekk-8-kkee | 16 |
| 589195 | 150 | 165 | AGTGGCTGCGTACCAC | eeekk-7-kkee | 16 |
| 589180 | 151 | 166 | AAGTGGCTGCGTACCA | eekk-8-kkee | 11 |
| 589196 | 151 | 166 | AAGTGGCTGCGTACCA | eeekk-7-kkee | 11 |
| 589181 | 152 | 167 | GAAGTGGCTGCGTACC | eekk-8-kkee | 17 |
| 589197 | 152 | 167 | GAAGTGGCTGCGTACC | eeekk-7-kkee | 17 |
| 589182 | 153 | 168 | CGAAGTGGCTGCGTAC | eekk-8-kkee | 14 |
| 589198 | 153 | 168 | CGAAGTGGCTGCGTAC | eeekk-7-kkee | 14 |
| 589183 | 154 | 169 | TCGAAGTGGCTGCGTA | eekk-8-kkee | 18 |
| 589199 | 154 | 169 | TCGAAGTGGCTGCGTA | eeekk-7kkee | 18 |
| 589184 | 155 | 170 | CTCGAAGTGGCTGCGT | eekk-8-kkee | 12 |
| 589200 | 155 | 170 | CTCGAAGTGGCTGCGT | eeekk-7-kkee | 12 |
| 589185 | 156 | 171 | ACTCGAAGTGGCTGCG | eekk-8-kkee | 19 |
| 589201 | 156 | 171 | ACTCGAAGTGGCTGCG | eeekk-7-kkee | 19 |
| 589186 | 157 | 172 | TACTCGAAGTGGCTGC | eekk-8-kkee | 15 |
| 589202 | 157 | 172 | TACTCGAAGTGGCTGC | eeekk-7-kkee | 15 |
| 589187 | 158 | 173 | GTACTCGAAGTGGCTG | eekk-8-kkee | 20 |
| 589203 | 158 | 173 | GTACTCGAAGTGGCTG | eeekk-7-kkee | 20 |
| 589188 | 159 | 174 | GGTACTCGAAGTGGCT | eekk-8-kkee | 21 |
| 589204 | 159 | 174 | GGTACTCGAAGTGGCT | eeekk-7-kkee | 21 |
| 589189 | 160 | 175 | GGGTACTCGAAGTGGC | eekk-8-kkee | 34 |
| 589205 | 160 | 175 | GGGTACTCGAAGTGGC | eeekk-7-kkee | 34 |
| 589190 | 161 | 176 | TGGGTACTCGAAGTGG | eekk-8-kkee | 35 |
| 589206 | 161 | 176 | TGGGTACTCGAAGTGG | eeekk-7-kkee | 35 |
| 589191 | 162 | 177 | GTGGGTACTCGAAGTG | eekk-8-kkee | 36 |
| 589207 | 162 | 177 | GTGGGTACTCGAAGTG | eeekk-7-kkee | 36 |
| 589192 | 163 | 178 | TGTGGGTACTCGAAGT | eekk-8-kkee | 37 |
| 589208 | 163 | 178 | TGTGGGTACTCGAAGT | eeekk-7-kkee | 37 |

The antisense oligonucleotides were tested in a series of experiments that had similar culture conditions. The results for each experiment are presented in separate tables shown below. ISIS 564387 and ISIS 598206, described in the studies above, were also included in these assays. Cultured cells at a density of 20,000 cells per well were transfected using electroporation with antisense oligonucleotide. After a treatment period of approximately 24 hours, RNA was isolated from the cells and rhodopsin mRNA levels were measured by quantitative real-time PCR. Human primer probe set RTS4220 was used to measure mRNA levels. Rhodopsin mRNA levels were adjusted according to total RNA content, as measured by RIBOGREEN®. Results are presented as percent inhibition of rhodopsin, relative to untreated control cells. A zero value only indicates that the antisense oligonucleotide did not inhibit mRNA expression.

The half maximal inhibitory concentration ($IC_{50}$) of each oligonucleotide is also presented. Some antisense oligonucleotides selectively reduced mutant P23H rhodopsin mRNA levels compared to WT rhodopsin expression.

TABLE 11

Percent reduction of mutant P23H rhodopsin mRNA in mutant HEK293 cells (E5-M)

| ISIS No | 740.7 nM | 2222.2 nM | 6666.7 nM | 20000.0 nM | $IC_{50}$ (µM) |
|---|---|---|---|---|---|
| 564387 | 34 | 48 | 70 | 83 | 2 |
| 589177 | 22 | 29 | 47 | 65 | 8 |
| 589178 | 18 | 8 | 7 | 27 | >20 |
| 589179 | 10 | 16 | 16 | 33 | >20 |
| 589180 | 21 | 35 | 56 | 73 | 5 |
| 589181 | 20 | 22 | 50 | 67 | 8 |
| 589182 | 31 | 40 | 59 | 72 | 4 |
| 589183 | 17 | 44 | 47 | 64 | 7 |
| 589184 | 27 | 25 | 40 | 60 | 11 |
| 589185 | 1 | 30 | 37 | 61 | 11 |
| 589186 | 21 | 34 | 40 | 62 | 10 |
| 589187 | 28 | 37 | 59 | 64 | 5 |
| 589188 | 23 | 25 | 53 | 65 | 8 |
| 589189 | 16 | 19 | 48 | 56 | 11 |
| 589190 | 20 | 36 | 50 | 64 | 7 |
| 589191 | 0 | 20 | 40 | 49 | 17 |
| 589192 | 9 | 22 | 39 | 54 | 15 |
| 598206 | 41 | 54 | 72 | 84 | 1 |

TABLE 12

Percent reduction of wild-type rhodopsin mRNA in WT HEK293 cells (E5-C)

| ISIS No | 740.7 nM | 2222.2 nM | 6666.7 nM | 20000.0 nM | $IC_{50}$ (µM) |
|---|---|---|---|---|---|
| 564387 | 2 | 24 | 40 | 70 | 9 |
| 589177 | 14 | 27 | 31 | 64 | 13 |
| 589178 | 0 | 5 | 0 | 24 | >20 |
| 589179 | 0 | 16 | 4 | 31 | >20 |
| 589180 | 18 | 19 | 30 | 48 | >20 |
| 589181 | 0 | 9 | 15 | 33 | >20 |
| 589182 | 0 | 10 | 12 | 15 | >20 |
| 589183 | 0 | 14 | 0 | 9 | >20 |
| 589184 | 5 | 0 | 0 | 16 | >20 |
| 589185 | 3 | 5 | 6 | 3 | >20 |
| 589186 | 1 | 15 | 24 | 30 | >20 |
| 589187 | 13 | 7 | 21 | 28 | >20 |
| 589188 | 6 | 9 | 12 | 28 | >20 |
| 589189 | 15 | 5 | 18 | 38 | >20 |
| 589190 | 8 | 3 | 5 | 32 | >20 |
| 589191 | 4 | 7 | 14 | 20 | >20 |
| 589192 | 0 | 0 | 2 | 34 | >20 |
| 598206 | 26 | 18 | 41 | 59 | 12 |

TABLE 13

Percent reduction of mutant P23H rhodopsin mRNA in mutant HEK293 cells (E5-M)

| ISIS No | 740.7 nM | 2222.2 nM | 6666.7 nM | 20000.0 nM | $IC_{50}$ (µM) |
|---|---|---|---|---|---|
| 564387 | 0 | 51 | 67 | 82 | 2 |
| 589193 | 10 | 12 | 28 | 40 | >20 |
| 589194 | 0 | 11 | 19 | 14 | >20 |
| 589195 | 5 | 18 | 20 | 27 | >20 |
| 589196 | 4 | 20 | 39 | 44 | >20 |
| 589197 | 16 | 18 | 47 | 44 | >20 |
| 589198 | 13 | 28 | 38 | 52 | 17 |
| 589199 | 12 | 18 | 31 | 36 | >20 |
| 589200 | 2 | 11 | 32 | 52 | 20 |
| 589201 | 18 | 23 | 21 | 42 | >20 |
| 589202 | 10 | 11 | 20 | 29 | >20 |
| 589203 | 15 | 22 | 36 | 45 | >20 |
| 589204 | 24 | 29 | 33 | 52 | 18 |
| 589205 | 5 | 19 | 27 | 40 | >20 |
| 589206 | 6 | 9 | 22 | 39 | >20 |
| 589207 | 4 | 11 | 25 | 51 | 20 |
| 589208 | 0 | 10 | 10 | 23 | >20 |
| 598206 | 33 | 53 | 73 | 83 | 2 |

TABLE 14

Percent reduction of wild-type rhodopsin mRNA in WT HEK293 cells (E5-C)

| ISIS No | 740.7 nM | 2222.2 nM | 6666.7 nM | 20000.0 nM | $IC_{50}$ (µM) |
|---|---|---|---|---|---|
| 564387 | 0 | 22 | 40 | 60 | 11 |
| 589193 | 0 | 2 | 5 | 38 | >20 |
| 589194 | 0 | 0 | 8 | 13 | >20 |
| 589195 | 0 | 4 | 9 | 13 | >20 |
| 589196 | 12 | 0 | 12 | 30 | >20 |
| 589197 | 14 | 2 | 13 | 20 | >20 |
| 589198 | 10 | 0 | 18 | 10 | >20 |
| 589199 | 2 | 0 | 5 | 0 | >20 |
| 589200 | 0 | 0 | 0 | 20 | >20 |
| 589201 | 0 | 0 | 0 | 16 | >20 |
| 589202 | 0 | 18 | 0 | 7 | >20 |
| 589203 | 10 | 6 | 22 | 28 | >20 |
| 589204 | 0 | 1 | 10 | 17 | >20 |
| 589205 | 4 | 3 | 4 | 11 | >20 |
| 589206 | 0 | 0 | 3 | 20 | >20 |
| 589207 | 0 | 0 | 0 | 24 | >20 |
| 589208 | 2 | 0 | 4 | 14 | >20 |
| 598206 | 9 | 8 | 37 | 51 | 17 |

The summary table is shown below and indicates that only some, much fewer than expected, antisense oligonucleotides having a 7 or 8 base deoxy gap potently and selectively reduced mutant P23H rhodopsin mRNA levels compared to WT levels. The data show that the 7 or 8 base deoxy gap motif may not always be effective to potently and selectively target a mutation from one gene to another.

TABLE 15

Selectivity of antisense oligonucleotides

| ISIS No | $IC_{50}$ (µM) in WT Rho cells | $IC_{50}$ (µM) in P23H Rho cells |
|---|---|---|
| 564387 | 11 | 2 |
| 589177 | 13 | 8 |
| 589178 | >20 | >20 |
| 589179 | >20 | >20 |
| 589180 | >20 | 5 |
| 589181 | >20 | 8 |

TABLE 15-continued

Selectivity of antisense oligonucleotides

| ISIS No | IC$_{50}$ (μM) in WT Rho cells | IC$_{50}$ (μM) in P23H Rho cells |
|---|---|---|
| 589182 | >20 | 4 |
| 589183 | >20 | 7 |
| 589184 | >20 | 11 |
| 589185 | >20 | 11 |
| 589186 | >20 | 10 |
| 589187 | >20 | 5 |
| 589188 | >20 | 8 |
| 589189 | >20 | 11 |
| 589190 | >20 | 7 |
| 589191 | >20 | 17 |
| 589192 | >20 | 15 |
| 589193 | >20 | >20 |
| 589194 | >20 | >20 |
| 589195 | >20 | >20 |
| 589196 | >20 | >20 |
| 589197 | >20 | >20 |
| 589198 | >20 | 17 |
| 589199 | >20 | >20 |
| 589200 | >20 | 20 |
| 589201 | >20 | >20 |
| 589202 | >20 | >20 |
| 589203 | >20 | >20 |
| 589204 | >20 | 18 |
| 589205 | >20 | >20 |
| 589206 | >20 | >20 |
| 589207 | >20 | 20 |
| 589208 | >20 | >20 |
| 598206 | 17 | 2 |

Study 2

Antisense oligonucleotides described in the studies above were further tested. The antisense oligonucleotides were tested in a series of experiments that had similar culture conditions. ISIS 549144 (GGCCAATACGCCGTCA; designated herein as SEQ ID NO: 89), a 3-10-3 cEt gapmer that does not target any known gene, was used as a control. The results for each experiment are presented in separate tables shown below. Cultured HEK293 cells at a density of 30,000 cells per well were transfected using electroporation with antisense oligonucleotide. After a treatment period of approximately 24 hours, RNA was isolated from the cells and rhodopsin mRNA levels were measured by quantitative real-time PCR. Human primer probe set RTS4220, which is targeted to the SOD1 mini gene, was used to measure mRNA levels. Rhodopsin mRNA levels were adjusted according to total RNA content, as measured by RIBOGREEN®. Results are presented as percent inhibition of rhodopsin, relative to untreated control cells. A zero value only indicates that the antisense oligonucleotide did not inhibit mRNA expression.

The half maximal inhibitory concentration (IC$_{50}$) of each oligonucleotide is also presented. Several antisense oligonucleotides reduced mutant rhodopsin mRNA levels potently and selectively.

TABLE 16

Percent reduction of wild-type rhodopsin mRNA in WT HEK293 cells (E5-C)

| ISIS No | 1.25 μM | 2.5 μM | 5 μM | 10 μM | 20 μM | IC$_{50}$ (μM) |
|---|---|---|---|---|---|---|
| 549144 | 0 | 7 | 0 | 0 | 0 | >20 |
| 598206 | 2 | 20 | 34 | 44 | 58 | 13 |
| 664833 | 0 | 8 | 0 | 24 | 18 | >20 |
| 664836 | 0 | 13 | 7 | 29 | 39 | >20 |
| 664843 | 0 | 2 | 14 | 20 | 13 | >20 |
| 664844 | 0 | 2 | 12 | 16 | 6 | >20 |
| 664846 | 0 | 8 | 14 | 33 | 52 | 19 |
| 664849 | 0 | 0 | 4 | 0 | 5 | >20 |
| 664860 | 0 | 0 | 0 | 0 | 3 | >20 |
| 664867 | 0 | 12 | 8 | 29 | 33 | >20 |
| 664876 | 2 | 1 | 20 | 17 | 41 | >20 |
| 664887 | 0 | 0 | 14 | 14 | 0 | >20 |
| 664903 | 0 | 0 | 2 | 9 | 0 | >20 |
| 664906 | 5 | 2 | 35 | 19 | 44 | >20 |
| 664909 | 0 | 6 | 9 | 4 | 4 | >20 |

TABLE 17

Percent reduction of P23H rhodopsin mRNA in mutant HEK293 cells (E5-M)

| ISIS No | 1.25 μM | 2.5 μM | 5 μM | 10 μM | 20 μM | IC$_{50}$ (μM) |
|---|---|---|---|---|---|---|
| 549144 | 0 | 0 | 0 | 2 | 0 | >20 |
| 598206 | 24 | 45 | 56 | 74 | 83 | 4 |
| 664833 | 11 | 37 | 49 | 60 | 66 | 6 |
| 664836 | 8 | 37 | 40 | 58 | 70 | 8 |
| 664843 | 40 | 42 | 48 | 62 | 61 | 5 |
| 664844 | 36 | 50 | 51 | 65 | 59 | 3 |
| 664846 | 0 | 17 | 31 | 45 | 63 | 12 |
| 664849 | 21 | 41 | 58 | 49 | 60 | 9 |
| 664860 | 21 | 43 | 54 | 60 | 72 | 4 |
| 664867 | 40 | 47 | 52 | 61 | 69 | 3 |
| 664876 | 2 | 27 | 58 | 67 | 67 | 4 |
| 664887 | 49 | 51 | 60 | 66 | 68 | 2 |
| 664903 | 40 | 48 | 58 | 72 | 73 | 3 |
| 664906 | 32 | 46 | 47 | 61 | 67 | 5 |
| 664909 | 28 | 47 | 58 | 60 | 54 | 3 |

TABLE 18

Percent reduction of wild-type rhodopsin mRNA in WT HEK293 cells (E5-C)

| ISIS No | 1.25 μM | 2.5 μM | 5 μM | 10 μM | 20 μM | IC$_{50}$ (μM) |
|---|---|---|---|---|---|---|
| 549144 | 0 | 0 | 0 | 0 | 0 | >20 |
| 598206 | 0 | 15 | 31 | 51 | 60 | 10 |
| 664824 | 1 | 12 | 25 | 38 | 47 | >20 |
| 664835 | 0 | 2 | 13 | 24 | 52 | 19 |
| 664838 | 0 | 2 | 0 | 23 | 26 | >20 |
| 664840 | 8 | 13 | 23 | 22 | 40 | >20 |
| 664848 | 0 | 0 | 10 | 6 | 14 | >20 |
| 664858 | 9 | 22 | 21 | 48 | 51 | 17 |
| 664878 | 5 | 1 | 20 | 33 | 60 | 16 |
| 664884 | 6 | 10 | 19 | 30 | 50 | >20 |
| 664885 | 0 | 0 | 0 | 22 | 0 | >20 |
| 664900 | 16 | 28 | 31 | 45 | 55 | 15 |
| 664901 | 13 | 11 | 26 | 45 | 56 | 14 |
| 664902 | 0 | 3 | 0 | 22 | 19 | >20 |
| 664908 | 0 | 15 | 4 | 18 | 14 | >20 |

TABLE 19

Percent reduction of P23H rhodopsin mRNA in mutant HEK293 cells (E5-M)

| ISIS No | 1.25 µM | 2.5 µM | 5 µM | 10 µM | 20 µM | IC$_{50}$ (µM) |
|---|---|---|---|---|---|---|
| 549144 | 0 | 0 | 0 | 0 | 0 | >20 |
| 598206 | 30 | 44 | 58 | 72 | 84 | 3 |
| 664824 | 21 | 36 | 45 | 59 | 62 | 7 |
| 664835 | 1 | 16 | 29 | 36 | 66 | 11 |
| 664838 | 6 | 27 | 33 | 47 | 63 | 11 |
| 664840 | 3 | 45 | 29 | 35 | 62 | 14 |
| 664848 | 10 | 16 | 35 | 51 | 59 | 11 |
| 664858 | 55 | 58 | 53 | 62 | 70 | 4 |
| 664878 | 6 | 32 | 47 | 51 | 72 | 7 |
| 664884 | 28 | 37 | 51 | 57 | 68 | 6 |
| 664885 | 6 | 10 | 20 | 51 | 69 | 11 |
| 664900 | 44 | 51 | 52 | 65 | 71 | 2 |
| 664901 | 42 | 50 | 53 | 68 | 70 | 3 |
| 664902 | 0 | 27 | 38 | 57 | 64 | 8 |
| 664908 | 30 | 45 | 49 | 57 | 58 | 6 |

The summary table is shown below and indicates that some antisense oligonucleotides, including ISIS 664844, potently and selectively reduced mutant rhodopsin mRNA levels compared to WT rhodopsin levels.

TABLE 20

Selectivity of antisense oligonucleotides

| ISIS No | IC$_{50}$ (µM) in WT Rho cells | IC$_{50}$ (µM) in P23H Rho cells |
|---|---|---|
| 549144 | >20 | >20 |
| 598206 | 10 | 3 |
| 664824 | >20 | 7 |
| 664833 | >20 | 6 |
| 664835 | 19 | 11 |
| 664836 | >20 | 8 |
| 664838 | >20 | 11 |
| 664840 | >20 | 14 |
| 664843 | >20 | 5 |
| 664844 | >20 | 3 |
| 664846 | 19 | 12 |
| 664848 | >20 | 11 |
| 664849 | >20 | 9 |
| 664858 | 17 | 4 |
| 664860 | >20 | 4 |
| 664867 | >20 | 3 |
| 664876 | >20 | 4 |
| 664878 | 16 | 7 |
| 664884 | >20 | 6 |
| 664885 | >20 | 11 |
| 664887 | >20 | 2 |
| 664900 | 15 | 2 |
| 664901 | 14 | 3 |
| 664902 | >20 | 8 |
| 664903 | >20 | 3 |
| 664906 | >20 | 5 |
| 664908 | >20 | 6 |
| 664909 | >20 | 3 |

Study 3

Antisense oligonucleotides from the studies described above were further tested. Two new oligonucleotides were designed and are presented in the Table below.

ISIS 586139 is a 3-10-3 cEt gapmer, wherein the central gap segment comprises ten 2'-deoxynucleosides and is flanked by wing segments on the 5' direction and the 3' direction comprising three nucleosides each. ISIS 643801 is a 2-10-2 cEt gapmer, wherein the central gap segment comprises ten 2'-deoxynucleosides and is flanked by wing segments on the 5' direction and the 3' direction comprising two nucleosides each. Each nucleoside in the 5' wing segment and each nucleoside in the 3' wing segment has a cEt modification. The internucleoside linkages throughout each gapmer are phosphorothioate (P=S) linkages. All cytosine residues throughout each gapmer are 5-methylcytosines. The internucleoside linkages throughout each gapmer are phosphorothioate (P=S) linkages. "Start site" indicates the 5'-most nucleoside to which the gapmer is targeted in the human gene sequence. "Stop site" indicates the 3'-most nucleoside to which the gapmer is targeted human gene sequence. The antisense oligonucleotides were designed to target the mutant sequence (SEQ ID NO:2). The oligonucleotides are presented in the Table below.

TABLE 21

Antisense oligonucleotides targeting P23H rhodopsin (SEQ ID NO: 2)

| ISIS No | SEQ ID NO: 2 Start Site | SEQ ID NO: 2 Stop Site | Sequence | SEQ ID NO |
|---|---|---|---|---|
| 586139 | 158 | 173 | GTACTCGAAGTGGCTG | 20 |
| 643801 | 152 | 165 | AGTGGCTGCGTACC | 38 |

The antisense oligonucleotides were tested in a series of experiments that had similar culture conditions. ISIS 549144 was used as a control. The results for each experiment are presented in separate tables shown below. Cultured HEK293 cells having the SOD-1 minigene at a density of 30,000 cells per well were transfected using electroporation with antisense oligonucleotide. After a treatment period of approximately 24 hours, RNA was isolated from the cells and rhodopsin mRNA levels were measured by quantitative real-time PCR. Human primer probe set RTS4220, which is targeted to the SOD1 mini gene, was used to measure mRNA levels. Rhodopsin mRNA levels were adjusted according to total RNA content, as measured by RIBOGREEN®. Results are presented as percent inhibition of rhodopsin, relative to untreated control cells. A zero value only indicates that the antisense oligonucleotide did not inhibit mRNA expression.

The half maximal inhibitory concentration (IC$_{50}$) of each oligonucleotide is also presented. Several antisense oligonucleotides reduced mutant rhodopsin mRNA levels potently and selectively.

TABLE 22

Percent reduction of wild-type rhodopsin mRNA in WT HEK293 cells (E5-C)

| ISIS No | 0.5 µM | 1.5 µM | 4.4 µM | 13.3 µM | 40 µM | IC$_{50}$ (µM) |
|---|---|---|---|---|---|---|
| 549144 | 0 | 1 | 0 | 4 | 0 | >40 |
| 564387 | 0 | 22 | 42 | 59 | 78 | 8 |
| 564389 | 0 | 0 | 0 | 33 | 38 | >40 |
| 564425 | 2 | 0 | 5 | 17 | 7 | >40 |
| 564426 | 10 | 19 | 35 | 45 | 61 | 17 |
| 564431 | 0 | 0 | 0 | 0 | 4 | >40 |
| 586139 | 3 | 20 | 15 | 35 | 53 | 33 |
| 589177 | 37 | 54 | 53 | 62 | 64 | 3 |
| 643801 | 0 | 12 | 27 | 53 | 68 | 14 |
| 664838 | 0 | 0 | 0 | 12 | 16 | >40 |
| 664843 | 0 | 25 | 13 | 41 | 50 | 34 |
| 664844 | 0 | 3 | 6 | 10 | 17 | >40 |

TABLE 22-continued

Percent reduction of wild-type rhodopsin mRNA in WT HEK293 cells (E5-C)

| ISIS No | 0.5 µM | 1.5 µM | 4.4 µM | 13.3 µM | 40 µM | IC$_{50}$ (µM) |
|---|---|---|---|---|---|---|
| 664860 | 0 | 0 | 0 | 9 | 10 | >40 |
| 664867 | 0 | 16 | 4 | 44 | 52 | 29 |
| 664884 | 3 | 0 | 0 | 43 | 53 | 28 |
| 664885 | 0 | 0 | 0 | 3 | 13 | >40 |

TABLE 23

Percent reduction of P23H rhodopsin mRNA in mutant HEK293 cells (E5-M)

| ISIS No | 0.5 µM | 1.5 µM | 4.4 µM | 13.3 µM | 40 µM | IC$_{50}$ (µM) |
|---|---|---|---|---|---|---|
| 549144 | 0 | 0 | 4 | 0 | 10 | >40 |
| 564387 | 8 | 36 | 69 | 85 | 90 | 3 |
| 564389 | 0 | 37 | 64 | 77 | 77 | 3 |
| 564425 | 25 | 41 | 47 | 75 | 80 | 3 |
| 564426 | 26 | 43 | 49 | 79 | 80 | 2 |
| 564431 | 0 | 0 | 0 | 10 | 17 | >40 |
| 586139 | 34 | 42 | 63 | 75 | 83 | 2 |
| 589177 | 28 | 33 | 40 | 60 | 64 | 8 |
| 643801 | 1 | 27 | 49 | 72 | 88 | 5 |
| 664838 | 0 | 16 | 39 | 45 | 78 | 9 |
| 664843 | 23 | 31 | 64 | 76 | 78 | 3 |
| 664844 | 29 | 56 | 66 | 75 | 73 | 2 |
| 664860 | 11 | 36 | 65 | 77 | 83 | 3 |
| 664867 | 17 | 44 | 64 | 76 | 82 | 3 |
| 664884 | 0 | 28 | 54 | 71 | 84 | 5 |
| 664885 | 0 | 25 | 53 | 73 | 83 | 5 |

The results of studies in mutant and WT cells are summarized in the Table below. The IC$_{50}$ values show the potency of certain oligonucleotides. The data shows that some oligonucleotides, including ISIS 664844, demonstrate potency and selectivity for the human mutant P23H rhodopsin gene. The sequence of the oligonucleotide with the mutation bolded and underlined is also shown.

TABLE 24

IC50 for the WT and P23H mutant cells

| ISIS No | Sequence with mutation | WT | Mutant | SEQ ID NO: |
|---|---|---|---|---|
| 564389 | CTCGAAG<u>T</u>GGCTGCGT | >40 | 3 | 12 |
| 564426 | TACTCGAAG<u>T</u>GGCTGC | 17 | 2 | 15 |
| 664844 | GGTACTCGAAG<u>T</u>GGCT | >40 | 2 | 21 |
| 664860 | CGAAG<u>T</u>GGCTGCGTAC | >40 | 3 | 14 |
| 664867 | TACUCGAAG<u>T</u>GGCTGC | 29 | 3 | 64 |
| 664884 | ACTCGAAG<u>T</u>GGCTGC | 28 | 5 | 29 |

Example 6: Efficacy of Antisense Oligonucleotides Targeting Human Rhodopsin in Transgenic Mice Additional antisense oligonucleotides were designed and tested in two transgenic (Tg) mice models. The germline of these mice were inserted with a P23H mutant allele from a retinitis pigmentosa patient (Olsson, J. E. et al., Neuron. 1992. 9: 815-830). A total of 144 antisense oligonucleotides were tested. Not all the antisense oligonucleotides tested demonstrated potency in inhibiting mutant rhodopsin expression.

Study 1

P23H Tg mice were treated with ISIS oligonucleotides described in the studies above. Two newly designed 3-10-3 cEt gapmers targeted to rhodopsin away from the P23H site, ISIS 564426 and ISIS 564432, were also included in the study.

TABLE 25

3-10-3 cEt gapmers targeting human rhodopsin (SEQ ID NO: 1)

| ISIS NO | SEQ ID NO: 1 Start Site | SEQ ID NO: 1 Stop Site | Sequence | SEQ ID NO |
|---|---|---|---|---|
| 564429 | 7798 | 7813 | TAAGAAATGGACCCTA | 39 |
| 564432 | 8692 | 8707 | CCCGGGTCCAGACCAT | 40 |

P23H Tg mice were randomly divided into treatment groups of 3-5 mice each. The gapmers were injected at a dose of 50 µg via intravitreal injection in the right eye of each of the mice. The left eye of the animals was injected with PBS and served as the control. Mice were sacrificed after 7 days. Human P23H rhodopsin expression from eye tissue was measured with the human-specific primer probe set RTS3363. The results are normalized to the expression of mouse cone rod homeobox. Percent inhibition is relative to the expression seen in mice treated with PBS. The data are presented in the Table below and demonstrate that some antisense oligonucleotides reduced mutant human P23H rhodopsin expression in vivo.

TABLE 26

% inhibition of human P23H rhodopsin mRNA

| ISIS No | % |
|---|---|
| 564431 | 89 |
| 564299 | 41 |
| 564329 | 38 |
| 564363 | 21 |
| 564370 | 34 |
| 564372 | 15 |
| 564373 | 33 |
| 564422 | 43 |
| 564429 | 31 |
| 564432 | 6 |
| 564433 | 7 |

Study 2

The newly designed chimeric antisense oligonucleotides in the Tables below were designed as 3-10-3 cEt gapmers, 5-7-4 cEt gapmers, 5-10-5 MOE gapmers, 6-8-6 MOE gapmers, 7-6-7 MOE gapmers, 4-10-4 MOE gapmers, 5-8-5 MOE gapmers, 4-8-4 MOE gapmers, or 5-6-5 MOE gapmers.

The 3-10-3 cEt gapmers are 16 nucleosides in length, wherein the central gap segment comprises ten 2'-deoxynucleosides and is flanked by wing segments on the 5' direction and the 3' direction comprising three nucleosides each. Each nucleoside in the 5' wing segment and each nucleoside in the 3' wing segment has a cEt modification. The 5-7-4 cEt gapmers are 16 nucleosides in length, wherein the central gap segment comprises seven 2'-deoxynucleosides and is flanked by wing segments on the 5' direction and the 3' direction comprising five and four nucleosides respectively. Each nucleoside in the 5' wing segment and each nucleoside in the 3' wing segment has a cEt modification. The 5-10-5 MOE gapmers are 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a MOE modification. The 6-8-6 MOE gapmers are 20 nucleosides in length, wherein the central gap segment comprises eight 2'-deoxynucleosides and is flanked by wing segments on the 5' direction and the 3' direction comprising six nucleosides each. Each nucleoside in the 5' wing segment and each nucleoside in the 3' wing segment has a MOE modification. The 7-6-7 MOE gapmers are 20 nucleosides in length, wherein the central gap segment comprises six 2'-deoxynucleosides and is flanked by wing segments on the 5' direction and the 3' direction comprising seven nucleosides each. Each nucleoside in the 5' wing segment and each nucleoside in the 3' wing segment has a MOE modification. The 4-10-4 MOE gapmers are 18 nucleosides in length, wherein the central gap segment comprises ten 2'-deoxynucleosides and is flanked by wing segments on the 5' direction and the 3' direction comprising four nucleosides each. Each nucleoside in the 5' wing segment and each nucleoside in the 3' wing segment has a MOE modification. The 5-8-5 MOE gapmers are 18 nucleosides in length, wherein the central gap segment comprises eight 2'-deoxynucleosides and is flanked by wing segments on the 5' direction and the 3' direction comprising five nucleosides each. Each nucleoside in the 5' wing segment and each nucleoside in the 3' wing segment has a MOE modification.

The 4-8-4 MOE gapmers are 16 nucleosides in length, wherein the central gap segment comprises eight 2'-deoxynucleosides and is flanked by wing segments on the 5' direction and the 3' direction comprising four nucleosides each. Each nucleoside in the 5' wing segment and each nucleoside in the 3' wing segment has a MOE modification. The 5-6-5 MOE gapmers are 16 nucleosides in length, wherein the central gap segment comprises six 2'-deoxynucleosides and is flanked by wing segments on the 5' direction and the 3' direction comprising five nucleosides each. Each nucleoside in the 5' wing segment and each nucleoside in the 3' wing segment has a MOE modification.

The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. The antisense oligonucleotides were designed to target the mutant sequence (SEQ ID NO:2).

P23H Tg mice were randomly divided into treatment groups of 3-5 mice each. The gapmers were injected at a dose of 50 μg via intravitreal injection in the right eye of each of the mice. The left eye of the animals was injected with PBS and served as the control. Mice were sacrificed after 7 days. Human rhodopsin expression was measured with the human-specific primer probe set RTS3363. The results are normalized to the expression of mouse cone rod homeobox. Percent inhibition is relative to the expression seen in mice treated with PBS. A '0' value inhibition only indicates that the oligonucleotide did not inhibit expression of in this particular instance. The data are presented in the Table below.

TABLE 27

Inhibition of rhodopsin expression in P23H Tg mice

| ISIS NO | SEQ ID NO: 2 Start Site | SEQ ID NO: 2 Stop Site | Motif | Sequence | % inhibition | SEQ ID NO |
|---------|---|---|---|---|---|---|
| 564426 | 157 | 172 | 3-10-3 cEt | TACTCGAAGTGGCTGC | 41 | 15 |
| 598213 | 152 | 167 | 5-7-4 cEt | GAAGTGGCTGCGTACC | 0 | 17 |
| 614060 | 150 | 169 | 5-10-5 MOE | TCGAAGTGGCTGCGTACCAC | 6 | 41 |
| 614067 | 157 | 176 | 5-10-5 MOE | TGGGTACTCGAAGTGGCTGC | 0 | 42 |
| 614068 | 158 | 177 | 5-10-5 MOE | GTGGGTACTCGAAGTGGCTG | 0 | 43 |
| 614074 | 164 | 183 | 5-10-5 MOE | AGTACTGTGGGTACTCGAAG | 0 | 44 |
| 614075 | 143 | 162 | 6-8-6 MOE | GGCTGCGTACCACACCCGTC | 9 | 45 |
| 614082 | 150 | 169 | 6-8-6 MOE | TCGAAGTGGCTGCGTACCAC | 7 | 41 |
| 614083 | 151 | 170 | 6-8-6 MOE | CTCGAAGTGGCTGCGTACCA | 0 | 46 |
| 614089 | 157 | 176 | 6-8-6 MOE | TGGGTACTCGAAGTGGCTGC | 0 | 42 |
| 614105 | 151 | 170 | 7-6-7 MOE | CTCGAAGTGGCTGCGTACCA | 0 | 46 |
| 614111 | 157 | 176 | 7-6-7 MOE | TGGGTACTCGAAGTGGCTGC | 0 | 42 |
| 614166 | 150 | 167 | 4-10-4 MOE | GAAGTGGCTGCGTACCAC | 0 | 47 |
| 614167 | 151 | 168 | 4-10-4 MOE | CGAAGTGGCTGCGTACCA | 34 | 48 |
| 614187 | 151 | 168 | 5-8-5 MOE | CGAAGTGGCTGCGTACCA | 0 | 48 |
| 614188 | 152 | 169 | 5-8-5 MOE | TCGAAGTGGCTGCGTACC | 1 | 49 |

TABLE 27-continued

Inhibition of rhodopsin expression in P23H Tg mice

| ISIS NO | SEQ ID NO: 2 Start Site | SEQ ID NO: 2 Stop Site | Motif | Sequence | % inhibition | SEQ ID NO |
|---|---|---|---|---|---|---|
| 614194 | 158 | 175 | 5-8-5 MOE | GGGTACTCGAAGTGGCTG | 0 | 50 |
| 614195 | 159 | 176 | 5-8-5 MOE | TGGGTACTCGAAGTGGCT | 11 | 51 |
| 614250 | 158 | 173 | 4-8-4 MOE | GTACTCGAAGTGGCTG | 5 | 20 |
| 614251 | 159 | 174 | 4-8-4 MOE | GGTACTCGAAGTGGCT | 0 | 21 |
| 614263 | 153 | 168 | 5-6-5 MOE | CGAAGTGGCTGCGTAC | 0 | 14 |
| 614268 | 158 | 173 | 5-6-5 MOE | GTACTCGAAGTGGCTG | 16 | 20 |

Study 3

The newly designed chimeric antisense oligonucleotides in the Tables below were designed as 3-10-3 cEt gapmers, 6-8-6 MOE gapmers, 4-10-4 MOE gapmers, 5-8-5 MOE gapmers, 6-6-6 MOE gapmers, 3-10-3 MOE gapmers, or 4-8-4 MOE gapmers.

The 3-10-3 cEt gapmers are 16 nucleosides in length, wherein the central gap segment comprises ten 2'-deoxynucleosides and is flanked by wing segments on the 5' direction and the 3' direction comprising three nucleosides each. Each nucleoside in the 5' wing segment and each nucleoside in the 3' wing segment has a cEt modification. The 6-8-6 MOE gapmers are 20 nucleosides in length, wherein the central gap segment comprises eight 2'-deoxynucleosides and is flanked by wing segments on the 5' direction and the 3' direction comprising six nucleosides each. Each nucleoside in the 5' wing segment and each nucleoside in the 3' wing segment has a MOE modification. The 4-10-4 MOE gapmers are 18 nucleosides in length, wherein the central gap segment comprises ten 2'-deoxynucleosides and is flanked by wing segments on the 5' direction and the 3' direction comprising four nucleosides each. Each nucleoside in the 5' wing segment and each nucleoside in the 3' wing segment has a MOE modification. The 5-8-5 MOE gapmers are 18 nucleosides in length, wherein the central gap segment comprises eight 2'-deoxynucleosides and is flanked by wing segments on the 5' direction and the 3' direction comprising five nucleosides each. Each nucleoside in the 5' wing segment and each nucleoside in the 3' wing segment has a MOE modification. The 6-6-6 MOE gapmers are 18 nucleosides in length, wherein the central gap segment comprises six 2'-deoxynucleosides and is flanked by wing segments on the 5' direction and the 3' direction comprising six nucleosides each. Each nucleoside in the 5' wing segment and each nucleoside in the 3' wing segment has a MOE modification. The 3-10-3 MOE gapmers are 16 nucleosides in length, wherein the central gap segment comprises ten 2'-deoxynucleosides and is flanked by wing segments on the 5' direction and the 3' direction comprising three nucleosides each. Each nucleoside in the 5' wing segment and each nucleoside in the 3' wing segment has a MOE modification. The 4-8-4 MOE gapmers are 16 nucleosides in length, wherein the central gap segment comprises eight 2'-deoxynucleosides and is flanked by wing segments on the 5' direction and the 3' direction comprising four nucleosides each. Each nucleoside in the 5' wing segment and each nucleoside in the 3' wing segment has a MOE modification. The internucleoside linkages throughout each gapmer are phosphorothioate (P=S) linkages. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted human gene sequence. The antisense oligonucleotides were designed to target the mutant sequence (SEQ ID NO:2).

P23H Tg mice were randomly divided into treatment groups of 3-5 mice each. The gapmers were injected at a dose of 50 µg via intravitreal injection in the right eye of each of the mice. The left eye of the animals was injected with PBS and served as the control. Mice were sacrificed after 7 days. Human rhodopsin expression was measured with the human-specific primer probe set RTS3363. The results are normalized to the expression of mouse cone rod homeobox. Percent inhibition is relative to the expression seen in mice treated with PBS. A '0' value inhibition only indicates that the oligonucleotide did not inhibit expression of in this particular instance. The data are presented in the Table below.

TABLE 28

Inhibition of rhodopsin expression in P23H Tg mice

| ISIS NO | SEQ ID NO: 2 Start Site | SEQ ID NO: 2 Stop Site | Motif | Sequence | % inhibition | SEQ ID NO |
|---|---|---|---|---|---|---|
| 614225 | 151 | 166 | 3-10-3 MOE | AAGTGGCTGCGTACCA | 1 | 11 |
| 614208 | 152 | 169 | 6-6-6 MOE | TCGAAGTGGCTGCGTACC | 0 | 49 |

TABLE 28-continued

Inhibition of rhodopsin expression in P23H Tg mice

| ISIS NO | SEQ ID NO: 2 Start Site | SEQ ID NO: 2 Stop Site | Motif | Sequence | % inhibition | SEQ ID NO |
|---|---|---|---|---|---|---|
| 614226 | 152 | 167 | 3-10-3 MOE | GAAGTGGCTGCGTACC | 3 | 17 |
| 614244 | 152 | 167 | 4-8-4 MOE | GAAGTGGCTGCGTACC | 2 | 17 |
| 614227 | 153 | 168 | 3-10-3 MOE | CGAAGTGGCTGCGTAC | 0 | 14 |
| 614245 | 153 | 168 | 4-8-4 MOE | CGAAGTGGCTGCGTAC | 0 | 14 |
| 614246 | 154 | 169 | 4-8-4 MOE | TCGAAGTGGCTGCGTA | 0 | 18 |
| 614088 | 156 | 175 | 6-8-6 MOE | GGGTACTCGAAGTGGCTGCG | 3 | 52 |
| 614192 | 156 | 173 | 5-8-5 MOE | GTACTCGAAGTGGCTGCG | 5 | 53 |
| 614193 | 157 | 174 | 5-8-5 MOE | GGTACTCGAAGTGGCTGC | 6 | 54 |
| 614231 | 157 | 172 | 3-10-3 MOE | TACTCGAAGTGGCTGC | 11 | 15 |
| 614232 | 158 | 173 | 3-10-3 MOE | GTACTCGAAGTGGCTG | 10 | 20 |
| 614233 | 159 | 174 | 3-10-3 MOE | GGTACTCGAAGTGGCT | 0 | 44 |
| 586141 | 160 | 175 | 3-10-3 cEt | GGGTACTCGAAGTGGC | 0 | 34 |
| 586143 | 162 | 177 | 3-10-3 cEt | GTGGGTACTCGAAGTG | 0 | 36 |
| 614178 | 162 | 179 | 4-10-4 MOE | CTGTGGGTACTCGAAGTG | 30 | 55 |
| 564340 | 1133 | 1148 | 3-10-3 cEt | CAGGTCTTAGGCCGGG | 20 | 56 |

Study 4

The newly designed chimeric antisense oligonucleotides in the Tables below were designed as 3-10-3 cEt gapmers or deoxy, 2'-fluoro and cEt oligonucleotides. The 3-10-3 cEt gapmers are 16 nucleosides in length, wherein the central gap segment comprises ten 2'-deoxynucleosides and is flanked by wing segments on the 5' direction and the 3' direction comprising three nucleosides each. Each nucleoside in the 5' wing segment and each nucleoside in the 3' wing segment has a cEt modification. The deoxy, 2'-fluoro and cEt oligonucleotides are 16 nucleosides in length. The 'Chemistry' column of the Table below presents the position of the sugar modifications, wherein 'e' indicates a MOE modification, 'k' indicates a cEt modification, d indicates a deoxyribose sugar, and 'f' indicates a 2'-alpha-fluoro modification; 'mC' indicates 5-methycytosine; 'A', 'C', 'T', 'G', and 'U' represent the standard nucleotide notations. The internucleoside linkages throughout each gapmer are phosphorothioate (P=S) linkages.

"Start site" indicates the 5'-most nucleoside to which the gapmer is targeted in the human gene sequence. "Stop site" indicates the 3'-most nucleoside to which the gapmer is targeted human gene sequence. The gapmers are targeted to either the human rhodopsin genomic sequence, designated herein as SEQ ID NO: 1 (GENBANK Accession No. NT 005612.16 truncated from nucleotides 35737800 to 35755500) or the mutant sequence (SEQ ID NO:2), or both. 'n/a' indicates that the antisense oligonucleotide does not target that particular gene sequence with 100% complementarity.

P23H Tg mice were randomly divided into treatment groups of 3-5 mice each. ISIS 564340 from the studies described above was also included in this assay. 3-10-3 cEt gapmers were injected at a dose of 50 µg via intravitreal injection in the right eye of each of the mice. The left eye of the animals was injected with PBS and served as the control. Mice were sacrificed after 7 days. Human rhodopsin expression from eye tissue was measured with the human-specific primer probe set RTS3363. The results are normalized to the expression of mouse cone rod homeobox. Percent inhibition is relative to the expression seen in mice treated with PBS.

TABLE 29

Inhibition of rhodopsin expression in P23H Tg mice

| ISIS NO | Motif | Sequence | % inhibition | SEQ ID NO: 2 Start Site | SEQ ID NO: 2 Stop Site | SEQ ID NO |
|---|---|---|---|---|---|---|
| 586138 | AkmCkTkmCdGdAdAdGdTdGdGdmCdTdGkmCkGk | ACTCGAAGTGGCTGCG | 24 | 156 | 171 | 19 |
| 598204 | AkAkGkTdGdGfmCdTdGdmCdGdTdAdmCkmCkAk | AAGTGGCTGCGTACCA | 2 | 151 | 166 | 11 |

TABLE 29-continued

Inhibition of rhodopsin expression in P23H Tg mice

| ISIS NO | Motif | Sequence | % inhibition | SEQ ID NO: 2 Start Site | SEQ ID NO: 2 Stop Site | SEQ ID NO |
|---|---|---|---|---|---|---|
| 598208 | AkAkGkTdGdGdmCdTdGdCfGdTdAdmCkmCkAk | AAGTGGCTGCGTACCA | 15 | 151 | 166 | 11 |
| 598211 | AkAkGkTdGdGdmCdTdGdmCdGdTdAfmCkmCkAk | AAGTGGCTGCGTACCA | 13 | 151 | 166 | 11 |
| 564340 | mCkAkGkGdTdmCdTdTdAdGdGdmCdmCdGkGkGk | CAGGTCTTAGGCCGGG | 21 | 1133 | 1148 | 56 |

Study 5

Additional oligonucleotides were designed with the same sequence as antisense oligonucleotides described above but with different chemistries. The newly designed chimeric antisense oligonucleotides in the Tables below were designed as 3-10-3 cEt gapmers or deoxy, 2'-fluoro and cEt oligonucleotides. The 3-10-3 cEt gapmers are 16 nucleosides in length, wherein the central gap segment comprises ten 2'-deoxynucleosides and is flanked by wing segments on the 5' direction and the 3' direction comprising three nucleosides each. Each nucleoside in the 5' wing segment and each nucleoside in the 3' wing segment has a cEt modification. The deoxy, 2'-fluoro and cEt oligonucleotides are 16 nucleosides in length. The 'Chemistry' column of the Table below presents the position of the sugar modifications, wherein 'e' indicates a MOE modification, 'k' indicates a cEt modification, d indicates a deoxyribose sugar, and 'f' indicates a 2'-alpha-fluoro modification; 'mC' indicates 5-methycytosine; 'A', 'C', 'T', 'G', and 'U' represent the standard nucleotide notations. The internucleoside linkages throughout each gapmer are phosphorothioate (P=S) linkages.

'Parent oligo' indicates the ISIS oligonucleotide with the same sequence as the newly designed oligonucleotide. "Start site" indicates the 5'-most nucleoside to which the gapmer is targeted in the human gene sequence. "Stop site" indicates the 3'-most nucleoside to which the gapmer is targeted human gene sequence. The gapmers are targeted to the human mutant P23H sequence (SEQ ID NO:2). 'n/a' indicates that the antisense oligonucleotide does not target that particular gene sequence with 100% complementarity.

TABLE 30

Antisense oligonucleotides targeting SEQ ID NO: 2

| ISIS NO | Parent oligo | SEQ ID NO: 2 Start Site | SEQ ID NO: 2 Stop Site | Motif | Sequence | SEQ ID NO |
|---|---|---|---|---|---|---|
| 586136 | — | 152 | 167 | GkAkAkGdTdGdGdmCdTdGdmCdGdTdAkmCkmCk | GAAGTGGCTGCGTACC | 17 |
| 586137 | — | 154 | 169 | TkmCkGkAdAdGdTdGdGdGdmCdTdGdmCdGkTkAk | TCGAAGTGGCTGCGTA | 18 |
| 598212 | 586136 | 152 | 167 | GkAkAkGkTdGdGdmCdTdGdmCdGdTkAkmCkmCk | GAAGTGGCTGCGTACC | 17 |
| 598214 | 561125 | 153 | 168 | mCkGkAkAkGdTdGdGdmCdTdGdmCdGkTkAkmCk | CGAAGTGGCTGCGTAC | 14 |
| 598215 | 564425 | 153 | 168 | mCkGkAkAkGkTdGdGdGdmCdTdGdmCdGkTkAkmCk | CGAAGTGGCTGCGTAC | 14 |
| 598216 | 586137 | 154 | 169 | TkmCkGkAkAdGdTdGdGdmCdTdGdmCkGkTkAk | TCGAAGTGGCTGCGTA | 18 |
| 598217 | 586137 | 154 | 169 | TkmCkGkAkAkGdTdGdGdmCdTdGdmCkGkTkAk | TCGAAGTGGCTGCGTA | 18 |
| 598218 | 564389 | 155 | 170 | mCkTkmCkGkAdAdGdTdGdGdmCdTdGkmCkGdTk | CTCGAAGTGGCTGCGT | 12 |
| 598219 | 564389 | 155 | 170 | mCkTkmCkGkAkAdGdTdGdGdmCdTdGkmCkGkTk | CTCGAAGTGGCTGCGT | 12 |

P23H Tg mice were randomly divided into treatment groups of 3-5 mice each. ISIS 564431 and ISIS 598206, described in the studies above were also included in this assay. The antisense oligonucleotides were injected at a dose of 50 μg via intravitreal injection in the right eye of each of the mice. The left eye of the animals was injected with PBS and served as the control. Mice were sacrificed after 7 days. Human rhodopsin expression from eye tissue was measured with the human-specific primer probe set RTS3363. The results are normalized to the expression of mouse cone rod homeobox. Percent inhibition is relative to the expression seen in mice treated with PBS. A '0' value inhibition only indicates that the oligonucleotide did not inhibit expression of in this particular instance. The data are presented in the Table below and demonstrate that some antisense oligonucleotides reduced mutant human rhodopsin expression in vivo.

TABLE 31

Percent inhibition of mutant P23H rhodopsin expression

| ISIS NO | % inhibition |
|---|---|
| 564431 | 64 |
| 586136 | 29 |
| 586137 | 19 |
| 598206 | 51 |
| 598209 | 14 |
| 598210 | 10 |
| 598212 | 8 |
| 598214 | 47 |
| 598215 | 10 |
| 598216 | 25 |
| 598217 | 4 |
| 598218 | 20 |
| 598219 | 10 |

Example 7: Potency and Selectivity of Human Antisense Compounds Targeting Human Mutant P23H Rhodopsin Additional antisense oligonucleotides were designed targeting the P23H site of human mutant P23H rhodopsin. These oligonucleotides as well as antisense oligonucleotides described in the studies above were further tested. The oligonucleotides were transfected into either HEK293 cells expressing either P23H mutant rhodopsin/SOD1 minigene (E5-M) or wild-type rhodopsin/SOD1 minigene (E5-C).

The new antisense oligonucleotides were designed as 3-10-3 cEt gapmers. The gapmers are 16 nucleosides in length, wherein the central gap segment comprises ten 2'-deoxynucleosides and is flanked by wing segments on the 5' direction and the 3' direction comprising three nucleosides each. Each nucleoside in the 5' wing segment and each nucleoside in the 3' wing segment has a cEt modification. The internucleoside linkages throughout each gapmer are phosphorothioate (P=S) linkages.

"Start site" indicates the 5'-most nucleoside to which the gapmer is targeted in the human gene sequence. "Stop site" indicates the 3'-most nucleoside to which the gapmer is targeted human gene sequence. The gapmers are targeted to the human mutant P23H sequence (SEQ ID NO:2). 'Mismatch indicates the number of mismatches the oligonucleotide has with the rhodopsin sequence in addition the to P23H mutation

TABLE 32

3-10-3 cEt gapmers targeted to SEQ ID NO: 2

| ISIS No | Sequence | Start Site on SEQ ID NO: 2 | Stop Site on SEQ ID NO: 2 | Mismatches with SEQ ID NO: 2 | SEQ ID NO |
|---|---|---|---|---|---|
| 586125 | GGGGCTGCGTACCACA | 149 | 164 | 1 | 57 |
| 586126 | AAGGGGCTGCGTACCA | 151 | 166 | 1 | 58 |
| 586127 | CGAAGGGGCTGCGTAC | 153 | 168 | 1 | 59 |
| 586128 | CTCGAAGGGGCTGCGT | 155 | 170 | 1 | 60 |
| 586129 | TACTCGAAGGGGCTGC | 157 | 172 | 1 | 61 |

The antisense oligonucleotides were tested in a series of experiments that had similar culture conditions. The results for each experiment are presented in separate tables shown below. Cultured cells at a density of 30,000 cells per well were transfected using electroporation with antisense oligonucleotide. After a treatment period of approximately 24 hours, RNA was isolated from the cells and rhodopsin mRNA levels were measured by quantitative real-time PCR. Human primer probe set RTS3374 was used to measure mRNA levels. Rhodopsin mRNA levels were adjusted according to total RNA content, as measured by RIBOGREEN®. Results are presented as percent inhibition of rhodopsin, relative to untreated control cells. A zero value only indicates that the antisense oligonucleotide did not inhibit mRNA expression.

The half maximal inhibitory concentration ($IC_{50}$) of each oligonucleotide is also presented. Several antisense oligonucleotides differentially reduced mutant rhodopsin mRNA levels compared to WT rhodopsin expression.

TABLE 33

Percent reduction of wild-type rhodopsin mRNA in WT HEK293 cells (E5-C)

| ISIS No | 0.74 µM | 2.22 µM | 6.67 µM | 20.00 µM | $IC_{50}$ (µM) |
|---|---|---|---|---|---|
| 564389 | 0 | 25 | 26 | 67 | 12 |
| 564425 | 0 | 16 | 31 | 55 | 16 |
| 586136 | 6 | 23 | 54 | 72 | 7 |
| 586137 | 0 | 18 | 28 | 58 | 15 |
| 598202 | 25 | 34 | 60 | 79 | 4 |
| 598203 | 10 | 26 | 43 | 69 | 8 |
| 598204 | 12 | 30 | 50 | 81 | 5 |
| 598205 | 0 | 21 | 39 | 66 | 10 |
| 598206 | 23 | 28 | 68 | 81 | 4 |
| 598207 | 0 | 15 | 53 | 70 | 8 |
| 598208 | 22 | 38 | 64 | 81 | 4 |
| 598209 | 0 | 18 | 50 | 75 | 7 |
| 598210 | 10 | 14 | 45 | 76 | 8 |
| 598211 | 14 | 39 | 69 | 80 | 4 |
| 598212 | 19 | 16 | 27 | 45 | >20 |
| 598213 | 25 | 0 | 30 | 61 | 14 |
| 564325 | 17 | 22 | 35 | 53 | 17 |
| 564431 | 35 | 36 | 45 | 66 | 7 |
| 564387 | 18 | 35 | 53 | 53 | 6 |

TABLE 34

Percent reduction of P23H rhodopsin mRNA in mutant HEK293 cells (E5-M)

| ISIS No | 0.74 µM | 2.22 µM | 6.67 µM | 20.00 µM | $IC_{50}$ (µM) |
|---|---|---|---|---|---|
| 564389 | 15 | 33 | 42 | 57 | 11 |
| 564425 | 0 | 39 | 49 | 58 | 8 |
| 586136 | 14 | 33 | 55 | 72 | 6 |
| 586137 | 10 | 39 | 26 | 62 | 13 |
| 598202 | 20 | 40 | 58 | 65 | 4 |
| 598203 | 0 | 20 | 46 | 57 | 11 |
| 598204 | 8 | 29 | 52 | 61 | 8 |
| 598205 | 1 | 24 | 38 | 59 | 12 |
| 598206 | 15 | 49 | 66 | 67 | 3 |
| 598207 | 16 | 29 | 49 | 54 | 11 |
| 598208 | 20 | 30 | 59 | 54 | 5 |
| 598209 | 17 | 33 | 53 | 63 | 7 |
| 598210 | 14 | 29 | 50 | 68 | 7 |
| 598211 | 17 | 39 | 58 | 77 | 4 |
| 598212 | 14 | 21 | 51 | 64 | 8 |
| 598213 | 8 | 13 | 27 | 42 | >20 |
| 564325 | 31 | 18 | 29 | 56 | 17 |
| 564431 | 15 | 33 | 45 | 54 | 12 |
| 564387 | 24 | 32 | 51 | 51 | 12 |

TABLE 35

Percent reduction of wild-type rhodopsin mRNA in WT HEK293 cells (E5-C)

| ISIS No | 0.74 µM | 2.22 µM | 6.67 µM | 20.00 µM | IC$_{50}$ (µM) |
|---|---|---|---|---|---|
| 598214 | 0 | 4 | 28 | 51 | 19 |
| 598215 | 0 | 9 | 17 | 41 | >20 |
| 598216 | 0 | 3 | 16 | 48 | >20 |
| 598217 | 0 | 6 | 10 | 30 | >20 |
| 598218 | 0 | 8 | 18 | 25 | >20 |
| 598219 | 0 | 9 | 7 | 29 | >20 |
| 564389 | 13 | 0 | 36 | 63 | 14 |
| 564424 | 10 | 4 | 31 | 47 | >20 |
| 564425 | 0 | 0 | 20 | 60 | 19 |
| 564426 | 0 | 16 | 47 | 56 | 11 |
| 586125 | 35 | 49 | 69 | 74 | 2 |
| 586126 | 18 | 27 | 57 | 71 | 6 |
| 586127 | 12 | 25 | 51 | 68 | 7 |
| 586128 | 14 | 37 | 50 | 65 | 7 |
| 586129 | 52 | 67 | 81 | 83 | 1 |
| 564325 | 25 | 28 | 36 | 61 | 12 |
| 564431 | 13 | 41 | 59 | 60 | 4 |
| 564387 | 7 | 12 | 54 | 76 | 7 |

TABLE 36

Percent reduction of P23H rhodopsin mRNA in mutant HEK293 cells (E5-M)

| ISIS No | 0.74 µM | 2.22 µM | 6.67 µM | 20.00 µM | IC$_{50}$ (µM) |
|---|---|---|---|---|---|
| 598214 | 32 | 46 | 57 | 72 | 3 |
| 598215 | 21 | 39 | 39 | 66 | 8 |
| 598216 | 18 | 26 | 30 | 53 | 17 |
| 598217 | 7 | 20 | 16 | 50 | 20 |
| 598218 | 5 | 6 | 21 | 48 | >20 |
| 598219 | 0 | 13 | 33 | 45 | >20 |
| 564389 | 1 | 39 | 31 | 60 | 12 |
| 564424 | 0 | 24 | 25 | 44 | >20 |
| 564425 | 20 | 41 | 51 | 54 | 9 |
| 564426 | 19 | 31 | 50 | 60 | 8 |
| 586125 | 0 | 19 | 25 | 53 | 20 |
| 586126 | 15 | 22 | 35 | 42 | >20 |
| 586127 | 7 | 13 | 4 | 28 | >20 |
| 586128 | 2 | 10 | 18 | 18 | >20 |
| 586129 | 17 | 19 | 34 | 48 | >20 |
| 564325 | 30 | 23 | 33 | 50 | 19 |
| 564431 | 2 | 24 | 39 | 42 | >20 |
| 564387 | 11 | 12 | 53 | 64 | 9 |

The summary table is shown below and indicates that only a few antisense oligonucleotides selectively reduced mutant rhodopsin mRNA levels compared to WT rhodopsin levels. A selectivity of '1' indicates that the antisense oligonucleotide did not selectively reduce the mutant sequence compared to the control. A negative selectivity value indicates that the antisense oligonucleotide targeted the wild-type

TABLE 37

Selectivity of antisense oligonucleotides

| ISIS No | Selectivity |
|---|---|
| 598214 | 5.8 |
| 598215 | 2.6 |
| 598216 | 1.2 |
| 598217 | 1.0 |
| 598218 | 1.0 |
| 598219 | 1.0 |
| 564389 | 1.0 |
| 564424 | 1.0 |
| 564425 | 1.7 |
| 564426 | 1.4 |
| 586125 | −9.5 |
| 586126 | −3.5 |
| 586127 | −2.8 |
| 586128 | −2.9 |
| 586129 | −31.5 |
| 564325 | −1.6 |
| 564431 | −5.0 |
| 564387 | −1.2 |
| 564389 | 1.0 |
| 564425 | 2.0 |
| 586136 | 1.2 |
| 586137 | 1.2 |
| 598202 | 1.0 |
| 598203 | −1.4 |
| 598204 | −1.5 |
| 598205 | −1.2 |
| 598206 | 1.3 |
| 598207 | 1.5 |
| 598208 | −1.3 |
| 598209 | 1.0 |
| 598210 | 1.2 |
| 598211 | −1.1 |
| 598212 | 2.5 |
| 598213 | −1.5 |
| 564325 | 1.0 |
| 564431 | −1.7 |
| 564387 | −2.1 |

Example 8: Efficacy and Selectivity of Antisense Oligonucleotides Targeting Human Rhodopsin in Transgenic Mice Antisense oligonucleotides selected from the studies described above were further tested in transgenic mouse models. The germline of these mice were inserted with either a wild-type rhodopsin allele or a P23H mutant rhodopsin allele from a retinitis pigmentosa patient.

Study 1

P23H Tg mice were randomly divided into treatment groups of 4 mice each. ISIS oligonucleotides were injected via intravitreal injection in the right eye of each of the mice. The left eye of the animals was injected with PBS and served as the control. Mice were sacrificed after 7 days. Human rhodopsin expression from eye tissue was measured with the human-specific primer probe set RTS3363. The results are normalized to the expression of mouse cone rod homeobox. Percent inhibition is relative to the expression seen in the eye tissue treated with PBS. A '0' value inhibition only indicates that the oligonucleotide did not inhibit expression of in this particular instance. The data are presented in the Table below and demonstrated that the antisense oligonucleotides inhibit expression of mutant P23H rhodopsin gene in a dose-dependent manner.

TABLE 38

% inhibition of human mutant P23H rhodopsin expression

| ISIS No | Chemistry | Dose (µg) | % inhibition |
|---|---|---|---|
| 564431 | 3-10-3 cEt | 20 | 64 |
| 564426 | 3-10-3 cEt | 50 | 63 |
|  |  | 20 | 42 |
|  |  | 10 | 12 |

TABLE 38-continued

% inhibition of human mutant P23H rhodopsin expression

| ISIS No | Chemistry | Dose (µg) | % inhibition |
|---|---|---|---|
| 664844 | Deoxy, MOE, and cEt | 50 | 50 |
|  |  | 20 | 41 |
|  |  | 10 | 32 |
| 664860 | Deoxy, MOE, and cEt | 50 | 44 |
|  |  | 20 | 39 |
|  |  | 10 | 30 |
| 664867 | Deoxy, 2'-alpha-fluoro and cEt | 50 | 62 |
|  |  | 20 | 25 |
|  |  | 10 | 0 |
| 664884 | Deoxy, MOE, and cEt | 50 | 68 |
|  |  | 20 | 48 |
|  |  | 10 | 17 |

Study 2

Human WT rhodopsin Tg mice were randomly divided into treatment groups of 3-6 mice each. ISIS oligonucleotides, selected from the studies described above, were injected via intravitreal injection in the right eye of each of the mice. The left eye of the animals was injected with PBS and served as the control. Mice were sacrificed after 7 days. Human rhodopsin expression from eye tissue was measured with the human-specific primer probe set RTS3363. The results are normalized to the expression of mouse cone rod homeobox. Percent inhibition is relative to the expression seen in the eye tissue treated with PBS. A '0' value inhibition only indicates that the oligonucleotide did not inhibit expression of in this particular instance. The results are presented in the Table below and demonstrate the several antisense oligonucleotides do not effectively inhibit expression of the wild-type rhodopsin gene.

TABLE 39

% reduction in human WT rhodopsin expression

| ISIS No | Chemistry | Dose (µg) | % inhibition |
|---|---|---|---|
| 564389 | 3-10-3 cEt | 50 | 10 |
|  |  | 20 | 0 |
|  |  | 10 | 10 |
| 564426 | 3-10-3 cEt | 50 | 21 |
|  |  | 20 | 3 |
|  |  | 10 | 0 |
| 664844 | Deoxy, MOE and cEt | 50 | 22 |
|  |  | 20 | 24 |
|  |  | 10 | 0 |
| 664860 | Deoxy, MOE and cEt | 50 | 39 |
|  |  | 20 | 19 |
|  |  | 10 | 5 |
| 664884 | Deoxy, MOE and cEt | 50 | 28 |
|  |  | 20 | 0 |
|  |  | 10 | 2 |
| 664867 | Deoxy, 2'-alpha-fluoro and cEt | 50 | 9 |
|  |  | 20 | 16 |
|  |  | 10 | 7 |

Example 9: Confirmation of Efficacy and Selectivity of Antisense Oligonucleotides Targeting Human Rhodopsin in Transgenic Mice Select antisense oligonucleotides that demonstrated potency and selectivity in the studies described above were further tested in the human P23H or wild-type rhodopsin transgenic mouse models. The data demonstrates the selectivity of the leads for the mutant rhodopsin gene.

Study 1

P23H Tg mice were randomly divided into treatment groups of 4 mice each. ISIS oligonucleotides, selected from the studies described above, were injected via intravitreal injection in the right eye of each of the mice. The left eye of the animals was injected with PBS and served as the control. Mice were sacrificed after 7 days. Human rhodopsin expression from eye tissue was measured with the human-specific primer probe set RTS3363. The results are normalized to the expression of mouse cone rod homeobox. Percent inhibition is relative to the expression seen in the eye treated with PBS. The data presented in the Table below are the average of two separate experiments and demonstrate that the antisense oligonucleotides inhibit expression of mutant rhodopsin gene in a dose-dependent manner.

TABLE 40

% inhibition of human mutant P23H rhodopsin expression

| ISIS No | Chemistry | Dose (µg) | % inhibition |
|---|---|---|---|
| 564426 | 3-10-3 cEt | 50 | 68 |
|  |  | 35 | 45 |
|  |  | 20 | 27 |
| 664844 | Deoxy, MOE, and cEt | 50 | 40 |
|  |  | 35 | 37 |
|  |  | 20 | 20 |
| 664867 | Deoxy, 2'-alpha-fluoro and cEt | 50 | 58 |
|  |  | 35 | 43 |
|  |  | 20 | 26 |
| 664884 | Deoxy, MOE, and cEt | 50 | 51 |
|  |  | 35 | 48 |
|  |  | 20 | 25 |

Study 2

Human WT rhodopsin Tg mice were randomly divided into treatment groups of 4 mice each. ISIS oligonucleotides, selected from the studies described above, were injected via intravitreal injection in the right eye of each of the mice. The left eye of the animals was injected with PBS and served as the control. Mice were sacrificed after 7 days. Human rhodopsin expression from eye tissue was measured with the human-specific primer probe set RTS3363. The results are normalized to the expression of mouse cone rod homeobox. Percent inhibition is relative to the expression seen in the eye treated with PBS. The data presented in the Table below are the average of two separate experiments and demonstrate that the antisense oligonucleotides do not target the WT rhodopsin gene.

TABLE 41

% inhibition of human WT rhodopsin expression

| ISIS No | Chemistry | Dose (µg) | % inhibition |
|---|---|---|---|
| 564426 | 3-10-3 cEt | 50 | 13 |
|  |  | 35 | 13 |
| 664844 | Deoxy, MOE, and cEt | 50 | 16 |
|  |  | 35 | 17 |
| 664867 | Deoxy, 2'-alpha-fluoro and cEt | 50 | 12 |
|  |  | 35 | 3 |
| 664884 | Deoxy, MOE, and cEt | 50 | 14 |
|  |  | 35 | 1 |

Example 10: Tolerability Study of Antisense Oligonucleotides Targeting Human Mutant P23H Rhodopsin in Cynomolgus Monkeys Cynomolgus monkeys were treated with ISIS antisense oligonucleotides selected from studies described in the Examples above. The objective of this study was to determine the tolerability of the antisense oligonucleotides when given as a single intravitreal injection to cynomolgus monkeys. A cynomolgus surrogate ASO, ISIS 602881, was included in the study.

At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well. The human antisense oligonucleotides tested are cross-reactive with the rhesus genomic sequence (the complement of GENBANK Accession No. NW_001096632.1 truncated from nucleotides 1522000 to 1532000, designated herein as SEQ ID NO: 4). The greater the complementarity between the human oligonucleotide and the rhesus monkey sequence, the more likely the human oligonucleotide can cross-react with the cynomolgus monkey sequence. "Start site" indicates the 5'-most nucleotide to which the gapmer is targeted in the rhesus monkey gene sequence. 'Mismatches' indicates the number of nucleobases mismatched between the human oligonucleotide sequence and the rhesus monkey genomic sequence.

TABLE 42

Antisense oligonucleotides complementary to the rhesus rhodopsin genomic sequence (SEQ ID NO: 4)

| ISIS No | Target Start Site | Mismatches | Sequence | Chemistry | SEQ ID NO |
|---|---|---|---|---|---|
| 564426 | 1525 | 1 | TACTCGAAGTGGCTGC | 3-10-3 cEt | 15 |
| 664867 | 1525 | 1 | TACUCGAAGTGGCTGC | Deoxy, 2'-alpha-fluoro and cEt | 64 |
| 664884 | 1525 | 1 | ACTCGAAGTGGCTGC | Deoxy, MOE and cEt | 29 |
| 664844 | 1527 | 1 | GGTACTCGAAGTGGCT | Deoxy, MOE and cEt | 21 |
| 602881 | 6434 | 0 | TCATTCTGCACAGGCG | 3-10-3 cEt | 70 |

Treatment

Prior to the study, the monkeys were kept in quarantine during which the animals were observed daily for general health. The monkeys were 2-4 years old and weighed between 2 and 6 kg. The monkeys were randomized and assigned to groups, as shown the Table below. The monkeys were injected in the left eye (OS) with either PBS or various ASO doses and in the right eye (OD) with various ASO doses. 'OS' stands for 'oculus sinister' (left eye) and 'OD' stands for 'oculus dexter' (right eye).

TABLE 43

Monkey groups

| Group No. | ISIS No | Test material OS/OD | Dose OS/OD (µg/eye) | No. of animals |
|---|---|---|---|---|
| 1 | 564426 | PBS/ASO | 0/150 | 4 |
| 2 | | ASO/ASO | 450/450 | 3 |
| 3 | | ASO/ASO | 750/750 | 2 |
| 4 | | ASO/ASO | 1500/1500 | 1 |
| 5 | 664844 | PBS/ASO | 0/150 | 4 |
| 6 | | ASO/ASO | 450/450 | 3 |
| 7 | | ASO/ASO | 750/750 | 2 |
| 8 | | ASO/ASO | 1500/1500 | 1 |
| 9 | 664867 | PBS/ASO | 0/150 | 4 |
| 10 | | ASO/ASO | 450/450 | 3 |
| 11 | | ASO/ASO | 750/750 | 2 |
| 12 | | ASO/ASO | 1500/1500 | 1 |
| 13 | 664884 | PBS/ASO | 0/150 | 4 |
| 14 | | ASO/ASO | 450/450 | 3 |
| 15 | | ASO/ASO | 750/750 | 2 |
| 16 | | ASO/ASO | 1500/1500 | 1 |
| 17 | 602881 | PBS/ASO | 0/400 | 4 |

Doses were administered on Day 1. Food was withheld prior to sedation. The animals were sedated with ketamine and dexdomitor for the dosing procedure. The eyes were cleansed with Betadine and rinsed with sterile saline. Prior to the dose administration, a mydriatic (1% tropicamide) was instilled in each eye, followed by a topical anesthetic. An intravitreal injection of ASO or PBS was administered in each eye. A lid speculum was inserted to keep the lids open during the procedure and the globe was retracted. The needle was inserted through the sclera and pars plana approximately 4 mm posterior to the limbus. The needle was directed posterior to the lens into the mid vitreous. The test material was slowly injected into the mid-vitreous. Forceps were used to grasp the conjunctiva surrounding the syringe prior to needle withdrawal. Following dosing, all eyes were examined with an indirect ophthalmoscope to identify any visible post-dosing problems and confirm test material deposition. Sedation was reversed with antisedan. A topical antibiotic was dispensed onto each eye immediately following dosing and one day after dosing to prevent infection.

RNA Analysis

On day 70, eyes were collected within 10 min of exsanguination, rapidly frozen by submersion in liquid nitrogen, and placed on dry ice. Eyes were harvested from monkeys that had been treated with 150 µg or 450 µg of ISIS 564426, ISIS 664844, ISIS 664867, ISIS 664884 and 400 µg of ISIS 602881. RNA was extracted from the eye tissue for real-time PCR analysis of mRNA expression. The data from the PBS control eyes were evaluated and the average was calculated.

Results are presented as percent inhibition of mRNA, relative to the PBS control, normalized to cone rod homeobox expression. A '0' value inhibition only indicates that the oligonucleotide did not inhibit expression of in this particular instance.

TABLE 44

% rhodopsin inhibition compared to PBS control

| ISIS No | Dose (μg) | % inhibition |
|---|---|---|
| 564426 | 150 | 0 |
|  | 450 | 25 |
| 664844 | 150 | 8 |
|  | 450 | 14 |
| 664867 | 450 | 21 |
| 664884 | 150 | 10 |
|  | 450 | 46 |
| 602881 | 400 | 54 |

Electroretinography (ERG)

The potential effect of the antisense oligonucleotides on ocular tolerability was determined by measuring the ERG response of the animals following 9 weeks of treatment. The light-adapted b-wave ERG response provided an assessment of the function of the cone photoreceptors and the bipolar cells in the eye (Hood and Birch, Visual Neuroscience. 1992. 8: 107-126; Bouskila et al., Plos One 2014. 9: e111569). Electroretinograms (ERGs) were recorded using a UTAS E-3000 Visual Electrodiagnostic System. Light-adapted b-wave ERG responses in anesthetized monkeys were measured after stimulation with white light at luminance intensity of 2.7 cd·m$^2$.

The results are presented in the Table below as percent of baseline amplitude (means±SD). As shown in the Table below, at the higher dosage of 750 μg of ISTS 564426, ISIS 664867 and ISIS 664884 per eye, the b-wave response trended towards lower levels. Furthermore, response in animals treated with ISIS 564426 trended lower at a dose of 450 μg per eye. These results indicate that ISIS 664844 is more tolerable than ISTS 564426, ISIS 664867, or ISIS 664884.

TABLE 45

Light-adapted (photopic) b-wave amplitude (% baseline)

| | Dose Level (μg/eye) | | | |
|---|---|---|---|---|
| ISIS No | 0 | 150 | 450 | 750 |
| 564426 | 88 ± 24 | 94 ± 27 | 50 ± 18 | 48 ± 19 |
| 664844 | 111 ± 43 | 87 ± 36 | 78 ± 13 | 106 ± 47 |
| 664867 | 83 ± 28 | 69 ± 14 | 53 ± 18 | 25 ± 26 |
| 664884 | 84 ± 7 | 107 ± 41 | 82 ± 29 | 35 ± 24 |

Pathology

After exsanguination, eyes with bulbar conjunctivae and attached optic nerve were collected from various groups and preserved in modified Davidson's fixative for 48-72 hours. The tissues were then transferred to 70% alcohol for at least 24 hours prior to processing to paraffin block. The paraffin-embedded samples were sectioned parallel to the ciliary artery to include optic nerve, macula, and optic disc. After the section was faced, 5 sections at approximately 30-micron steps, were collected. The sections were mounted on glass slides, stained with hematoxylin and eosin and analyzed for histopathology. The findings are presented in the Table below. 'OS' indicates 'outer stripe'; 'IS' indicates 'Inner stripe'; 'ONL' indicates 'outer nuclear layer'; 'INL' indicates 'inner nuclear layer'; 'GCL' indicates 'ganglion cell layer'. These results indicate that ISIS 664844 is more tolerable than ISIS 564426, ISIS 664867, or ISIS 664884.

TABLE 46

Pathology findings in monkey screening study

| | Dose/eye | | |
|---|---|---|---|
| ISIS No | 450 μg | 750 μg | 1500 μg |
| 564426 | Not remarkable | Not remarkable | Min decreased cellularity ONL |
| 664844 | Not remarkable | Not remarkable | Not remarkable |
| 664867 | Not remarkable | Slightly decreased cellularity ONL | Slightly decreased cellularity ONL |
| 664884 | Not remarkable | Slightly decreased cellularity ONL, slight vacuolation ONL | Loss of ONL, IS and OS; Slight decreased cellularity GCL and INL |

Additional Tolerability Assays

Ophthalmic examinations were conducted by an Ophthalmology Individual Scientist once during pretreatment, during week 1 (within 2-4 days following dose administration), and during weeks 3, 6, and 9. The animals were lightly sedated with ketamine prior to this procedure. Slit lamp biomicroscopy and indirect ophthalmoscopy was used. The anterior segment was scored using the Hackett McDonald scale (Hackett, R. B. and McDonald, T. O. 1996. "Assessing Ocular Irritation" in: Dermatotoxicology. 5$^{th}$ edition. Ed. By F. B. Marzuli and H. I. Maiback. Hemisphere Publishing Corp., Washington, D.C.).

Tonometry assessments were performed once pretreatment and during weeks 3 and 9 at approximately the same time of day. Intraocular pressure (IOP) measurements were performed on sedated animals using a pneumotonometer under laboratory light conditions.

Pachymetry (corneal thickness) measurements were performed once pretreatment and during weeks 6 and 9. Measurements of the central cornea was performed on sedated animals.

Non-contact Specular Microscopy (NCSM) was performed once pretreatment and during weeks 5 and 9.

All the assessments are tabulated below. A '✓' sign indicates acceptable results; a 'X' indicates not acceptable. The results indicate that ISIS 664844 is more tolerable compared to ISIS 564426, ISIS 664867, or ISIS 664884.

TABLE 47

Tolerability screen in monkey study

| Test | Utility | ISIS 564426 | ISIS 664844 | ISIS 664867 | ISIS 664884 | ISIS 602881 |
|---|---|---|---|---|---|---|
| Ophthalmic Exam | Cataracts, major retina or vitreous abnormalities | ✓ | ✓ | ✓ | X | ✓ |

TABLE 47-continued

| | Tolerability screen in monkey study | | | | | |
|---|---|---|---|---|---|---|
| Test | Utility | ISIS 564426 | ISIS 664844 | ISIS 664867 | ISIS 664884 | ISIS 602881 |
| Tonometry | IOP | √ | √ | √ | √ | √ |
| Pachymetry | Corneal thickness | √ | √ | √ | √ | √ |
| NCSM | Corneal endothelial cellularity, corneal thickness | √ | √ | √ | √ | X |
| Histology | Cellularity changes | √ | √ | X | X | √ |

Example 11: Screening Summary

Over 400 antisense oligonucleotides (>200 ASOs having a MOE sugar modification and >200 ASOs having a cEt modification) were screened as described in Examples 1-10 above. Out of more than 400 ASOs, ISIS 664844 exhibited the best combination of properties in terms of potency, tolerability, and selectivity for P23H rhodopsin.

What is claimed:

1. A method of treating, ameliorating, or slowing progression of autosomal dominant retinitis pigmentosa (AdRP) in a subject comprising administering to the subject a compound comprising a modified oligonucleotide consisting of 10 to 30 linked nucleosides having a nucleobase sequence comprising any one of SEQ ID NOs: 11-64, thereby treating, ameliorating, or slowing progression of retinitis pigmentosa, wherein the modified oligonucleotide comprises:
   (i) a gap segment consisting of linked deoxynucleosides;
   (ii) a 5' wing segment consisting of linked nucleosides; and
   (iii) a 3' wing segment consisting of linked nucleosides;
   wherein the gap segment is positioned between the 5' wing segment and the 3' wing segment and wherein each nucleoside of each wing segment comprises a modified sugar.

2. The method of claim 1, wherein the subject has a P23H rhodopsin allele.

3. The method of claim 2, wherein administering the compound or composition selectively inhibits expression of P23H rhodopsin over wild-type rhodopsin in the subject.

4. The method of claim 1, wherein said modified oligonucleotide has a nucleobase sequence comprising any one of SEQ ID NOs: 15, 21, 29, or 64.

5. The method of claim 1, wherein said modified oligonucleotide comprises at least one modified internucleoside linkage, at least one modified sugar, or at least one modified nucleobase.

6. The method of claim 5, wherein said modified oligonucleotide comprises at least one modified internucleoside linkage, wherein said modified internucleoside linkage is a phosphorothioate internucleoside linkage.

7. The method of claim 5, wherein said modified oligonucleotide comprises at least one modified sugar, wherein said modified sugar is a bicyclic sugar.

8. The method of claim 7, wherein said bicyclic sugar is selected from the group consisting of: 4'-(CH$_2$)—O-2' (LNA); 4'-(CH$_2$)$_2$—O-2' (ENA); and 4'-CH(CH$_3$)—O-2' (cEt).

9. The method of claim 5, wherein said modified oligonucleotide comprises at least one modified sugar, wherein said modified sugar is 2'-O-methoxyethyl.

10. The method of claim 5, wherein said modified oligonucleotide comprises at least one modified nucleobase, wherein the modified nucleobase is a 5-methylcytosine.

* * * * *

```
                        SEQUENCE LISTING

<160> NUMBER OF SEQ ID NOS: 89

<210> SEQ ID NO 1
<211> LENGTH: 17701
<212> TYPE: DNA
<213> ORGANISM: Homo sapiens

<400> SEQUENCE: 1
tagccgggct cccgagggct gggactcggg tgccccaaga tggctgcatc cagccatctt     60
ggcttagaaa gcccccaca tgccagcttg gccaacaccc acaccatggg tttctctgga    120
ctgcccgaca caaggtgtgg gtgctggcca ggcctgtgtt caaatcccag ctctgcagag    180
gaactttgac cctgcatacc ccagattcct cagtggtcag tggggagtta gaccctcttc    240 ataggggggca ggaggagttg ttcattcatt caacaaatgt ttattgaaca cctcctatgg    300
gttgtgagct cagaggcagc gatgaacagg ccaggctggt cctgcattct agaaatagat    360
gggaagtcag tcaataagta gacaaatgag gccaggtgtg gtggcatgcc tgtagaccca    420
gttactcggg atgctgaggt aggaggatca cttgagccta ggacaggaat tcaaggctgc    480
agtaagctat gattgcgcca ctgcactcca gcctgggcaa cagagcaaga ctcatctcta    540
aaaaacattt aaaaattgtt ttaagaagac aaatgagata gtcgctgatg gtaatgactg    600
tgtaaaaact gaacatggct gggtgtggtt gctcacacct ataatctcag cactttggga    660
ggctgagatt acagcctccc aagtggctcc caaggcagga ggatcacttg agcctgggag    720
ttagagaaca gcttggacaa tatagggaga gcccaactct acaaaaatga aaataaatta    780
gccaggcatg gtggcacaca ccaatggtcc cagctactca ggggttgagg tggtggaccg    840
cttgagccca ggaggttgag gctgcagtga gccatgatca tgccgctgca ctccaacctg    900
agtcacagag tgatacctg tctcaaaaa cataggcca ggtgtggtgg ctcacgcctg    960
taaccccagc actttgggag gccgaggcgg atggatcact tgagatcagg agttagagac   1020
cagcctggct aacatggcaa aatcctgtct gtactaaaaa tataaaaatt agccaggcat   1080
ggcagtacat gcctgtagtc ctggttactt gggaggctaa ggcaggagaa tcgcttgaac   1140
ccaggaagag gaggttgcag tgagccaaga tcacaccact gcactccagc ttgggtgaca   1200
gagtgagacc ctgtctcaaa acagctaaac ctggtggggg tgcctggtgt gtaggatggt   1260
caggggtggt ctctccaagg acatgagtgt gagcggagac ctgaaggaga ctcaggaaga   1320
gattaatact gtcagcaaca aatatattga tcacttacaa gcactcccaa taatcctatt   1380
aggtaggcac tattatcatt cccatttac agagtggaga accgaagcac actctcggga   1440
```

```
gggcggggta gctggctgca cccaggctgt gtagcctcag tccagatgta agggtgggtg   1500
gaaaagagcc ttgcccaatg agggagaaca gtgaaaccaa ggccataggg tctaaagatt   1560
cacgaaccag gctctcatgg agaaagcagg tgaggtttac tgtatagatg ggtgtgcccc   1620 tacccacac tgaggcttcc tcgtctgagc aaactgaggc ccagagaggg gaaggaagca    1680
ggactaccat ggtgactcaa agaccagcta gaatccagcc tcctctcctc gaggcttcca   1740 ctgcccacg ccaggcctgt gtgactcagt ctagggcctt tccattaccc cagctaaacc    1800
tttctttagt catttatacc atggtgtgaa tggctggctg gtctttcctg agagctatct   1860
ttgatgaggg gagggaggca tagccaggtt tgggaagctg ataccccagg aagcccagtt   1920
gactgtgtgg gttatagccc aggctgtcac tgatttgtaa cgggacctga gcaactctgc   1980
agagctaggc ctcagtcttt tcatctgcaa aatggatata gcagagatgg tcagagtagg   2040
tgacttcgaa tgacccttcc agctcactat gagtctgttt tcctgaacaa agagcatttt   2100
ttgtttaaaa aaaaatttct tgggccggac acggtggctc actcctataa tcctggcact   2160 tgggaggcc gaggagggtg gatcgcttga gccaggagtt caggaccagc ctgggcaaca    2220
tagcgagact ccaccctac aaaaaatacaa aaactagtg gtgtgcactt gtggtcccag     2280
ctactcagga ggctgaggtg agaggatcgc ttgagcccag gaggcagagg ctacagtgag   2340
ctatgattgt ggcactgcac tccagcctgg gcgacagaga ccttgtctca aaactttttt   2400
tttcttcgtc aagctttaca gaataaagag cactgtcacc tcagtgatgg ctgttagttc   2460
cccatcacca gggctccatg aggttgcaat tgtgaaactc acaaaggagg aacctgagac   2520 agagaggga agtactgaga tcatctaggt ccattcccc actcactcgt tcattcaaca     2580
aatattcagg agcaccttct aggtgccagg ccctggagac acatcagtga acaaaacaga   2640
catcatccca cctctttcca ctacaggcca agcaccatgc tggtctctgg gaaccctgtt   2700
gtgagcaaga cagacccagg cttacccttg tggactcatg ttacaggcag ggagacgggc   2760
acaaaacaca aataaaaagc ttccatgctg tcagaagcac tatgcaaaaa gcaagatgct   2820
gaggtactgc taagctgtgt gggatggggg ctcagcccgg ccaggagggg gccagttgtg   2880
ggtcagtctt gacccaaggc atccaggaca ccctccttct ggccatgagg gtccacgtca   2940
gaatcaaacc ctcaccttaa cctcattagc gttgggcata atcaccaggc caagcgcctt   3000
aaactacgag aggccccatc ccacccgccc tgccttagcc ctgccacgtg tgccaaacgc   3060
tgttagaccc aacaccaccc aggccaggta gggggctgga gcccaggtgg gctgcaggga   3120 aggggcact cttctgagca gacagatctg ggaatcctgg gtgggaagag agacagtgag    3180
agagagatta agggatattt cccaggcatc agggctttgc actctcaggg gtccttccgc   3240
ctggatgtcc ttcccctgaa gcttcctcct gttgttccgt tctcagctca agctccagct   3300
tctcagagaa gcctcctgtg ttgggagtgg ctgcgactga actgtcccta ctgttattcg   3360
ctcttctatt tgtttgtggt ccctgtgccc cctcacccca caaaaacact ggcttcttgt   3420
gagcaggagc ttgctctttc gtgtaccctg tgtgtcccca aggaccaagc accttgtctg   3480
ggccacagta ggtgctcaat acacatgttg gctggacagt ggtcactgag cggccgcacg   3540
tcgggcactc tcagcacttg cacaggccgc cccagacacc ccacttcatt cctgggaggt   3600
gtcatcatgt tgcttggacg acggggagag ggggacctgc cagtgttggc ctccatttc    3660 ccccagtcat ctgcccccaa ggctctgact actttcttc tcacggtaca tcctgctatt    3720
ctggaatcgg ccctcgtggg gccacctggt acatggcatt tgaggccctc gtggctgatt   3780
```

```
aggcctcccc caacagtgcc ctgtctgctg cctccagggc cagcctcccc ttcagactgg    3840
agtcccctga agggttctgc ccctcccctg ctctggtagc cccctccatc ctccctccct    3900
ccactccatc tttgggggca tttgagtcac ctttctacac cagtgatctg cccaagccac    3960
tgctcacttt cctctggata aagccaggtt ccccggccta gcgttcaaga cccattacaa    4020
ctgcccccag cccagatctt ccccacctag ccacctggca aactgctcct tctctcaaag    4080
gcccaaacat ggcctcccag actgcaaccc ccaggcagtc aggccctgtc tccacaacct    4140
cacagccacc ctggacggaa tctgcttctt cccacatttg agtcctcctc agcccctgag    4200
ctcctctggg cagggctgtt tctttccatc tttgtattcc caggggcctg caaataaatg    4260
tttaatgaac gaacaagaga gtgaattcca attccatgca acaaggattg ggctcctggg    4320
ccctaggcta tgtgtctggc accagaaacg gaagctgcag gttgcagccc ctgccctcat    4380
ggagctcctc ctgtcagagg agtgtgggga ctggatgact ccagaggtaa cttgtggggg    4440
aacgaacagg taaggggctg tgtgacgaga tgagagactg ggagaataaa ccagaaagtc    4500
tctagctgtc cagaggacat agcacagagg cccatggtcc ctatttcaaa cccaggccac    4560
cagactgagc tgggacccttg gacagacaa gtcatgcaga agttagggga ccttctcctc    4620
ccttttcctg gatcctgagt acctctcctc cctgacctca ggcttcctcc tagtgtcacc    4680
ttggcccctc ttagaagcca attaggccct cagtttctgc agcggggatt aatatgatta    4740
tgaacacccc caatctccca gatgctgatt cagccaggag cttaggaggg ggaggtcact    4800
ttataagggt ctgggggggt cagaacccag agtcatccag ctggagccct gagtggctga    4860
gctcaggcct tcgcagcatt cttggtggg agcagccacg ggtcagccac aagggccaca    4920
gccatgaatg gcacagaagg ccctaacttc tacgtgccct tctccaatgc gacgggtgtg    4980
gtacgcagcc ccttcgagta cccacagtac tacctggctg agccatggca gttctccatg    5040
ctggccgcct acatgtttct gctgatcgtg ctgggcttcc ccatcaactt cctcacgctc    5100
tacgtcaccg tccagcacaa gaagctgcgc acgcctctca actacatcct gctcaaccta    5160
gccgtggctg acctcttcat ggtcctaggt ggcttcacca gcaccctcta cacctctctg    5220
catggatact tcgtcttcgg gcccacagga tgcaatttgg agggcttctt tgccaccctg    5280
ggcggtatga gccgggtgtg ggtggggtgt gcaggagccc gggagcatgg aggggtctgg    5340
gagagtcccg ggcttggcgg tggtggctga gaggccttct cccttctcct gtcctgtcaa    5400
tgttatccaa agccctcata tattcagtca acaaacacca ttcatggtga tagccgggct    5460 gctgttgtg cagggctggc actgaacact gccttgatct tatttggagc aatatgcgct    5520
tgtctaattt cacagcaaga aaactgagct gaggctcaaa gaagtcaagc gccctgctgg    5580
ggcgtcacac agggacgggt gcagagttga gttggaagcc cgcatctatc tcgggccatg    5640
tttgcagcac caagcctctg tttcccttgg agcagctgtg ctgagtcaga cccaggctgg    5700
gcactgaggg agagctgggc aagccagacc cctcctctct gggggcccaa gctcagggtg    5760
ggaagtggat tttccattct ccagtcattg ggtcttccct gtgctgggca atgggctcgg    5820 tccctctgg catcctctgc ctcccctctc agcccctgtc ctcaggtgcc cctccagcct    5880
ccctgccgcg ttccaagtct cctggtgttg agaaccgcaa gcagccgctc tgaagcagtt    5940
cctttttgct ttagaataat gtcttgcatt taacaggaaa acagatgggg tgctgcaggg    6000
ataacagatc ccacttaaca gagaggaaaa ctgaggcagg gagagggaa gagactcatt    6060 tagggatgtg gccaggcagc aacaagagcc taggtctcct ggctgtgatc caggaatatc    6120
tctgctgaga tgcaggagga gacgctagaa gcagccattg caaagctggg tgacggggag    6180
```

```
agcttaccgc cagccacaag cgtctctctg ccagccttgc cctgtctccc ccatgtccag   6240
gctgctgcct cggtcccatt ctcagggaat ctctggccat tgttgggtgt ttgttgcatt   6300
caataatcac agatcactca gttctggcca gaaggtgggt gtgccactta cgggtggttg   6360
ttctctgcag ggtcagtccc agtttacaaa tattgtccct ttcactgtta ggaatgtccc   6420
agtttggttg attaactata tggccactct ccctatggaa cttcatgggg tggtgagcag   6480
gacagatgtc tgaattccat catttccttc ttcttcctct gggcaaaaca ttgcacattg   6540
cttcatggct cctaggagag ccccacat gtccgggtta tttcatttcc cgagaaggga   6600
gagggaggaa ggactgccaa ttctgggttt ccaccacctc tgcattcctt cccaacaagg   6660
aactctgccc cacattagga tgcattcttc tgctaaacac acacacacac acacacacac   6720
acaacacaca cacacacaca cacacacaca cacacacaaa actccctacc gggttcccag   6780
ttcaatcctg accccctgat ctgattcgtg tcccttatgg gcccagagcg ctaagcaaat   6840
aacttccccc attccctgga atttctttgc ccagctctcc tcagcgtgtg gtccctctgc   6900
cccttccccc tcctcccagc accaagctct ctccttcccc aaggcctcct caaatccctc   6960
tcccactcct ggttgccttc ctagctaccc tctccctgtc tagggggag tgcaccctcc   7020 ttaggcagtg gggtctgtgc tgaccgcctg ctgactgcct tgcaggtgaa attgccctgt   7080
ggtccttggt ggtcctggcc atcgagcggt acgtggtggt gtgtaagccc atgagcaact   7140
tccgcttcgg ggagaaccat gccatcatgg gcgttgcctt cacctgggtc atggcgctgg   7200
cctgcgccgc accccactc gccggctggt ccaggtaatg gcactgagca aagggaaga   7260 agctccgggg gctcttttgta gggtcctcca gtcaggactc aaacccagta gtgtctggtt   7320
ccaggcactg accttgtatg tctcctggcc caaatgccca ctcagggtag gggtgtaggg   7380
cagaagaaga aacagactct aatgttgcta caagggctgg tcccatctcc tgagccccat   7440
gtcaaacaga atccaagaca tcccaaccct tcaccttggc tgtgcccta atcctcaact   7500 aagctaggcg caaattccaa tcctctttgg tctagtaccc cggggcagc ccctctaac   7560 cttgggcctc agcagcaggg gaggccacac cttcctagtg caggtggcca tattgtggcc   7620
ccttggaact gggtcccact cagcctctag gcgattgtct cctaatgggg ctgagatgag   7680
acacagtggg gacagtggtt tggacaatag gactggtgac tctggtcccc agaggcctca   7740
tgtccctctg tctccagaaa attcccactc tcacttccct ttcctcctca gtcttgctag   7800
ggtccatttc ttaccccttg ctgaatttga gcccaccccc tggacttttt ccccatcttc   7860
tccaatctgg cctagttcta tcctctggaa gcagagccgc tggacgctct gggtttcctg   7920
aggcccgtcc actgtcacca atatcaggaa ccattgccac gtcctaatga cgtgcgctgg   7980
aagcctctag tttccagaag ctgcacaaag atcccttaga tactctgtgt gtccatcttt   8040
ggcctggaaa atactctcac cctggggcta ggaagacctc ggtttgtaca aacttcctca   8100
aatgcagagc ctgagggctc tccccacctc ctcaccaacc ctctgcgtgg catagcccta   8160
gcctcagcgg gcagtggatg ctggggctgg gcatgcaggg agaggctggg tggtgtcatc   8220
tggtaacgca gccaccaaac aatgaagcga cactgattcc acaaggtgca tctgcatccc   8280
catctgatcc attccatcct gtcacccagc catgcagacg tttatgatcc ccttttccag   8340
ggagggaatg tgaagcccca gaaagggcca gcgctcggca gccaccttgg ctgttcccaa   8400
gtccctcaca gcagggtct ccctacctgc ctgtcctcag gtacatcccc gagggcctgc   8460
agtgctcgtg tggaatcgac tactacacgc tcaagccgga ggtcaacaac gagtcttttg   8520
```

```
tcatctacat gttcgtggtc cacttcacca tccccatgat tatcatcttt ttctgctatg    8580
ggcagctcgt cttcaccgtc aaggaggtac gggccggggg gtgggcggcc tcacggctct    8640
gagggtccag cccccagcat gcatctgcgg ctcctgctcc ctggaggagc catggtctgg    8700
acccgggtcc cgtgtcctgc aggccgctgc ccagcagcag gagtcagcca ccacacagaa    8760
ggcagagaag gaggtcaccc gcatggtcat catcatggtc atcgctttcc tgatctgctg    8820
ggtgccctac gccagcgtgg cattctacat cttcacccac cagggctcca acttcggtcc    8880
catcttcatg accatcccag cgttctttgc caagagcgcc gccatctaca accctgtcat    8940
ctatatcatg atgaacaagc aggtgcctac tgcgggtggg agggcccag tgccccaggc     9000
cacaggcgct gcctgccaag gacaagctac ttcccagggc aggggagggg gctccatcag    9060
ggttactggc agcagtcttg ggtcagcagt cccaatgggg agtgtgtgag aaatgcagat    9120
tcctggcccc actcagaact gctgaatctc agggtgggcc caggaacctg catttccagc    9180
aagccctcca caggtggctc agatgctcac tcaggtggga gaagctccag tcagctagtt    9240
ctggaagccc aatgtcaaag tcagaaggac ccaagtcggg aatgggatgg gccagtctcc    9300
ataaagctga ataaggagct aaaaagtctt attctgaggg gtaaagggt aaagggttcc     9360
tcggagaggt acctccgagg ggtaaacagt tgggtaaaca gtctctgaag tcagctctgc    9420
cattttctag ctgtatggcc ctgggcaagt caatttcctt ctctgtgctt tggtttcctc    9480
atccatagaa aggtagaaag ggcaaaaacac caaactcttg gattacaaga gataatttac    9540
agaacaccct tggcacacag agggcaccat gaaatgtcac gggtgacaca gccccttgt    9600
gctcagtccc tggcatctct aggggtgagg agcgtctgcc tagcaggttc cctccaggaa    9660
gctggatttg agtggatggg gcgctggaat cgtgaggggc agaagcaggc aaagggtcgg    9720
ggcgaacctc actaacgtgc cagttccaag cacactgtgg gcagccctgg ccctgactca    9780
agcctcttgc cttccagttc cggaactgca tgctcaccac catctgctgc ggcaagaacc    9840
cactgggtga cgatgaggcc tctgctaccg tgtccaagac ggagcgagc caggtggccc     9900
cggcctaaga cctgcctagg actctgtggc cgactatagg cgtctcccat ccctacacc     9960
ttcccccagc cacagccatc ccaccaggag cagcgcctgt gcagaatgaa cgaagtcaca   10020
taggctcctt aatttttttt ttttttttaa gaaataatta atgaggctcc tcactcacct   10080
gggacagcct gagaagggac atccaccaag acctactgat ctggagtccc acgttcccca   10140
aggccagcgg gatgtgtgcc cctcctcctc ccaactcatc tttcaggaac acgaggattc   10200
ttgctttctg gaaaagtgtc ccagcttagg gataagtgtc tagcacagaa tggggcacac   10260
agtaggtgct taataaatgc tggatggatg caggaaggaa tggaggaatg aatgggaagg   10320
gagaacatat ctatcctctc agaccctcgc agcagcagca actcatactt ggctaatgat   10380
atggagcagt tgttttttccc tccctgggcc tcactttctt ctcctataaa atggaaatcc   10440
cagatccctg gtcctgccga cacgcagcta ctgagaagac caaaagaggt gtgtgtgtgt   10500
ctatgtgtgt gtttcagcac tttgtaaata gcaagaagct gtacagattc tagttaatgt   10560
tgtgaataac atcaattaat gtaactagtt aattactatg attatcacct cctgatagtg   10620
aacattttga gattgggcat tcagatgatg gggtttcacc caaccttggg gcaggttttt   10680
aaaaattagc taggcatcaa ggccagacca gggctggggg ttgggctgta ggcagggaca   10740
gtcacaggaa tgcagaatgc agtcatcaga cctgaaaaaa caacactggg ggaggggac    10800
ggtgaaggcc aagttcccaa tgagggtgag attgggcctg ggtctcacc cctagtgtgg    10860
ggccccaggt cccgtgcctc cccttcccaa tgtggcctat ggagagacag gcctttctct   10920
```

```
cagcctctgg aagccacctg ctcttttgct ctagcacctg ggtcccagca tctagagcat   10980
ggagcctcta gaagccatgc tcacccgccc acatttaatt aacagctgag tccctgatgt   11040
catccttatc tcgaagagct tagaaacaaa gagtgggaaa ttccactggg cctaccttcc   11100
ttggggatgt tcatgggccc cagtttccag tttcccttgc cagacaagcc catcttcagc   11160
agttgctagt ccattctcca ttctggagaa tctgctccaa aaagctggcc acatctctga   11220
ggtgtcagaa ttaagctgcc tcagtaactg ctcccccttc tccatataag caaagccaga   11280
agctctagct ttacccagct ctgcctggag actaaggcaa attgggccat taaaagctca   11340
gctcctatgt tggtattaac ggtggtgggt tttgttgctt tcacactcta tccacaggat   11400
agattgaaac tgccagcttc cacctgatcc ctgaccctgg gatggctgga ttgagcaatg   11460
agcagagcca agcagcacag agtcccctgg ggctagaggt ggaggaggca gtcctgggaa   11520
tgggaaaaac cccaactttg gggtcataga ggcacaggta acccataaaa ctgcaaacaa   11580
gctttgtcac ctctcagagc ttccttatct gcaaaaaaga atcttaaaac tgaccttggc   11640
tgggcacagt ggctcacacc tctaatccca gcactttggg aggccaaggt gggcagatca   11700
cgaggtcagg agtttgagac cagcctgacc aacacggtga aaccctgtct ctactaaaaa   11760
tacaaaaatc agctgggcat ggtggcgcgt gcctgtaatc ccagctattc agtgggctga   11820
ggcaggagaa tcgcttgaac ctgggaggtg gaggttgcag tgagccgaga ttgcgccact   11880
gcactccagc ctgagcaaca gagggacagt ctgtctccaa acaaacaaa acaaacaaac   11940 aaacaaacaa acaaacaaaa aacaacaaca aaaaaccac ttgatcctaa ggggattaga   12000
tgcgactgtg gactttaagt ggccagccta ctgcctggca tgcagcagat gagactatgg   12060
caatactggg cttcagctca gagctggcct tactagagac cctgtcccaa aggggaaaag   12120
gatggagcta aagctcccga gagtcacccc ctcctccgag gtgagaaagg agggcaggag   12180
catgagatag ccgatcctcg gtgccttggt gaggctgggg caaatcatgc tgggatctct   12240
atcattgtcc ctctttactg tgactcacta gataatatca gtcaggatac ttttggtcac   12300
aagtgatagg aaatccaact catttgggct gaagcaaaag ggacacattg ttggctcaca   12360
tgaacaaaaa gcccggggct tcaggcacag ggtatcacca tgactgagat ggggattaat   12420
tctgtgattg gccaagtcta ggtcacctga tcatacgtaa ctcatttatg cctgaggttg   12480 caatttttg gattttttgca atcagacctt ggcgatgacc ttgagcagta ggatataaat   12540
aactcccaca tgcttagcgt tccaataatg gaatactagg catacgcagg tctaactgca   12600
tcaccatggc tggaatgggg attcatcctc tgattggtca gacctaggtc acatgctcac   12660
cctgcagccc aagcaggctg aatggggaga ggtaggtttc acaaaggaaa gcccaggtgc   12720
tgttacctga gtaggaggg caggaggcag ggtgagcaga gccaacatca acccagaggg   12780
aatggaatct aagttggtgt tttctgggca cgtggctgga ccaggcctcc ctccctcatc   12840
atctcaggga catgagggag aagattccta tgggtggtcc cgaaggtctc acccttttgtt   12900 ttggatgctg tgttgggcca gggtggcagt gggtgggaca gtggcatctt agctgccctg   12960
acttgcaggc agcccattcc agctcccgc cccaacccca acccagccca ctttttctga   13020
gaaatggtac atttgcccca gcctcatgtc cagaggaaaa ttttactcta acaccagaac   13080
attctctggt ttgtcctgat agacaagaaa gcctccacct ccttaattta caaatgactt   13140
gacagctgct tcgtgggcac ttgcatacat aaagagaagg agctgctgcc ttaagttgca   13200
gcaagtttgg ccccacctca tctccaggca gccagcagat gtacagagtg cctcttgggt   13260
```

| | |
|---|---|
| acaatggcag ctccattcaa ccaaacctga gcaagctgac cccatgccag aatgcactgg | 13320 |
| ggactcggag atgaattgga gcctagagac caagtctcta ggctatgacc tgggctgcct | 13380 |
| cacggccaca gagctctgtc acgccaaggg agagatgcac ccctgaaagc ctgaggtgcc | 13440 |
| ccataaggag agagtgggtg cccttcccaa ctatgtagct tcaggcaag ttctctttct | 13500 |
| ttcttttct ttctttctct ttctttcttt ctttctttct ttctttcttt ctttctttct | 13560 |
| ttctttcttt ctttctttct ttctttcttt ctttctttct ttgctccttc cttccttcct | 13620 |
| tgcttctttc tttctttctt cttttctttt tctttttttt tttgagatg gggtctcact | 13680 |
| ttgtcaccca gactggagta cagtggtgcc ctcatagctc actgtagcct cgacttctca | 13740 |
| gtttcaagca atccttctgt ctcagcctct caagtagcca ggaccacagg cacacccac | 13800 |
| cacacccaac ttattttta ttttttgtgg agatggagtc tccctatgtt gcccaggctg | 13860 |
| gttttgaact tccagcctca aacgatcctc ctgccttggc ctctcaaagt gctgcgacta | 13920 |
| caggcatgag ccacagcact tggtttgggc aagtccttga attactccaa gactcaggcc | 13980 |
| cctcagctat aaaggagaga attatcccac ttggtagaat tgtctatagg gactaataag | 14040 |
| attaatggtg taaagggtgc tgtgcacagt agacattcaa taaatgtgaa ttcccttccc | 14100 |
| agagacatga actaagttca gaggaggcag ccgcttgtgt ggtgggaaat tgacttgtaa | 14160 |
| ggagattaac acagagaggg gggtcttgca aaagtgggga agcaagtgct aactgccccc | 14220 |
| agtattcatt cccttccctt ctattaacaa tatcatccta ggttctagct gggcacctgg | 14280 |
| ttgctcaaca caagacagca tcttcggct tcttttgcac ctgtggtggc aggatattaa | 14340 |
| ggtccagtca ttgtagggta ctcagaaatg atgtgtgcag tctctaggtt gtgcatttg | 14400 |
| gagaatggaa gtgccctcct tttcctctca tcttttcttc ctgctggctg gaaagcagtc | 14460 |
| atgatgactg gagcttccgc acccatatta gatcatgaga tagaatctga ggacagagaa | 14520 |
| tggcaaagtg ttctctggtg tgtctcacca tggttccccc atgctgcctt aacagccctg | 14580 |
| gccaacttat gcttaaagag tttcaagagg gaagagtttc atggttctt gtttaagtca | 14640 |
| cttgtgattt tggagttata gccaatttct tttccttcct tccttcct cctccctcc | 14700 |
| ctccctccct ccctcccttc cttccttcct tccttcttc ctttcttct ttcttttctg | 14760 |
| agacagagtc ttgctctatt gcccaggctg gagtgcagtg gcataatctt ggctcactac | 14820 |
| aacctctacc tcctgggttc aagcaattct cctgcctcag cctcccgagt agctgggatt | 14880 |
| acaggcacgc accaccttgc ctggctaatt tttttgtattt ttagtagaga cggggttttg | 14940 |
| ccatgttgcc caggctgatc ttgaactcct gagctcaagt aatccgcctg cctcagcctc | 15000 |
| ccaaagtgct gagattacag gcatgagcca ccacgcctgg cctatagcca atttctttac | 15060 |
| taaacaaag ggcttccagg ctgcagccca ggaactcagg aagatcgaag tgcaggtcct | 15120 |
| ctctgaactt cagcttctcc atgtataaat aaaatagtga atataaaata tttacatgga | 15180 |
| tgtcgaatgt ggcagccatt actatttcta ccccgccctt tatatattta ttgactaaaa | 15240 |
| gtcaggaaag aaaagtcaca aatgtcctga tgttacaggg gctggagtta cacaaagcag | 15300 |
| acaccctaaa actgcttcca aaagttcaga actgtgatct tcagaactgt agggcagttc | 15360 |
| acatgtaggc tgaccccatt cagtgtttca taactagttc tcagcagaag ttacatttca | 15420 |
| tacaggcctc agtaaaaaat cacagaagct caccaagcgg cccgttgtcc ctgcagtctg | 15480 |
| atgctcagaa ttaccatttc cctgtaaaaa ggcaatcctc tagaggaatt tttagatcat | 15540 |
| gcagcacatt ttagagcttc ttcccttcaa atgcgaaact tgatcctggc acagccggga | 15600 |
| gcatggtttc ggaagaagct cgtgggaatg tttctatcac tgagtgttgc tctacttctc | 15660 |

```
agttcttgga agtgtcccat aaatgtgatc aaaattgctg cccccacttg tgccaacttc    15720
catttgcctc tttgcttcgt cttctgctcc agcatagtcc cggaagaggg ttttcaggcc    15780
tccagcactg ggacctccag gtatcacagt aatgggtact gagcaccgac cgtgtgccag    15840
gtgctgtgct gggcaccagg gataccacca ggaacaagac agatacagcc ctgctcctca    15900
accagagcgc aaaggctgga gacacggaag cagagctgcg attcagagcg cttgaggctc    15960
tccaggagca aggctgggc  ctggcagagc ccagaggagg ggccctaac  cttctagagg    16020 ccagggaagg cttttctgaa gatgcggcat ctactctgag gccaaaagat gagtgggaaa    16080
gagtccagag aaggggggc  agtgcataca gaggggcttt ctaaggccaa gtgtatcaat    16140
tgacttgtac ggcaagacag acaaccccaa cacttcatgg cttaaaacaa caagctgcat    16200
atcattcatg actctggatc agccaggcag atctgctgat ctgaaccaag cttggtcaat    16260
ttcggctggg ttcattcaag catctgtggt caactggagg gttggctggg gactggctgg    16320
ttgaccctca gatggctggg taacagggt  gatggccata ggcctcagca tctggcaggc    16380
tagctaggag ctagttaaca tggcaatggg actggcatac catcatttct gctattggtc    16440
aaagcaagtc ataagattta aggaatccac tcagacttaa gaaatgtggg aggggccagg    16500
tgcagtggct catgcctgta atccctacac tttgggaggc caggtgggag gtcacttgag    16560
gccaggagtt caagaccagc ctgggcaaca tggcaagact ccatttctaa tatatataca    16620
tacatatata tacacatata tatgtgtatg tgtgtgtgta tatatatata tatatatata    16680
tatatatata tatatatata tatatatata tattttttt  ttaattagcc aggcatagtg    16740
gcatgtgcct gagtcctagc cacttggaag actgaagtag gagatcactt gagcccagaa    16800
ggtcgaggct gcagtgagct atgattgcac cactgcactc cagcctgggc gacagagtgg    16860
aaccctgtct caaaaaacaa acaaacaaac aagaaatgtg agagggttg  caaagttaca    16920 ttgcaaatgg gcaggagtga aaaattgggg gcagttctgc atcaattcaa cacacacaga    16980
ggagacaaaa ggggcccgat atcagcacat ggcccattcc aggagccgca gtgtgggtga    17040
attgtgggat tcaagcgggg aggaggctcc ttaagtcaga ctgaagagca tgaacttca    17100 cccacgggca gtggggagcc atgcaggatg ctaagcgggg gagtgaaatc tgacttcact    17160
ttagaacact ttgatgacca cagcctcccc gagtccagat ctctggtgat ggagagccct    17220
ctgggaaaat tccacaataa agagactacc tagaagaaga tgtatgctgt ttaaaaccca    17280
tcccttcctc agaggtaacc acttctacta ttaccttggt atgaatccat tcagaacttt    17340
tttctactgc ttgtgactgg taagataaaa aaacaaaaaa attttttaaa aattaaaaag    17400
aactattgtg ccttcacaca cacacacaca cacacacaca cacacgcaag ttttgtcttc    17460
tcagtagttg gggtgtactc tccgatacat tctggttcac tccttttcac tactgcatac    17520
tactccactg tgcgaatagg ccacagttta cttgttcact ctccacctga tgggcattta    17580
tgttgttttg aatttctgct aagattgaaa taaacatctt tgcacgtaag tgtatatgtt    17640
tgtctcagat ctacgcctag agtggaatag gtgggttgtg gagtgagtcc ctccttagtt    17700
g                                                                   17701

<210> SEQ ID NO 2
<211> LENGTH: 2768
<212> TYPE: DNA
<213> ORGANISM: Homo sapiens

<400> SEQUENCE: 2
```

| | |
|---|---|
| agagtcatcc agctggagcc ctgagtggct gagctcaggc cttcgcagca ttcttgggtg | 60 |
| ggagcagcca cgggtcagcc acaagggcca cagccatgaa tggcacagaa ggccctaact | 120 |
| tctacgtgcc cttctccaat gcgacgggtg tggtacgcag ccacttcgag tacccacagt | 180 |
| actacctggc tgagccatgg cagttctcca tgctggccgc ctacatgttt ctgctgatcg | 240 |
| tgctgggctt ccccatcaac ttcctcacgc tctacgtcac cgtccagcac aagaagctgc | 300 |
| gcacgcctct caactacatc ctgctcaacc tagccgtggc tgacctcttc atggtcctag | 360 |
| gtggcttcac cagcaccctc tacacctctc tgcatggata cttcgtcttc gggcccacag | 420 |
| gatgcaattt ggagggcttc tttgccaccc tgggcggtga aattgccctg tggtccttgg | 480 |
| tggtcctggc catcgagcgg tacgtggtgg tgtgtaagcc catgagcaac ttccgcttcg | 540 |
| gggagaacca tgccatcatg ggcgttgcct tcacctgggt catggcgctg gcctgcgccg | 600 |
| caccccact cgccggctgg tccaggtaca tccccgaggg cctgcagtgc tcgtgtggaa | 660 |
| tcgactacta cacgctcaag ccggaggtca caacgagtc ttttgtcatc tacatgttcg | 720 |
| tggtccactt caccatcccc atgattatca tcttttttctg ctatgggcag ctcgtcttca | 780 |
| ccgtcaagga ggccgctgcc cagcagcagg agtcagccac cacacagaag gcagagaagg | 840 |
| aggtcacccg catggtcatc atcatggtca tcgctttcct gatctgctgg gtgccctacg | 900 |
| ccagcgtggc attctacatc ttcacccacc agggctccaa cttcggtccc atcttcatga | 960 |
| ccatcccagc gttcttttgcc aagagcgccg ccatctacaa ccctgtcatc tatatcatga | 1020 |
| tgaacaagca gttccggaac tgcatgctca ccaccatctg ctgcggcaag aacccactgg | 1080 |
| gtgacgatga ggcctctgct accgtgtcca agacggagac gagccaggtg gcccccggcct | 1140 |
| aagacctgcc taggactctg tggccgacta taggcgtctc ccatccccta caccttccc | 1200 |
| cagccacagc catcccacca ggagcagcgc ctgtgcagaa tgaacgaagt cacataggct | 1260 |
| ccttaattt ttttttttttt ttaagaaata attaatgagg ctcctcactc acctgggaca | 1320 |
| gcctgagaag ggacatccac caagacctac tgatctggag tcccacgttc ccaaggcca | 1380 |
| gcgggatgtg tgcccctcct cctcccaact catctttcag gaacacgagg attcttgctt | 1440 |
| tctgaaaaag tgtcccagct tagggataag tgtctagcac agaatggggc acacagtagg | 1500 |
| tgcttaataa atgctggatg gatgcaggaa ggaatggagg aatgaatggg aagggagaac | 1560 |
| atatctatcc tctcagaccc tcgcagcagc agcaactcat acttggctaa tgatatggag | 1620 |
| cagttgtttt tccctccctg ggcctcactt tcttctccta taaaatggaa atcccagatc | 1680 |
| cctggtcctg ccgacacgca gctactgaga agaccaaaag aggtgtgtgt gtgtctatgt | 1740 |
| gtgtgtttca gcactttgta aatagcaaga agctgtacag attctagtta atgttgtgaa | 1800 |
| taacatcaat taatgtaact agttaattac tatgattatc acctcctgat agtgaacatt | 1860 |
| ttgagattgg gcattcagat gatggggttt cacccaacct tggggcaggt ttttaaaaat | 1920 |
| tagctaggca tcaaggccag accagggctg ggggttgggc tgtaggcagg acagtcaca | 1980 |
| ggaatgcaga atgcagtcat cagacctgaa aaaacaacac tggggagggg ggacggtgaa | 2040 |
| ggccaagttc ccaatgaggg tgagattggg cctggggtct caccctagt gtggggcccc | 2100 |
| aggtcccgtg cctccccttc ccaatgtggc ctatggagag acaggccttt ctctcagcct | 2160 |
| ctggaagcca cctgctcttt tgctctagca cctgggtccc agcatctaga gcatggagcc | 2220 |
| tctagaagcc atgctcaccc gcccacattt aattaacagc tgagtccctg atgtcatcct | 2280 |
| tatctcgaag agcttagaaa caaagagtgg gaaattccac tgggcctacc ttccttgggg | 2340 |
| atgttcatgg gccccagttt ccagtttccc ttgccagaca agcccatctt cagcagttgc | 2400 |

-continued

```
tagtccattc tccattctgg agaatctgct ccaaaaagct ggccacatct ctgaggtgtc      2460
agaattaagc tgcctcagta actgctcccc cttctccata taagcaaagc cagaagctct      2520
agctttaccc agctctgcct ggagactaag gcaaattggg ccattaaaag ctcagctcct      2580
atgttggtat taacggtggt gggttttgtt gctttcacac tctatccaca ggatagattg      2640
aaactgccag cttccacctg atccctgacc ctgggatggc tggattgagc aatgagcaga      2700
gccaagcagc acagagtccc ctggggctag aggtggagga ggcagtcctg ggaatgggaa      2760
aaacccca                                                              2768
```

<210> SEQ ID NO 3
<211> LENGTH: 2768
<212> TYPE: DNA
<213> ORGANISM: Homo sapiens

<400> SEQUENCE: 3

```
agagtcatcc agctggagcc ctgagtggct gagctcaggc cttcgcagca ttcttgggtg        60
ggagcagcca cgggtcagcc acaagggcca cagccatgaa tggcacagaa ggccctaact       120
tctacgtgcc cttctccaat gcgacggggtg tggtacgcag ccccttcgag tacccacagt      180
actacctggc tgagccatgg cagttctcca tgctggccgc ctacatgttt ctgctgatcg      240
tgctgggctt ccccatcaac ttcctcacgc tctacgtcac cgtccagcac aagaagctgc      300
gcacgcctct caactacatc ctgctcaacc tagccgtggc tgacctcttc atggtcctag      360
gtggcttcac cagcacccttc tacacctctc tgcatggata cttcgtcttc gggcccacag      420
gatgcaattt ggagggcttc tttgccaccc tgggcggtga aattgccctg tggtccttgg      480
tggtcctggc catcgagcgg tacgtggtgg tgtgtaagcc catgagcaac ttccgcttcg      540
ggagaaccca tgccatcatg ggcgttgcct tcacctgggt catggcgctg gcctgcgccg      600 caccccccact cgccggctgg tccaggtaca tccccgaggg cctgcagtgc tcgtgtggaa      660
tcgactacta cacgctcaag ccggaggtca caacgagtc ttttgtcatc tacatgttcg      720
tggtccactt caccatcccc atgattatca tcttttttctg ctatgggcag ctcgtcttca      780
ccgtcaagga ggccgctgcc cagcagcagg agtcagccac cacacagaag gcagagaagg      840
aggtcacccg catggtcatc atcatggtca tcgctttcct gatctgctgg gtgccctacg      900
ccagcgtggc attctacatc ttcacccacc agggctccaa cttcggtccc atcttcatga      960
ccatcccagc gttctttgcc aagagcgccg ccatctacaa ccctgtcatc tatatcatga      1020
tgaacaagca gttccggaac tgcatgctca ccaccatctg ctgcggcaag aacccactgg      1080
gtgacgatga ggcctctgct accgtgtcca gacggagac gagccaggtg gccccggcct      1140
aagacctgcc taggactctg tggccgacta taggcgtctc ccatccccta caccttcccc      1200
cagccacagc catcccacca ggagcagcgc ctgtgcagaa tgaacgaagt cacataggct      1260
ccttaatttt ttttttttttt ttaagaaata ttaatgagg ctcctcactc acctgggaca      1320
gcctgagaag ggacatccac caagacctac tgatctggag tcccacgttc cccaaggcca      1380
gcgggatgtg tgcccctcct cctcccaact catctttcag gaacacgagg attcttgctt      1440
tctggaaaag tgtcccagct tagggataag tgtctagcac agaatggggc acacagtagg      1500
tgcttaataa atgctggatg gatgcaggaa ggaatggagg aatgaatggg aagggagaac      1560
atatctatcc tctcagaccc tcgcagcagc agcaactcat acttggctaa tgatatggag      1620
cagttgtttt tccctcccctg ggcctcactt tcttctccta taaaatggaa atcccagatc      1680
```

```
cctggtcctg ccgacacgca gctactgaga agaccaaaag aggtgtgtgt gtgtctatgt    1740
gtgtgtttca gcactttgta aatagcaaga agctgtacag attctagtta atgttgtgaa    1800
taacatcaat taatgtaact agttaattac tatgattatc acctcctgat agtgaacatt    1860
ttgagattgg gcattcagat gatggggttt cacccaacct tggggcaggt ttttaaaaat    1920
tagctaggca tcaaggccag accagggctg ggggttgggc tgtaggcagg acagtcaca     1980 ggaatgcaga atgcagtcat cagacctgaa aaaacaacac tgggggaggg ggacggtgaa    2040
ggccaagttc ccaatgaggg tgagattggg cctggggtct cacccctagt gtggggcccc    2100
aggtcccgtg cctccccttc ccaatgtggc ctatggagag acaggccttt ctctcagcct    2160
ctggaagcca cctgctcttt tgctctagca cctgggtccc agcatctaga gcatggagcc    2220
tctagaagcc atgctcaccc gcccacattt aattaacagc tgagtccctg atgtcatcct    2280
tatctcgaag agcttagaaa caaagagtgg gaaattccac tgggcctacc ttccttgggg    2340
atgttcatgg gccccagttt ccagtttccc ttgccagaca agcccatctt cagcagttgc    2400
tagtccattc tccattctgg agaatctgct ccaaaaagct ggccacatct ctgaggtgtc    2460
agaattaagc tgcctcagta actgctcccc cttctccata taagcaaagc cagaagctct    2520
agctttaccc agctctgcct ggagactaag gcaaattggg ccattaaaag ctcagctcct    2580
atgttggtat taacggtggt gggttttgtt gctttcacac tctatccaca ggatagattg    2640
aaactgccag cttccacctg atccctgacc ctggatggc tggattgagc aatgagcaga     2700
gccaagcagc acagagtccc ctggggctag aggtggagga ggcagtcctg ggaatgggaa    2760
aaaccccca                                                            2768
```

<210> SEQ ID NO 4
<211> LENGTH: 10001
<212> TYPE: DNA
<213> ORGANISM: Macaca mulatta
<220> FEATURE:
<221> NAME/KEY: misc_feature
<222> LOCATION: (8332)..(8351)
<223> OTHER INFORMATION: n is a, c, g, or t

<400> SEQUENCE: 4

```
gagcggccac acttcgggca ttgtcagcac ctgcacaggc caccctggac accccgcttc      60
attcttagga ggtgtcatcg tgttccttgg acagcgggga gagggggacc tgccagtgtt    120
ggcctccatt tgcccccagc catctgcctc caaggctctt gactactttc tttctcacag    180
tacatcctgc tgttctggaa tcggccgtca tggggccacc tggcacatgg catttgaggc    240
cctcgtagct gaccagacct cccccaacag tgccctgtct gctgcctcca gggctggcct    300 cccctttcaga ctggagtccc ctgaggggct ctgtccctcc cctgctctgg aagccccctc   360
catcctccct ccctccactc catctttggg gcatccgagt cacctttcta ccccagtgat    420
ctgcccaagc cactgcccac ttccctctgg ataaagccag gctccccggc gttcaagacc    480
catcacaact gcccccagct cagtcttccc cacccagcca cctggcaaac tgctccttct    540
ctcaaaggcc caaacgtggc ctcctggact gcatccccca ggcagtcagg cccgtctcc     600 acctcacaga caccttgggc ggaatctgct tcttctcata tctgagtcct cctcagcccc    660
tgagctcctc tgggcagggc tgtttctttc catctttgta ttcccagggg cccacaaata    720 aatgttttaat gaacgaacaa gagagtgaat tccaattcca tgcaacaatg attgggctcc   780
tgggccccag gccatgtgtc cggcactgga aatagaagct gcaggatgca gcccctgccc    840
tcatggagct cctcctgtca gaggagtgtg gggactggac gagcccagaa gtaacttgcg    900
```

```
ggggaatgaa cagctttgta aggggctggg ggaacgaaca ggtaaggggc tgtgtgacga    960
gatgagagac tgggagaata aactagaaag tctctagctg tccagaagct cactgtccag   1020
tccagacgaa gatctgaagt cagctcgtac taagccaagg gaaatggcac agacacccac   1080
ggtccctatt tcagaccaag gccaccagac tgagctggga ccttgggaca dacaagccat   1140
gtagaagtta ggggccttct ccctttccca gggtcctgag tacctctcct ccctgacctc   1200
aggcttcctc ctggtgtcac cttggcccct cttggaagcc aattaggccc tcagtttctg   1260
cagcgggatt aatatgatta tgaacacccc caatctccca gatgctgatt cagccaggag   1320
cttaggaggg ggaggtcact ttataagggt ctgggggggt gagagcccag agtcatccag   1380
ccagagccct gagtggctga gctcaggcct tcgcagcatt cttgggtggg agcagacgcg   1440
gggcagccac aagggccaca gccatgaatg cacggaagg ccctaacttc tacgtgccct    1500
tctccaacgc gacgggcgtg gtgcgcagcc ccttcgagta cccgcagtac tacctggccg   1560
agccatggca gttctccatg ctggccgcct acatgttcct gctgatcgtg ctgggcttcc   1620
ccatcaactt cctcacgctc tacgtcactg tccagcacaa gaagctgcgc acacctctca   1680
actacatcct gctcaaccta gccgtggccg acctcttcat ggtcttcggt ggcttcacca   1740
ccaccctcta cacctctctg catggatact tcgtcttcgg gcccacagga tgcaatgcgg   1800
agggcttctt tgccaccctg ggaggtatga gccgggtgcg ggtggggctt gcaggagccc   1860
gggagcatgg agggatctgg gacagtcccg ggcttggcgg tagtggctga gaggccttct   1920
cccttctcct ctcctgtcag cgttacccaa ggccctcata tattcatcaa caaacaccat   1980
tcatggtgat agctgggctg ctgtttgtgc agggctggct ctgaacgcta ccttgatctt   2040
acctggagca acatgcactt atctaatttc acagccagaa aactgagctg aggctcaaag   2100
aagtcaagtg ccctgctggg ggtcacaatg ggatggggc agagttgagt ttgaagcctg    2160
catccatctt gggccgtgtt ggcaacacca agcctctgtt tccctcggaa aacaggtcag   2220
acccaggctg ggcactgagg agagagctgg gcaagccaga cccctcctct ctgggggccc   2280
aagcccaggg taggaagtgg attctccatt ctccagtcat tgagtcttcc ctgtgctggg   2340
taatgggctc ggtccccttt ggcatcctct gcctcccctc ccagcccccc gtccccgggt   2400
gccctctag cctctgtgcc gcgctccaag gctcctggtg ttgagaactg catgcagccc    2460
ctctgaagca gctgcttttt gctttagaat aatgtcttgc atttaacagg aaaacagatg   2520
ggggtgctgc agggataaca gatcccactt aacagagggg aaaactgagg cagggagaag   2580
ggaatagact tatttaggga tgtggccagg cagcaacaac agcctaggtc tcctggctgt   2640
gatccaggaa tatctccgct gagatggagg agatgttagc ggcagccact gcaaagctgg   2700
gtgacgagga gagcttacca ccagtcacaa gcatcaccct gccagccttg ccctctctcc   2760
cccatgtcca ggttgcctcc tcggtcccat tctcaggaa tctctggcat tgttgggtat    2820
ttgttacatc aaataatcac agatcaccca gttctggcca gaaggtggtg tgccacatac   2880
ggatggttgt tctctgcagg gtcagtccca gtttacaatt attgtcccttt tcactgttag   2940
gaatgtccca gtttggctga ttaactatat ggccactctc cctgtggaac ttcatggggt   3000
ggtgagcagg gcagatgtct caatttcatc atttccttct tcttcctctg gcaaagcat    3060
tgcccattgc ttcatggctc ctaggagagg gccacacttg cccatgttgt ttcatctccc   3120
gagaagagag agggatgaag gactgccaat tctgggtttc cgccacctct gcattcctgc   3180
ccaacaaaga actctgcccc acattaggat gcattcttct gttaaaaaca aacaaaaaac   3240
```

```
cccacaactc cctaccgggt tctcagtcca atcgtgaccc cctgatctga ttcgtgtccc    3300
tcatggaccc agagcactaa gcaaataact tccccattc cctggagctt ctttgcccag     3360
ccctcctcag catgtggtcc ctctgcccct tcccactcct cccagtgcca agctctctcc    3420
ttccccaagg cctcctcaag tccctctccc actcctggtt gccttcctag ctaccctctc    3480
cctatctagg gggagtgcac cctccttaga caggcagtgg ggtctgctga cagcctgctg    3540
actgccttgc aggtgaaatc gccctgtggt ccttggtggt cctggccatc gaacggtacg    3600
tggtggtgtg taagcccatg agcaacttcc gcttcgggga gaaccatgcc atcatgggcg    3660
ttgccttcac ctgggtcatg gcgctggcct gcgccgcacc ccccctcttc ggctggtcca    3720
ggtaatggca ttgagcagaa gggaagaggc tctttgtagg gtcctccagt caggactcaa    3780
acccagtagt gtctggttcc aggcactggc cttgtatgtc tcctggccca aatgcccacc    3840
cagggtaggg gtgtagggca gaagaaatag actctaatgt tgctaaaagc gctggtccca    3900
tctcctgagc tctatgtaaa agagaatcca agacatccca accttcacc ttggctgtgc     3960 ccctaatcct caactaagcc aggcgcaaat tccaatcctc tttggtctag taccctgggg    4020
gcagccccct ctaaccttgg gcctcagcag caggggaggc cacaccttcc tagtgctggt    4080
ggccatattg tggcccttgg gaactgggtc ccattcagcc tctaggcgat tgtctccaaa    4140
tggggctgag atgagacacg gtggggacag tggtttggac aataggaccg gtgactctgg    4200 tccctgagg cctcatgtcc ctctgtctcc agaaaattcc cactctcact tcctttcct     4260 cctcagtctt gctagggtcc atttcttacc ccttgctgaa tttgagtcct ccccctggac    4320 ttttccca tcttctccaa tctggttcca tcctccggaa gcacagcctc tggacgctct     4380
gggtttcctg aggccagtca actgtcacca atatcaggaa ccactgccac atcctaacaa    4440
tgtgccctgg aaacctcgtt tccagaagct gcacaaagat cccttagata ccctgtgtgt    4500
ccatctttga cctggaaaat actctcgccc tggggctagg aaaacctcag tttatacaaa    4560
ctgcctcaaa tacagagcct cccctcctcc tcaccaacct ctgcctggca taaccctagt    4620
ctcagagggc agtggatgct ggggctgggc atgccgggag aggctgggtg gtatcatctg    4680
gtaccgcagc caccagtgaa gcgacactga ttccacaagg tgcgtctgca tccccatctg    4740
atccatattc catcctgtca cccagccatg cagacgctta tgatcccctt ttccaggaag    4800
ggaatgtgaa gccccagaaa gggccagcgc tcggcaggcg ccttggccaa gtccctcaca    4860
ggcgggttct ccctacctgc ccgtcctcag atacatcccc gagggcttgc agtgctcgtg    4920
cggaattgac tactacacgc tcaagccaga ggtcaacaac gagtcctttg ttatctacat    4980
gttcgtggtc cacttcacca tccccatgat tgtcattttc ttctgctacg gcagctcgt    5040 cttcaccgtc aaggaggtac gggccgggga gtgggcagcc tcacggctct gacagtccag    5100
cccccagcat gtatctgcgg ctcctgctcc ctggaggagc catggtctgg acccgggccc    5160
cttgtcttgc aggccgctgc ccagcagcag gagtcggcca ccacacagaa ggcagagaag    5220
gaggtcactc gcatggtcat catcatggtc atcgcttttc tgatctgctg ggtgccctat    5280
gccagcgtgg cattctacat cttcacccac cagggctcca acttcggtcc catcttcatg    5340
accatcccag cgttctttgc caagagcgcc tccatctaca acccctgtcat ctatatcatg    5400 atgaacaagc aggtgcctac tgcgggtggg agggcccag tgtcccagac cacgggcact     5460
gcctgccaag gacaaactgc gtcccagggc aggggagggg gctccatcag ggctactggc    5520
agcagtcttg ggtcagcagt ctcaatgggg agtgtgtgag aaatgcagat tcctggcccc    5580
acccagatct gctgaatctc agggagggcc caggaaccta catttccaac aagctctcca    5640
```

```
caggtggctc agatgctcac tgaggtggga gaagctctag tccagatagt tctggaagcc    5700
caatgtcaaa gtcagaaggt cccaagaggg gaatggatgg gccagtctcc ataaagctta    5760
ataaggagct aaaaagtctt attctgaggg gtaaagggt aaaggggtaa aggttcctct     5820
ccaaggaact cagaagttgg ggtaaacagt ctctgaagtc agctctgcca ttttctaact    5880
atgtgacccc atgcaagtca attccctct ctgtgctttg gtttcctcat ccatagaaag     5940
ggcaaaacac ccaactctca gattacagga gataatttac agaacaccct ggcacacag     6000 agggcaccat gaaatgtcat gggcgacaca gccctctcgt gctgggtccc tggcatctct    6060
aggggtgagg agcgtctgct tagcaagttt cctccaggaa gccagatttg agtggacggg    6120
gcgctggaac tgtgaggggc agaagcaggg aaaaggttgg ggcaaacctc actaacgtgc    6180
cagttccaag cacactgtgg gcagccctgg ccctgactca gcctcttgc cttccagttc     6240 cggaactgca tgctcaccac catctgctgc ggcaagaacc cgctgggtga cgatgaggcc    6300
tctgccaccg tgtccaagac ggagactagc caggtggccc cagcctaaga cctgcctagg    6360
acgctgtggc cgactgtagg cgtctcccgt cccccacacc ctcccccagc cacagccatc    6420
ccaccaggag cagcgcctgt gcagaatgaa cgaagtcaca taggctcctt cattttttt     6480 tttaaagaaa taattaatga gagaaaaatg aggctcctca ctcacccggg acagcctgag    6540
aagggacatc caccaacacc tactgatctg gagtcccagg ttcccaagg ccagtgggat     6600 ctgtgcccct cctcctccca gctcatcttt caggaacatg aggattcttg ctttctggaa    6660
aagtgtccca gcttagggat aagtgtctag cacagaatgg ggcacacagt aggtgcttaa    6720
taaatgctgg atggatgcag gaaggaatgg aggaatgaaa gcgaagggag aacatatcta    6780
tcctctcaga ccctcttagc agcagcaact catacttggc taatgataag gagcagttgt    6840
ttttccctcc ctgggcctca ctttcttccc ctataaaatg gaaatcccag attcctggtc    6900
ctgccgacac gcagctactg agaggaccaa aagaggtgtg tgtgtgtgtg tgtgtgtgtg    6960
tgtgtgtgtc tatgtgtgtg tttcagcacc ttgtaaatag caagagctgt acagattcta    7020
gttcatgttg tgaataacat caattaatgt aactagttaa ttattatgat tatcacctcc    7080
tgattgtgaa cattctgaga ctgggcattc ggatgatggg gtttcaccca gcctcggggc    7140 aggttttta aaattagcta ggcgtcaagg ccagaccagg gctggggctg ggctgcagac     7200
aaggacagtc acaggaatgc agaatgcagt catcacacct gaaaaacaa cattggggga     7260 gtggggcgat gaaggccaag ttctcagtga gggtgagatt gggcctgggg tatcacccct    7320
actgtgaggc cccagacccc gtgcctcccc ttcccagtgt ggcttatgga gagacacgcc    7380
tttctctcag cctctggaag tcacctgctc ttttgcccta gcacctgggc cccagcatct    7440
acagcatgga gcctctggaa gatatgctca ccggcccaca tttaatgaac agctgagtcc    7500
ctgatgtcat ccttatctca aagagcttag aaacaaagag tgggaaattc cactgggccc    7560
accttccctg gggatgttca tgggcccccg tttccagttt cccttgccag acaagcccat    7620
cttcagcagc tgctagtcga ttctccattc tggagagtct gctccagaaa gctggccaca    7680
tctctgaggt gtcagaattg agctgcctca gtaactgctc ccgcctctcc atataggcaa    7740
agccagaagc tctagcttta cccagctctg cctggagact aaggcaaatt gggccattga    7800
aagctcagct cctatgttgg tattaacggt ggtgggtttt gttgctttca aactcttat     7860 ccacaggata gattgaaact gccagcttcc acctgatccc tgaccctggg atggctggat    7920
tgagcaatgg gcagagccaa gcagcacaga gtcccctggg gctagaggtg gaggaagcag    7980
```

```
cctgggaat gagaaaaacc ccaactttgg ggtcatagag tcacaggtga cccataaaac    8040
tgcaaacaag ttttgtcacc tctctgagct tccttatctg caaaagagaa tcttaaaact    8100
gaccttggct gggcacagtg gctcacacct gtaatcccag caccttggga ggccaaggcg    8160
ggcagatcag gaggtcaggg gtttgagacc agcctgacca atatggtgaa gccccatctc    8220
tactaaaaat acaaaaatcg ctgggcatgg tggcaggcgc ctgtaatccc agctacttag    8280
ggggctgagg caggagaatc gcttgaaccc gggaggggaga ggttgcagtg annnnnnnnn    8340
nnnnnnnnnn ncaacagagg gagagtccat ctccaaacaa aacaaaacaa acgaaacaa     8400
acaaacaaca acaacaaaaa acaaacacct gatcctaagg ggattagatg cgattgtgga    8460
ctttaagtgg ccagcctact gcctagcatg cagcagatga gagactttgg cgatactggg    8520
cctcagttca gagctggcct cactagagac cctgtcccaa aggggaacag gatggagctg    8580
tagctcccga gagtcacccc ctcctccaag gtgaggaagg agggcaggag catgagatag    8640
cagatcctcg gtgccttggt ggggctgggg cacattgcgc tgggatctct atcattggcc    8700
ctctttactc tgactcacta ggtagtatca gtcaggatac ttttggttgc aagtgatagg    8760
aaatccagct catttaggct gaagcaaaag gcacacattg ctggctccac atgaccaaaa    8820
agcccggggc ttcaggtaca gcatatcacc atgcctgaga tggtgattaa ttctgtgatt    8880
ggccaggcct aggtcacctg atcatatgtg gctcatttat gcctgaggtt gcaatttttt    8940
ggattttgtgc aatcagacct tggcaatgac cttgaacagt aagatataaa taactcacac    9000
atgcttagcg ttccaataat ggaacactag gcatacacag gtctaactgc atcaccatga    9060
ctggaatggg gattcatcct ctgattggcc agacctaggt cacatgctca ccctgcagcc    9120
caagcaggct gaatggggag aggtaggttt cacaaaggaa agcccaggtg ctgttacctg    9180
aagtaggagg gcaggaggct gggtgagcag agcctgcatc aacccagagg gaatggactc    9240
taagttggta ttttctgggc acatggctgg accaggcctc actgtctcct catctcaagg    9300
acatgaggga gaagattcct atgggtggtc ccaaaggttt tggcacccctt tgttttggat    9360
gctgtgttgg gccagggtgg cagtgggtgg gacagtggca tcttagctgt cctgacttgc    9420
agggagccca tcccagctcc ccaccccaac ccccagccca gtccactttt tctgagaaat    9480
ggtacatttg ccccaacctc atgtccagag gaaaatttta ctctaacacc agaacattct    9540
ctcgtttgtc ctgatagaca ggaaagcctc cacctcctta atttacaaat gacttgacag    9600
ttgcttagtg gcacttgcat acataaagag aaggagctgc tgccctaagc tgcagtaagt    9660
ttgtccacac ttcatctcca ggcagccagc gggaggtaca acctaagagg tacagcctct    9720
taggtacaat gtgactatct ctatcattgt aatgataccct aagaggtaca gcctcttagg    9780
tacaatggca gctccattca atcaaacctg agcaagctga ccccatgcca gaatgcactg    9840
gggactcaga tggccacaga gctctctcac gccaagggag acatgccccc ctgaaagcct    9900
gaggtgcccc ctaaggagac agtgcatgcc ccctaaggag acagtgggtg cccctctcaa    9960
ctatgtagct tcagggcaag tcctcttttc ttttctttct t                        10001
```

<210> SEQ ID NO 5
<211> LENGTH: 23
<212> TYPE: DNA
<213> ORGANISM: Artificial sequence
<220> FEATURE:
<223> OTHER INFORMATION: Primer

<400> SEQUENCE: 5
ggaggtcaac aacgagtctt ttg                                              23

<210> SEQ ID NO 6
<211> LENGTH: 18
<212> TYPE: DNA
<213> ORGANISM: Artificial sequence
<220> FEATURE:
<223> OTHER INFORMATION: Primer

<400> SEQUENCE: 6
ggcctccttg acggtgaa                                         18

<210> SEQ ID NO 7
<211> LENGTH: 30
<212> TYPE: DNA
<213> ORGANISM: Artificial sequence
<220> FEATURE:
<223> OTHER INFORMATION: Probe

<400> SEQUENCE: 7
ttatcatctt tttctgctat gggcagctcg                            30

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
cactataggg agacccaagc                                       20

<210> SEQ ID NO 9
<211> LENGTH: 21
<212> TYPE: DNA
<213> ORGANISM: Artificial sequence
<220> FEATURE:
<223> OTHER INFORMATION: Primer

<400> SEQUENCE: 9 ctgcttttc atggaccacc a                                      21

<210> SEQ ID NO 10
<211> LENGTH: 17
<212> TYPE: DNA
<213> ORGANISM: Artificial sequence
<220> FEATURE:
<223> OTHER INFORMATION: Probe

<400> SEQUENCE: 10
caaagatggt gtggccg                                          17

<210> SEQ ID NO 11
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 11
aagtggctgc gtacca                                           16

<210> SEQ ID NO 12
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 12
ctcgaagtgg ctgcgt                                                              16

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
gtggctgcgt accaca                                                              16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 14
cgaagtggct gcgtac                                                              16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
tactcgaagt ggctgc                                                              16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 16
agtggctgcg taccac                                                              16

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17
gaagtggctg cgtacc                                                              16

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
tcgaagtggc tgcgta                                                              16

```
<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
actcgaagtg gctgcg                                                       16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
gtactcgaag tggctg                                                       16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
ggtactcgaa gtggct                                                       16

<210> SEQ ID NO 22
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 22
gtggctgcgt accac                                                        15

<210> SEQ ID NO 23
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 23
agtggctgcg tacca                                                        15

<210> SEQ ID NO 24
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 24
aagtggctgc gtacc                                                        15

<210> SEQ ID NO 25
<211> LENGTH: 15
<212> TYPE: DNA
<213> ORGANISM: Artificial sequence
<220> FEATURE:
<223> OTHER INFORMATION: Synthetic oligonucleotide
```

<400> SEQUENCE: 25
gaagtggctg cgtac                                                    15

<210> SEQ ID NO 26
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 26
cgaagtggct gcgta                                                    15

<210> SEQ ID NO 27
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 27
tcgaagtggc tgcgt                                                    15

<210> SEQ ID NO 28
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 28
ctcgaagtgg ctgcg                                                    15

<210> SEQ ID NO 29
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 29
actcgaagtg gctgc                                                    15

<210> SEQ ID NO 30
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 30
tactcgaagt ggctg                                                    15

<210> SEQ ID NO 31
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 31
gtactcgaag tggct                                                    15

<210> SEQ ID NO 32
<211> LENGTH: 15

```
-continued

<212> TYPE: DNA
<213> ORGANISM: Artificial sequence
<220> FEATURE:
<223> OTHER INFORMATION: Synthetic oligonucleotide

<400> SEQUENCE: 32
ggtactcgaa gtggc                                                    15

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 33
tggctgcgta ccacac                                                   16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
gggtactcga agtggc                                                   16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 35
tgggtactcg aagtgg                                                   16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
gtgggtactc gaagtg                                                   16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
tgtgggtact cgaagt                                                   16

<210> SEQ ID NO 38
<211> LENGTH: 14
<212> TYPE: DNA
<213> ORGANISM: Artificial sequence
<220> FEATURE:
<223> OTHER INFORMATION: Synthetic oligonucleotide

<400> SEQUENCE: 38
```
agtggctgcg tacc                              14

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 39
taagaaatgg acccta                            16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 40
cccgggtcca gaccat                            16

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tcgaagtggc tgcgtaccac                        20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
tgggtactcg aagtggctgc                        20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
gtgggtactc gaagtggctg                        20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
agtactgtgg gtactcgaag                        20

<210> SEQ ID NO 45
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 45
ggctgcgtac cacacccgtc                                                20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
ctcgaagtgg ctgcgtacca                                                20

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 47
gaagtggctg cgtaccac                                                  18

<210> SEQ ID NO 48
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
cgaagtggct gcgtacca                                                  18

<210> SEQ ID NO 49
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 49
tcgaagtggc tgcgtacc                                                  18

<210> SEQ ID NO 50
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 50
gggtactcga agtggctg                                                  18

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 51
tgggtactcg aagtggct                                                  18
```

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
gggtactcga agtggctgcg                                               20

<210> SEQ ID NO 53
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 53
gtactcgaag tggctgcg                                                 18

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
ggtactcgaa gtggctgc                                                 18

<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 55
ctgtgggtac tcgaagtg                                                 18

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
caggtcttag gccggg                                                   16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
ggggctgcgt accaca                                                   16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

```
<400> SEQUENCE: 58 aagggggctgc gtacca                                                     16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
cgaaggggct gcgtac                                                      16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
ctcgaagggg ctgcgt                                                      16

<210> SEQ ID NO 61
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 61
tactcgaagg ggctgc                                                      16

<210> SEQ ID NO 62
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: bases at these positions are RNA

<400> SEQUENCE: 62
aagtggcugc gtacca                                                      16

<210> SEQ ID NO 63
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: bases at these positions are RNA

<400> SEQUENCE: 63
tactcgaagu ggctgc                                                      16

<210> SEQ ID NO 64
<211> LENGTH: 16
<212> TYPE: DNA
<213> ORGANISM: Artificial sequence
<220> FEATURE:
```

<223> OTHER INFORMATION: Synthetic oligonucleotide
<220> FEATURE:
<221> NAME/KEY: misc_feature
<222> LOCATION: (4)..(4)
<223> OTHER INFORMATION: bases at these positions are RNA

<400> SEQUENCE: 64
tacucgaagt ggctgc                                                       16

<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65
cttgtggctg acccgt                                                       16

<210> SEQ ID NO 66
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 66
gaagttaggg ccttct                                                       16

<210> SEQ ID NO 67
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 67
cagcagagat attcct                                                       16

<210> SEQ ID NO 68
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 68
caggtaggga gaccct                                                       16

<210> SEQ ID NO 69
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 69
cacccgcagt aggcac                                                       16

<210> SEQ ID NO 70
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 70
aggaaattga cttgcc                                          16

<210> SEQ ID NO 71
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 71
agcagaggcc tcatcg                                          16

<210> SEQ ID NO 72
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 72
gagtcctagg caggtc                                          16

<210> SEQ ID NO 73
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 73
ggtggatgtc ccttct                                          16

<210> SEQ ID NO 74
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 74
aaagcaagaa tcctcg                                          16

<210> SEQ ID NO 75
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 75
gctatttaca aagtgc                                          16

<210> SEQ ID NO 76
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 76
actagaatct gtacag                                          16

<210> SEQ ID NO 77
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 77
attaactagt tacatt                                                      16

<210> SEQ ID NO 78
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 78
ccaaggttgg gtgaaa                                                      16

<210> SEQ ID NO 79
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 79
ggtctgatga ctgcat                                                      16

<210> SEQ ID NO 80
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 80
ttcaccgtcc ccctcc                                                      16

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
aggcccaatc tcaccc                                                      16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
aagagcaggt ggcttc                                                      16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
ctaagctctt cgagat                                                      16
```

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
agcagttact gaggca                                               16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
caaaacccac caccgt                                               16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
ttggctctgc tcattg                                               16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
ctgtgctgct tggctc                                               16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
tcattctgca caggcg                                               16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
ggccaatacg ccgtca                                               16